(12) United States Patent
Kelly et al.

(10) Patent No.: US 7,312,233 B2
(45) Date of Patent: Dec. 25, 2007

(54) AMIDE DERIVATIVES AS ION-CHANNEL LIGANDS AND PHARMACEUTICAL COMPOSITIONS AND METHODS OF USING THE SAME

(75) Inventors: Michael G. Kelly, Thousand Oaks, CA (US); John Kincaid, San Mateo, CA (US); Satyanarayana Janagani, Santa Clara, CA (US); Matthew Duncton, San Francisco, CA (US)

(73) Assignee: Renovis, Inc., South San Francisco, CA (US)

( * ) Notice: Subject to any disclaimer, the term of this patent is extended or adjusted under 35 U.S.C. 154(b) by 0 days.

(21) Appl. No.: 11/375,692

(22) Filed: Mar. 14, 2006

(65) Prior Publication Data

US 2006/0205773 A1    Sep. 14, 2006

Related U.S. Application Data

(60) Provisional application No. 60/661,531, filed on Mar. 14, 2005.

(51) Int. Cl.
| | | |
|---|---|---|
| A01N 43/42 | (2006.01) | |
| A61K 31/47 | (2006.01) | |
| C07D 211/72 | (2006.01) | |
| C07D 211/84 | (2006.01) | |
| C07D 213/00 | (2006.01) | |

(52) U.S. Cl. ........................... 514/313; 546/309
(58) Field of Classification Search ........... 546/159, 546/309; 514/313
See application file for complete search history.

(56) References Cited

U.S. PATENT DOCUMENTS

| 5,756,524 A | 5/1998 | Riordan et al. |
|---|---|---|
| 6,013,837 A | 1/2000 | Demassey et al. |
| 6,794,397 B2 | 9/2004 | Cai et al. |
| 2004/0048891 A1 | 3/2004 | Kato et al. |
| 2004/0116399 A1 | 6/2004 | Zhu et al. |
| 2004/0192728 A1* | 9/2004 | Codd et al. ............. 514/313 |
| 2005/0222200 A1 | 10/2005 | Kelly |

OTHER PUBLICATIONS

Michele C. Jetter, Mark A. Youngman, James J. McNally, Sui-Po Zhang, Adrienne E. Dubin, Nadia Nasserb and Scott L. Dax, N-Isoquinolin-5-yl-N0-aralkyl-urea and -amide antagonists of human vanilloid receptor 1 Bioorganic & Medicinal Chemistry Letters 2004, 14, 3053-3056.*
Dorwald F. A. Side Reactions in Organic Synthesis, 2005, Wiley: VCH, Weinheim Chapter 8, pp. 279-308.*
Tafesh, Ahmed M.; Weiguny, Jens "A Review of the Selective Catalytic Reduction of Aromatic Nitro Compounds into Aromatic Amines, Isocyanates, Carbamates, and Ureas Using CO" Chem. Rev. 1996, 96, 2035-2052.*
Fontani, Pierre; Carboni, Bertrand; Vaultier, Michel; Carrie, Robert "Convenient Highly Stereoselective Synthesis of Cyclopropylboronates" Tetrahedron Letters 1989, 30, 4815-4818.*

* cited by examiner

*Primary Examiner*—Rita Desai
*Assistant Examiner*—David K O'Dell
(74) *Attorney, Agent, or Firm*—Klauber & Jackson LLC

(57) ABSTRACT

Compounds are disclosed that have a formula represented by the following:

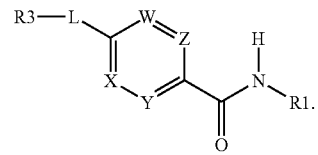

The compounds may be prepared as pharmaceutical compositions, and may be used for the prevention and treatment of a variety of conditions in mammals including humans, including by way of non-limiting example, pain, inflammation, traumatic injury, and others.

23 Claims, 1 Drawing Sheet

AMIDE DERIVATIVES AS ION-CHANNEL LIGANDS AND PHARMACEUTICAL COMPOSITIONS AND METHODS OF USING THE SAME

RELATED APPLICATIONS

The instant application claims the benefit under 35 U.S.C. § 119 of U.S. Provisional Application No. 60/661,531, filed Mar. 14, 2005, the contents of which is hereby incorporated by reference in its entirety.

FIELD OF THE INVENTION

This invention relates to novel compounds and to pharmaceutical compositions containing such compounds. This invention also relates to methods for preventing and/or treating pain and inflammation-related conditions in mammals, such as (but not limited to) arthritis, Parkinson's disease, Alzheimer's disease, stroke, uveitis, asthma, myocardial infarction, the treatment and prophylaxis of pain syndromes (acute and chronic or neuropathic), traumatic brain injury, acute spinal cord injury, neurodegenerative disorders, alopecia (hair loss), inflammatory bowel disease, urinary incontinence, chronic obstructive pulmonary disease, irritable bowel disease, osteoarthritis, and autoimmune disorders, using the compounds and pharmaceutical compositions of the invention.

BACKGROUND OF THE INVENTION

Studies of signaling pathways in the body have revealed the existence of ion channels and sought to explain their role. Ion channels are integral membrane proteins with two distinctive characteristics: they are gated (open and closed) by specific signals such as membrane voltage or the direct binding of chemical ligands and, once open, they conduct ions across the cell membrane at very high rates.

There are many types of ion channels. Based on their selectivity to ions, they can be divided into calcium channel, potassium channel, sodium channel, etc. The calcium channel is more permeable to calcium ions than other types of ions, the potassium channel selects potassium ions over other ions, and so forth. Ion channels may also be classified according to their gating mechanisms. In a voltage-gated ion channel, the opening probability depends on the membrane voltage, whereas in a ligand-gated ion channel, the opening probability is regulated by the binding of small molecules (the ligands). Since ligand-gated ion channels receive signals from the ligand, they may also be considered as "receptors" for ligands.

Examples of ligand-gated ion channels include nAChR (nicotinic acetylcholine receptor) channel, GluR (glutamate receptor) channel, ATP-sensitive potassium channel, G-protein activated channel, cyclic-nucleotide-gated channel, etc.

Transient receptor potential (TRP) channel proteins constitute a large and diverse family of proteins that are expressed in many tissues and cell types. This family of channels mediates responses to nerve growth factors, pheromones, olfaction, tone of blood vessels and metabolic stress et al., and the channels are found in a variety of organisms, tissues and cell types including nonexcitable, smooth muscle and neuronal cells. Furthermore, TRP-related channel proteins are implicated in several diseases, such as several tumors and neurodegenerative disorders and the like. See, for example, Minke, et al., *APStracts* 9:0006P (2002).

Nociceptors are specialized primary afferent neurons and the first cells in a series of neurons that lead to the sensation of pain. The receptors in these cells can be activated by different noxious chemical or physical stimuli. The essential functions of nociceptors include the transduction of noxious stimuli into depolarizations that trigger action potentials, conduction of action potentials from primary sensory sites to synapses in the central nervous system, and conversion of action potentials into neurotransmitter release at presynaptic terminals, all of which depend on ion channels.

One TRP channel protein of particular interest is the vanilloid receptor. Also known as VR1, the vanilloid receptor is a non-selective cation channel which is activated or sensitized by a series of different stimuli including capsaicin, heat and acid stimulation and products of lipid bilayer metabolism (anandamide), and lipoxygenase metabolites. See, for example Smith, et al., *Nature,* 418:186-190 (2002). VR1 does not discriminate among monovalent cations, however, it exhibits a notable preference for divalent cations with a permeability sequence of $Ca^{2+}>Mg^{2+}>Na^+=K^+=Cs^+$. $Ca^{2+}$ is especially important to VR1 function, as extracellular $Ca^{2+}$ mediates desensitization, a process which enables a neuron to adapt to specific stimuli by diminishing its overall response to a particular chemical or physical signal. VR1 is highly expressed in primary sensory neurons in rats, mice and humans, and innervates many visceral organs including the dermis, bones, bladder, gastrointestinal tract and lungs. It is also expressed in other neuronal and non-neuronal tissues including the CNS, nuclei, kidney, stomach and T-cells. The VR1 channel is a member of the superfamily of ion channels with six membrane-spanning domains, with highest homology to the TRP family of ion channels.

VR1 gene knockout mice have been shown to have reduced sensory sensitivity to thermal and acid stimuli. See, for example, Caterina, et al. *Science,* 14:306-313 (2000). This supports the concept that VR1 contributes not only to generation of pain responses but also to the maintenance of basal activity of sensory nerves. VR1 agonists and antagonists have use as analgesics for the treatment of pain of various genesis or etiology, for example acute, inflammatory and neuropathic pain, dental pain and headache (such as migraine, cluster headache and tension headache). They are also useful as anti-inflammatory agents for the treatment of arthritis, Parkinson's Disease, Alzheimer's Disease, stroke, uveitis, asthma, myocardial infarction, the treatment and prophylaxis of pain syndromes (acute and chronic [neuropathic]), traumatic brain injury, spinal cord injury, neurodegenerative disorders, alopecia (hair loss), inflammatory bowel disease, irritable bowel disease and autoimmune disorders, renal disorders, obesity, eating disorders, cancer, schizophrenia, epilepsy, sleeping disorders, cognition, depression, anxiety, blood pressure, lipid disorders, osteoarthritis, and atherosclerosis.

Compounds, such as those of the present invention, which interact with the vanilloid receptor can thus play a role in treating or preventing or ameliorating these conditions.

A wide variety of Vanilloid compounds of different structures are known in the art, for example those disclosed in European Patent Application Numbers, EP 0 347 000 and EP 0 401 903, UK Patent Application Number GB 2226313 and International Patent Application, Publication Number WO 92/09285. Particularly notable examples of vanilloid compounds or vanilloid receptor modulators are capsaicin or trans 8-methyl-N-vanillyl-6-nonenamide which is isolated from the pepper plant, capsazepine (Tetrahedron, 53, 1997, 4791) and olvanil or-N-(4-hydroxy-3-methoxybenzyl)oleamide (J. Med. Chem., 36, 1993, 2595).

International Patent Application, Publication Number WO 02/08221 discloses diaryl piperazine and related compounds which bind with high selectivity and high affinity to vanilloid receptors, especially Type I Vanilloid receptors, also known as capsaicin or VR1 receptors. The compounds are said to be useful in the treatment of chronic and acute pain conditions, itch and urinary incontinence.

International Patent Application, Publication Numbers WO 02/16317, WO 02/16318 and WO 02/16319 suggest that compounds having a high affinity for the vanilloid receptor are useful for treating stomach-duodenal ulcers.

International Patent Application, Publication No. WO 2005/046683, published May 26, 2005, commonly owned, discloses a series of compounds that have demonstrated activity as VR-1 antagonists, and that are suggested as being useful for the treatment of conditions associated with VR-1 activity.

U.S. Pat. No. 3,424,760 and U.S. Pat. No. 3,424,761 both describe a series of 3-Ureidopyrrolidines that are said to exhibit analgesic, central nervous system, and pyschopharmacologic activities. These patents specifically disclose the compounds 1-(1-phenyl-3-pyrrolidinyl)-3-phenyl urea and 1-(1-phenyl-3-pyrrolidinyl)-3-(4-methoxyphenyl)urea respectively. International Patent Applications, Publication Numbers WO 01/62737 and WO 00/69849 disclose a series of pyrazole derivatives which are stated to be useful in the treatment of disorders and diseases associated with the NPY receptor subtype Y5, such as obesity. WO 01/62737 specifically discloses the compound 5-amino-N-isoquinolin-5-yl-1-[3-(trifluoromethyl)phenyl]-1H-pyrazole-3-carboxamide. WO 00/69849 specifically discloses the compounds 5-methyl-N-quinolin-8-yl-1-[3-(trifluoromethyl)phenyl]-1H-pyrazole-3-carboxamide, 5-methyl-N-quinolin-7-yl-1-[3-trifluoromethyl)phenyl]-1H-pyrazole-3-carboxamide, 5-methyl-N-quinolin-3-yl-1-[3-(trifluoromethyl)phenyl]-1H-pyrazole-3-carboxamide, N-isoquinolin-5-yl-5-methyl-1-[3-(trifluoromethyl)phenyl]-1H-pyrazole-3-carboxamide, 5-methyl-N-quinolin-5-yl-1-[3-(trifluoromethyl)phenyl]-1H-pyrazole-3-carboxamide, 1-(3-chlorophenyl)-N-isoquinolin-5-yl-5-methyl-1H-pyrazole-3-carboxamide, N-isoquinolin-5-yl-1-(3-methoxyphenyl)-5-methyl-1H-pyrazole-3-carboxamide, 1-(3-fluorophenyl)-N-isoquinolin-5-yl-5-methyl-1H-pyrazole-3-carboxamide, 1-(2-chloro-5-trifluoromethylphenyl)-N-isoquinolin-5-yl-5-methyl-1N-pyrazole-3-carboxamide, 5-methyl-N-(3-methylisoquinolin-5-yl)-1-[3-(trifluoromethyl)phenyl]-1N-pyrazole-3-carboxamide, 5-methyl-N-(1,2,3,4-tetrahydroisoquinolin-5-yl)-1-[3-(trifluoromethyl)phenyl]-1H-pyrazole-3-carboxamide.

German Patent Application Number 2502588 describes a series of piperazine derivatives. This application specifically discloses the compound N-[3-[2-(diethylamino)ethyl]-1,2-dihydro-4-methyl-2-oxo-7-quinolinyl]-4-phenyl-1-piperazinecarboxamide.

We have now discovered that certain compounds have surprising potency and selectivity as VR-1 antagonists. The compounds of the present invention are considered to be particularly beneficial as VR-1 antagonists as certain compounds exhibit improved aqueous solubility and metabolic stability.

SUMMARY OF THE INVENTION

It has now been found that compounds such as those set forth herein, are capable of modifying mammalian ion channels such as the VR1 cation channel. Accordingly, the present compounds are potent VR1 antagonists with analgesic activity by systemic administration. The compounds of the present invention may show less toxicity, good absorption, good half-life, good solubility, low protein binding affinity, less drug-drug interaction, a reduced inhibitory activity at HERG channel, reduced QT prolongation and good metabolic stability. This finding leads to novel compounds having therapeutic value. It also leads to pharmaceutical compositions having the compounds of the present invention as active ingredients and to their use to treat, prevent or ameliorate a range of conditions in mammals such as but not limited to pain of various genesis or etiology, for example acute, chronic, inflammatory and neuropathic pain, dental pain and headache (such as migraine, cluster headache and tension headache).

Accordingly, in a first aspect of the invention, compounds are disclosed that are capable of modifying ion channels, in vivo, having a formula I:

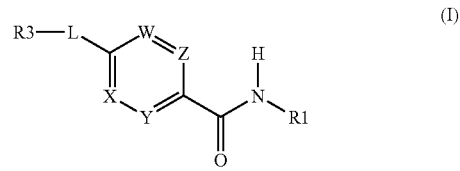

(I)

wherein:

each of W, Z, Y and X is independently N or $CR^4$;

L is substituted or unsubstituted cycloalkyl;

$R^1$ is substituted or unsubstituted aryl, heteroaryl, bicycloaryl or bicycloheteroaryl;

$R^3$ is hydrogen, substituted or unsubstituted aliphatic, alkyl, heteroalkyl, aryl, cycloalkyl, cycloheteroalkyl, heteroaryl, aralkyl, heteroaralkyl, or a hetero group;

each $R^4$ is independently hydrogen, substituted or unsubstituted alkyl, acyl, acylamino, alkylamino, alkylthio, alkoxy, alkoxycarbonyl, alkylarylamino, arylalkyloxy, amino, aryl, arylalkyl, sulfoxide, sulfone, sulfanyl, aminosulfonyl, arylsulfonyl, sulfuric acid, sulfuric acid ester, dihydroxyphosphoryl, aminohydroxyphosphoryl, azido, carboxy, carbamoyl, carboxyl, cyano, cycloheteroalkyl, dialkylamino, halo, heteroaryloxy, heteroaryl, heteroalkyl, hydroxyl, nitro or thio; or a pharmaceutically acceptable salt, solvate or prodrug thereof; and stereoisomers and tautomers thereof.

Accordingly, in a second aspect of the invention, compounds are disclosed that are capable of modifying ion channels, in vivo, having a formula I:

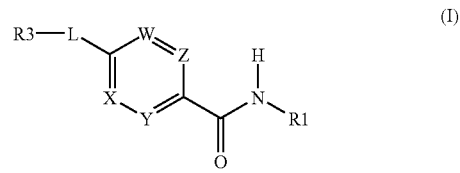

(I)

wherein: each of W, Z, Y and X is independently N or $CR^4$;

L is cycloalkyl substituted with H, halo, $C_1$-$C_6$ alkyl, halo $C_1$-$C_6$ alkyl, or hydroxy $C_1$-$C_6$ alkyl;

$R^1$ is aryl, heteroaryl, bicycloaryl or bicycloheteroaryl substituted with H, halo, $C_1$-$C_6$ alkyl, halo $C_1$-$C_6$ alkyl, hydroxy $C_1$-$C_6$, cyano, $C_1$-$C_6$ alkoxy, halo $C_1$-$C_6$ alkoxy, amino, $C_1$-$C_6$ alkylamino, $C_1$-$C_6$ dialkylamino, aryl, $SO_2$ $C_1$-$C_6$ alkyl, $SO_2$ halo $C_1$-$C_6$ alkyl, $SO_2N(C_1$-$C_6$ alkyl$)_2$, and carboxy;

$R^3$ is halo, $C_1$-$C_6$ alkyl, halo $C_1$-$C_6$ alkyl, or hydroxy $C_1$-$C_6$ alkyl; each $R^4$ is independently hydrogen, $C_1$-$C_6$ alkyl, hydroxyl $C_1$-$C_6$ alkyl, $C_1$-$C_6$ alkylamino, $C_1$-$C_6$ alkoxy, amino $C_1$-$C_6$ alkoxy, substituted amino $C_1$-$C_6$ alkoxy, di $C_1$-$C_6$ alkylamino $C_1$-$C_6$ alkoxy, cycloalkyl $C_1$-$C_6$ alkoxy, $C_1$-$C_6$ alkoxycarbonyl, $C_1$-$C_6$ alkylarylamino, aryl $C_1$-$C_6$ alkyloxy, amino, aryl, aryl $C_1$-$C_6$ alkyl, sulfoxide, sulfone, sulfanyl, aminosulfonyl, arylsulfonyl, sulfuric acid, sulfuric acid ester, azido, carboxy, carbamoyl, cyano, cycloheteroalkyl, di $C_1$-$C_6$ alkylamino, halo, heteroaryloxy, heteroaryl, heteroalkyl, hydroxyl, nitro or thio; or a pharmaceutically acceptable salt, solvate or prodrug thereof; and stereoisomers and tautomers thereof.

In a further embodiment of the invention, compounds of formula I, L is cycloalkyl. In a particular embodiment L is substituted or unsubstituted cyclopropyl. In a yet particular embodiment L is cyclopropyl substituted with H, halo, $C_1$-$C_6$ alkyl, halo $C_1$-$C_6$ alkyl, or hydroxy $C_1$-$C_6$ alkyl.

In a further embodiment of the invention, compounds are disclosed that are capable of modifying ion channels, in vivo, having a formula IA:

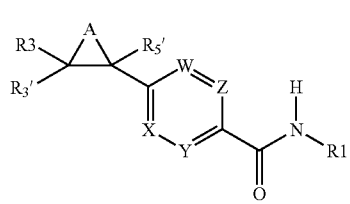

and wherein W, Z, X, Y and $R^1$ are as described for formula I; and wherein A is $CR^5R^6$; each of $R^3$, $R^{3'}$ $R^5$, $R^{5'}$ and $R^6$ is independently selected from hydrogen, substituted or unsubstituted aliphatic, alkyl, heteroalkyl, aryl, cycloalkyl, cycloheteroalkyl, heteroaryl, aralkyl, heteroaralkyl, or a hetero group.

In a further embodiment of the invention, compounds of formula IA, wherein W, Z, X, Y and $R^1$ are as described for formula I; and wherein A is $CR^5R^6$; each of $R^{3'}$, $R^5$, $R^{5'}$ and $R^6$ is independently selected from H, halo, $C_1$-$C_6$ alkyl, halo $C_1$-$C_6$ alkyl, or hydroxy $C_1$-$C_6$ alkyl; and $R^3$ is independently selected from halo, $C_1$-$C_6$ alkyl, halo $C_1$-$C_6$ alkyl, or hydroxy $C_1$-$C_6$ alkyl.

In a further embodiment of the invention, compounds of formula IA, wherein W, Z, X, Y and $R^1$ are as described for formula I; and wherein A is $CR^5R^6$; and wherein each of $R^5$, $R^{5'}$ and $R^6$ is independently H; $R^{3'}$ selected from H, halo, $C_1$-$C_6$ alkyl, halo $C_1$-$C_6$ alkyl, or hydroxy $C_1$-$C_6$ alkyl; and $R^3$ is independently selected from halo, $C_1$-$C_6$ alkyl, halo $C_1$-$C_6$ alkyl, or hydroxy $C_1$-$C_6$ alkyl.

In a further embodiment of the invention, compounds of formula IA, wherein W, Z, X, Y and $R^1$ are as described for formula I; and wherein A is $CR^5R^6$; and wherein each of $R^5$, $R^{5'}$ and $R^6$ is independently H; $R^{3'}$ selected from H, and halo; and $R^3$ is independently selected from halo, $C_1$-$C_6$ alkyl, halo $C_1$-$C_6$ alkyl, or hydroxy $C_1$-$C_6$ alkyl.

In a further embodiment of the invention, compounds of formula IA, wherein W, Z, X, Y and $R^1$ are as described for formula I; and wherein A is $CR^5R^6$; and wherein each of $R^5$, $R^{5'}$ and $R^6$ is independently H; and each of $R^3$ and $R^{3'}$ is Cl.

In a further embodiment of the invention, compounds of formula IA, wherein W, Z, X, Y and $R^1$ are as described for formula I; and wherein A is $CR^5R^6$; and wherein each of $R^3$, $R^5$, $R^{5'}$ and $R^6$ is independently H; and $R^3$ is independently selected from halo, $C_1$-$C_6$ alkyl, halo $C_1$-$C_6$ alkyl, or hydroxy $C_1$-$C_6$ alkyl.

In a further embodiment of the invention, compounds of formula IA, wherein W, Z, X, Y and $R^1$ are as described for formula I; and wherein A is $CR^5R^6$; and wherein each of $R^3$, $R^5$, $R^{5'}$ and $R^6$ is independently H; and $R^3$ is independently selected t-Bu and $CF_3$.

In a further embodiment of the invention, compounds of formula I and IA, $R^1$ is substituted or unsubstituted aryl, heteroaryl, bicycloaryl or bicycloheteroaryl. In one embodiment $R^1$ is substituted or unsubstituted phenyl or pyridyl; and the substitution is selected from H, halo, $C_1$-$C_6$ alkyl, halo $C_1$-$C_6$ alkyl, hydroxy $C_1$-$C_6$, cyano, $C_1$-$C_6$ alkoxy, halo $C_1$-$C_6$ alkoxy, amino, $C_1$-$C_6$ alkylamino, $C_1$-$C_6$ dialkylamino, aryl, $SO_2$ $C_1$-$C_6$ alkyl, $SO_2$ halo $C_1$-$C_6$ alkyl, $SO_2N(C_1$-$C_6$ alkyl$)_2$, and carboxy.

In yet another particular embodiment, with respect to the compounds of formula I and IA, $R^1$ may be substituted or unsubstituted

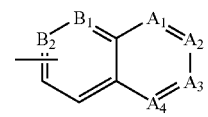

wherein each of $A^1$, $A^2$, $A^3$, $A^4$, $B^1$ and $B^2$ is independently $CR^{4'}$ and N; and each of $R^{4'}$ is independently H, substituted or unsubstituted lower alkyl, halo, hydroxyl, alkoxy, substituted alkoxy, amino, substituted amino, or hydroxyalkyl. In another embodiment, each of $R^{4'}$ is independently H, $C_1$-$C_6$ alkyl, halo, or hydroxy $C_1$-$C_6$ alkyl.

In yet another particular embodiment, with respect to the compounds of formula I and IA, $R^1$ may be substituted or unsubstituted

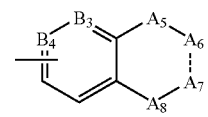

wherein each of $A^5$ and $A^8$ is independently $CR^{4'}R^{4'}$, $NR^{4'}$, O, S, SO or $SO_2$; each of $A^6$ and $A^7$ is independently $CR^{4'}$, $NR^{4'}$, $CR^{4'}R^{4'}$ or CO; each of $B^3$ and $B^4$ is independently; when $R^{4'}$ is attached to C, each $R^{4'}$ is independently H, $C_1$-$C_6$ alkyl, halo, or hydroxy $C_1$-$C_6$ alkyl, and when $R^{4'}$ is attached to N, each $R^{4'}$ is independently H or $C_1$-$C_6$ alkyl; and the dotted bond represents a single or a double bond. In another embodiment $R^{4'}$ is $C_1$-$C_6$ alkyl or hydroxy $C_1$-$C_6$ alkyl.

In yet another particular embodiment, with respect to the compounds of formula I and IA, $R^1$ may be substituted or unsubstituted

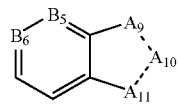

wherein each of $A^9$, $A^{10}$ and $A^{11}$ is independently $CR^{4'}$, $CR^{4'}R^{4'}$, CO, CS, N, $NR^{4'}$, O, S, SO or $SO_2$; each of $B^5$ and $B^6$ is independently $CR^{4'}$; when $R^{4'}$ is attached to C, each $R^{4'}$ is independently H, $C_1$-$C_6$ alkyl, halo, or hydroxy $C_1$-$C_6$ alkyl, and when $R^{4'}$ is attached to N, each $R^{4'}$ is independently H, or $C_1$-$C_6$ alkyl; and each of the dotted bonds independently represents a single or a double bond. In another embodiment $R^{4'}$ is $C_1$-$C_6$ alkyl or hydroxy $C_1$-$C_6$ alkyl.

In yet another particular embodiment, with respect to the compounds of formula I and IA, $R^1$ may be substituted or unsubstituted:

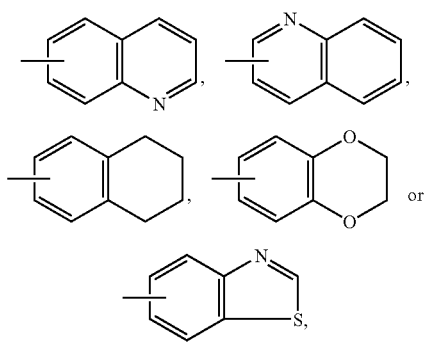

wherein, the ring may be further substituted with $R^{4'}$, and $R^{4'}$ is as described in the preceding paragraphs; and when feasible, the ring N can further be substituted with H or $C_1$-$C_6$ alkyl.

In yet another particular embodiment, with respect to the compounds of formula I and IA, $R^1$ may be substituted or unsubstituted:

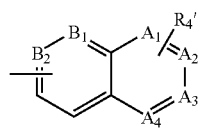

wherein each of $A^1$, $A^2$, $A^3$, $A^4$, $B^1$ and $B^2$ is independently CH and N; and $R^{4'}$ is $C_1$-$C_6$ alkyl or hydroxy $C_1$-$C_6$ alkyl.

In yet another particular embodiment, with respect to the compounds of formula I and IA, $R^1$ may be substituted or unsubstituted:

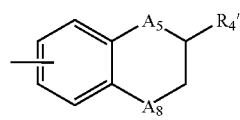

wherein each of $A^5$ and $A^8$ is independently $CH_2$, CHMe, NH, NMe, O, S, SO or $SO_2$; and $R^{4'}$ is $C_1$-$C_6$ alkyl or hydroxy $C_1$-$C_6$ alkyl.

In yet another particular embodiment, with respect to the compounds of formula I and IA, $R^1$ may be substituted or unsubstituted:

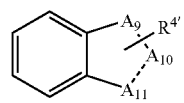

wherein each of $A^9$, $A^{10}$ and $A^{11}$ is independently CH, $CH_2$, N, NH, O, or S; each $R^{4'}$ is independently H, $C_1$-$C_6$ alkyl or hydroxy $C_1$-$C_6$ alkyl; and each of the dotted bonds independently represents a single or a double bond.

In yet another particular embodiment, with respect to the compounds of formula I and IA, $R^1$ may be

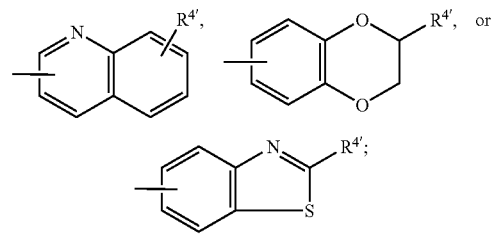

and wherein $R^{4'}$ is as described in the preceding paragraphs.

In one particular embodiment, with respect to the compounds of formula I and IA, $R^1$ is as described in the preceding paragraphs and $R^{4'}$ is alkyl or substituted alkyl. In yet another embodiment $R^{4'}$ is substituted alkyl. In yet another particular embodiment $R^{4'}$ is hydroxy alkyl. In yet another particular embodiment $R^{4'}$ is hydroxymethyl, hydroxyethyl or hydroxypropyl. In yet another particular embodiment $R^{4'}$ is hydroxymethyl.

In one particular embodiment, with respect to the compounds of formula I and IA, $R^1$ is

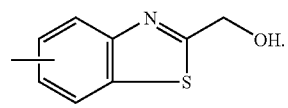

In compounds of formula I and IA, $R^1$ may be substituted or unsubstituted:

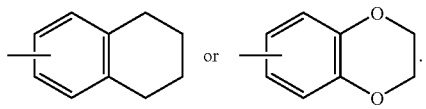

In yet another particular embodiment, with respect to the compounds of formula I and IA, $R^1$ may be:

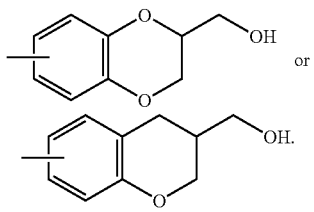

In compounds of formula I and IA, W, Z, X and Y may for example each represent $CR^4$ especially CH. Alternatively X may represent N and W, Z and Y may each represent $CR^4$. In another example set of compounds each of X, Y and Z represents $CR^4$ especially CH. In another example set of compounds W is N. In yet another example set of compounds Y is N.

In another exemplary set of compounds of I and IA, $R^5$, $R^{5'}$ each of W, X and Z represents $CR^4$ especially CH and Y represents $CR^{4''}$. In this example set $R^{4''}$ may for example represent substituted alkyl, halo, sulfone, alkoxy, or amino. Particularly, $R^{4''}$ may represent substituted alkyl or halo. More particularly, $R^{4''}$ may be methyl, chloro, trifluoromethyl or fluoro.

In another exemplary set of compounds of formula I and IA, each of W and X represents $CR^4$ especially CH and each of Y and Z represent $CR^{4''}$. In this example set each $R^{4''}$ may for example represent substituted alkyl, halo, alkoxy, or amino. Particularly, $R^{4''}$ may represent substituted alkyl or halo. More particularly, $R^{4''}$ may be methyl, trifluoromethyl, chloro or fluoro.

In yet another embodiment, the present invention provides amide compounds according to formula II.

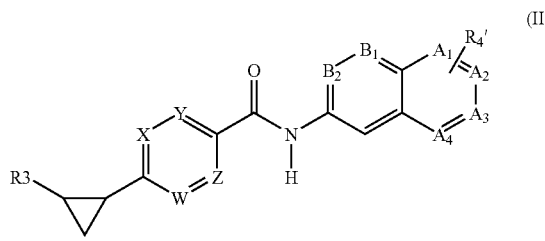

or a pharmaceutically acceptable salt, solvate or prodrug thereof, and stereoisomers and tautomers thereof, wherein: each of W, Z, Y and X is independently N or $CR^4$; each of $A^1$, $A^2$, $A^3$, $A^4$, $B^1$ and $B^2$ is independently N or $CR^4$; $R^3$ is t-Bu or $CF_3$; each $R^4$ is as described for formula I; and $R^{4'}$ is $C_1$-$C_6$ alkyl or hydroxyl $C_1$-$C_6$ alkyl. In one particular embodiment, each of $B^5$ and $B^6$ is independently CH and N.

In yet another embodiment, the present invention provides amide compounds according to formula III or IV.

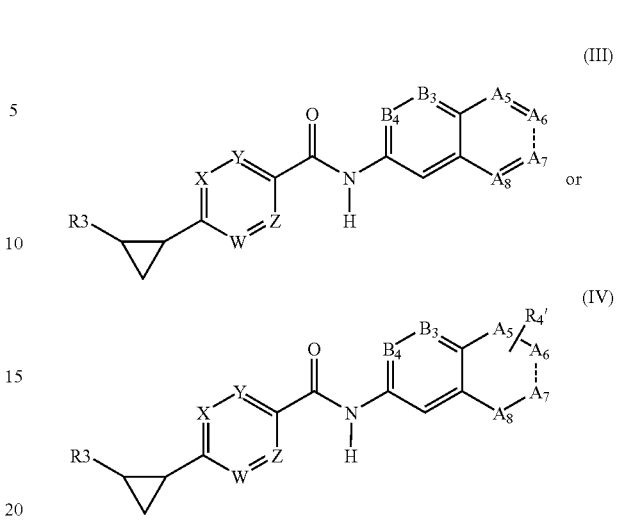

or a pharmaceutically acceptable salt, solvate or prodrug thereof, and stereoisomers and tautomers thereof, wherein: each of $A^5$ and $A^8$ is independently $CR^{4'}R^{4'}$, $NR^{4'}$, O, S, SO or $SO_2$; each of $A^6$ and $A^7$ is independently $CR^{4'}$, $NR^{4'}$, $CR^{4'}R^{4'}$ or CO; each of $B^3$ and $B^4$ is independently $CR^{4'}$; when $R^{4'}$ is attached to C, each of $R^{4'}$ is independently H, $C_1$-$C_6$ alkyl, halo, or hydroxy $C_1$-$C_6$ alkyl, and when $R^{4'}$ is attached to N, each of $R^{4'}$ is independently H or $C_1$-$C_6$ alkyl; and the dotted bond represents a single or a double bond; $R^3$ is t-Bu or $CF_3$; each $R^4$ is as described for formula I; and $R^{4'}$ is $C_1$-$C_6$ alkyl or hydroxyl $C_1$-$C_6$ alkyl.

In yet another embodiment, the present invention provides amide compounds according to formula IV, wherein $R^3$ is t-Bu, or $CF_3$; X and W are independently C—H; Z and Y are independently C—H, C—F, C—Cl, C-Me or C—OMe; $B^3$ and $B^4$ are independently $CR^{4'}$ or N; and wherein each of $A^5$ and $A^8$ is independently $CR^{4'}R^{4'}$, $NR^{4'}$, O, S, SO or $SO_2$; each of $A^6$ and $A^7$ is independently $CR^{4'}$, $NR^{4'}$, $CR^{4'}R^{4'}$ or CO; each of $R^{4'}$ is independently H, substituted or unsubstituted alkyl or aryl; and the dotted bond represents a single or a double bond.

In yet another embodiment, the present invention provides amide compounds according to formula IVA.

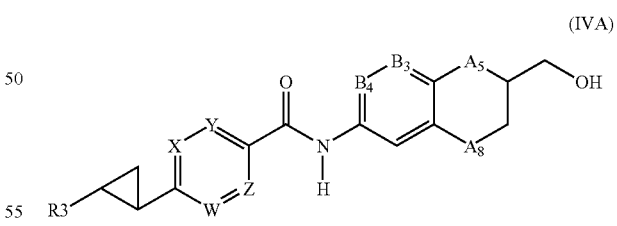

wherein $R^3$ is t-Bu, or $CF_3$; X and W are independently C—H; Z and Y are independently C—H, C—F, C—Cl, C-Me or C—OMe; $B^3$ and $B^4$ are independently $CR^{4'}$; and $A^5$ and $A^8$ are independently O or NH. In one particular embodiment, with respect to the compounds of formula IV or IVA, each of $B^3$ and $B^4$ is independently CH and N.

In one particular embodiment, with respect to the compounds of formula IV or IVA, $A^5$ and $A^8$ both may be O. In one particular embodiment, with respect to the compounds of formula IV or IVA, $A^5$ and $A^8$ both may be NH. In one particular embodiment, with respect to the compounds of formula IV or IVA, $A^5$ may be O and $A^8$ may be NH. In one particular embodiment, with respect to the compounds of formula IV or IVA, $A^5$ may be NH and $A^8$ may be O.

In yet another embodiment, the present invention provides amide compounds according to formula V.

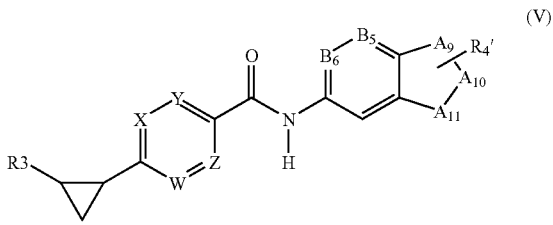

or a pharmaceutically acceptable salt, solvate or prodrug thereof, and stereoisomers and tautomers thereof, wherein: each of $A^9$, $A^{10}$ and $A^{11}$ is independently CH, $CH_2$, N, NH, O, or S; each of $B^5$ and $B^6$ is independently $CR^4$; each $R^{4'}$ is independently H, $C_1$-$C_6$ alkyl or hydroxy $C_1$-$C_6$ alkyl; and each of the dotted bonds independently represents a single or a double bond; $R^3$ is t-Bu or $CF_3$; each $R^4$ is as described for formula I; and $R^{4'}$ is $C_1$-$C_6$ alkyl or hydroxyl $C_1$-$C_6$ alkyl. In one particular embodiment, each of $B^5$ and $B^6$ is independently CH and N.

In yet another embodiment, the present invention provides amide compounds according to formula VI.

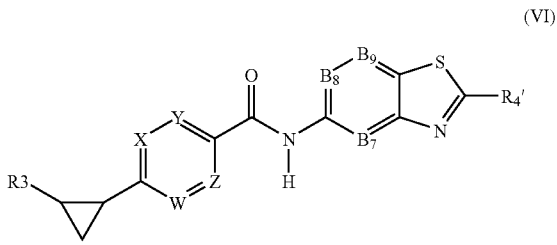

or a pharmaceutically acceptable salt, solvate or prodrug thereof, and stereoisomers and tautomers thereof, wherein each of W, Z, Y and X is independently N or $CR^4$; each of $B^7$, $B^8$ and $B^9$ is independently $CR^4$; $R^3$ is t-Bu or $CF_3$; each $R^4$ is as described for formula I; and $R^{4'}$ is $C_1$-$C_6$ alkyl or hydroxyl $C_1$-$C_6$ alkyl. In one particular embodiment, each of $B^7$, $B^8$ and $B^9$ is independently CH and N.

In one particular embodiment, with respect to the compounds of formula II-VI, Y and Z both may be C—H. In another particular embodiment, with respect to the compounds of formula II-VI, Y is C—H and Z is C—F or C—Cl. In another particular embodiment, with respect to the compounds of formula II-VI, Y is C—H and Z is C—F. In another particular embodiment, with respect to the compounds of formula II-VI, Y is C—H and Z is C—Cl. In a further particular embodiment, with respect to the compounds of formula TI-VI, Y is C—H and Z is C-Me or C—OMe. In one particular embodiment, with respect to the compounds of formula IT-VI, Y and Z both may be C—F. In one particular embodiment, with respect to the compounds of formula II-VI, Y and Z both may be C—Cl.

In a further particular embodiment, in compounds of formula II-VI, W, Z, X and Y may for example each represent $CR^4$, especially CH. Alternatively X may represent N and W, Z and Y may each represent $CR^4$. In another exemplary set of compounds, each of X, Y and Z represents $CR^4$, especially CH. In another example set of compounds W is N. In yet another exemplary set of compounds, Y is N.

In another exemplary set of compounds of formula II-VI, each of W, X and Z represents $CR^4$ especially CH and Y represents $CR^{4''}$. In this example set $R^{4''}$ may for example represent substituted alkyl, halo, alkoxy, or amino. Particularly, $R^{4''}$ may represent substituted alkyl or halo. More particularly, $R^{4''}$ may be methyl, chloro or fluoro.

In another exemplary set of compounds of formula II-VI, each of W and X represents $CR^4$ especially CH and each of Y and Z represent $CR^{4''}$. In this example set each $R^{4''}$ may for example represent substituted alkyl, halo, alkoxy, or amino. Particularly, $R^{4''}$ may represent substituted alkyl or halo. More particularly, $R^{4''}$ may be methyl, chloro or fluoro.

In certain embodiments according to formula II-VI, each of W and X is N or $CR^4$, each of Y and Z is N or $CR^{4''}$ and each $R^{4''}$ is independently selected from hydrogen, alkyl, trihaloalkyl and halo. In certain embodiments, each $R^{4''}$ is independently H, $CH_3$, $CF_3$, Cl, or F. In certain embodiments, each $R^4$ is H.

In certain embodiments according to formula II-VI, each of W, X, and Z is N or CH, and Y is C—$CH_3$, C—Cl, or C—F.

In certain embodiments according to formula II-VI, $R^{4'}$ is hydroxyl substituted alkyl. In certain embodiments according to formula II-VI, $R^{4'}$ is —$(CH_2)_n$—OH wherein n is selected from 1-6. In certain embodiments according to formula II-VI, $R^{4'}$ is $CH_2OH$.

In yet further particular embodiments, the compounds of the invention are set forth and may be selected from a comprehensive listing of such compounds, set forth later on herein in Table 1. The Table contains in 20 compounds that have been or can be synthesized and have as a group, demonstrated activity in their capacity of modifying ion channels, in vivo, and thereby functioning in the therapeutic applications set forth herein in relation to capsaicin and the vanilloid receptor.

The compounds of the present invention are useful for the treatment of inflammatory pain and associated hyperalgesia and allodynia. They are also useful for the treatment of neuropathic pain and associated hyperalgesis and allodynia (e.g. trigeminal or herpetic neuralgia, diabetic neuropathy, causalgia, sympathetically maintained pain and deafferentation syndromes such as brachial plexus avulsion). The compounds of the present invention are also useful as anti-inflammatory agents for the treatment of arthritis, and as agents to treat Parkinson's Disease, Alzheimer's Disease, stroke, uveitis, asthma, myocardial infarction, traumatic brain injury, spinal cord injury, neurodegenerative disorders, alopecia (hair loss), inflammatory bowel disease and autoimmune disorders, renal disorders, obesity, eating disorders, cancer, schizophrenia, epilepsy, sleeping disorders, cognition, depression, anxiety, blood pressure, lipid disorders, and atherosclerosis.

In one aspect, this invention provides compounds which are capable of modifying ion channels, in vivo. Representative ion channels so modified include voltage-gated channels and ligand-gated channels, including cation channels such as vanilloid channels.

In a further aspect, the present invention provides pharmaceutical compositions comprising a compound of the invention, and a pharmaceutical carrier, excipient or diluent.

In this aspect of the invention, the pharmaceutical composition can comprise one or more of the compounds described herein.

In a further aspect of the invention, a method is disclosed for treating mammals, including humans, as well as lower mammalian species, susceptible to or afflicted with a condition from among those listed herein, and particularly, such condition as may be associated with e.g. arthritis, uveitis, asthma, myocardial infarction, traumatic brain injury, acute spinal cord injury, alopecia (hair loss), inflammatory bowel disease and autoimmune disorders, which method comprises administering an effective amount of one or more of the pharmaceutical compositions just described.

In yet another method of treatment aspect, this invention provides a method of treating a mammal susceptible to or afflicted with a condition that gives rise to pain responses or that relates to imbalances in the maintenance of basal activity of sensory nerves. Compounds have use as analgesics for the treatment of pain of various geneses or etiology, for example acute, inflammatory pain (such as pain associated with osteoarthritis and rheumatoid arthritis); various neuropathic pain syndromes (such as post-herpetic neuralgia, trigeminal neuralgia, reflex sympathetic dystrophy, diabetic neuropathy, Guillian Barre syndrome, fibromyalgia, phantom limb pain, post-masectomy pain, peripheral neuropathy, HIV neuropathy, and chemotherapy-induced and other iatrogenic neuropathies); visceral pain, (such as that associated with gastroesophageal reflex disease, irritable bowel syndrome, inflammatory bowel disease, pancreatitis, and various gynecological and urological disorders), dental pain and headache (such as migraine, cluster headache and tension headache).

In additional method of treatment aspects, this invention provides methods of treating a mammal susceptible to or afflicted with neurodegenerative diseases and disorders such as, for example Parkinson's disease, Alzheimer's disease and multiple sclerosis; diseases and disorders which are mediated by or result in neuroinflammation such as, for example traumatic brain injury, stroke, and encephalitis; centrally-mediated neuropsychiatric diseases and disorders such as, for example depression mania, bipolar disease, anxiety, schizophrenia, eating disorders, sleep disorders and cognition disorders; epilepsy and seizure disorders; prostate, bladder and bowel dysfunction such as, for example urinary incontinence, urinary hesitancy, rectal hypersensitivity, fecal incontinence, benign prostatic hypertrophy and inflammatory bowel disease; irritable bowel syndrome, over active bladder, respiratory and airway disease and disorders such as, for example, allergic rhinitis, asthma and reactive airway disease and chronic obstructive pulmonary disease; diseases and disorders which are mediated by or result in inflammation such as, for example rheumatoid arthritis and osteoarthritis, myocardial infarction, various autoimmune diseases and disorders, uveitis and atherosclerosis; itch/pruritus such as, for example psoriasis; alopecia (hair loss); obesity; lipid disorders; cancer; blood pressure; spinal cord injury; and renal disorders method comprises administering an effective condition-treating or condition-preventing amount of one or more of the pharmaceutical compositions just described.

In additional aspects, this invention provides methods for synthesizing the compounds of the invention, with representative synthetic protocols and pathways disclosed later on herein.

Other objects and advantages will become apparent to those skilled in the art from a consideration of the ensuing detailed description, in conjunction with the following illustrative drawings.

DETAILED DESCRIPTION OF THE INVENTION

Definitions

Figure 1:
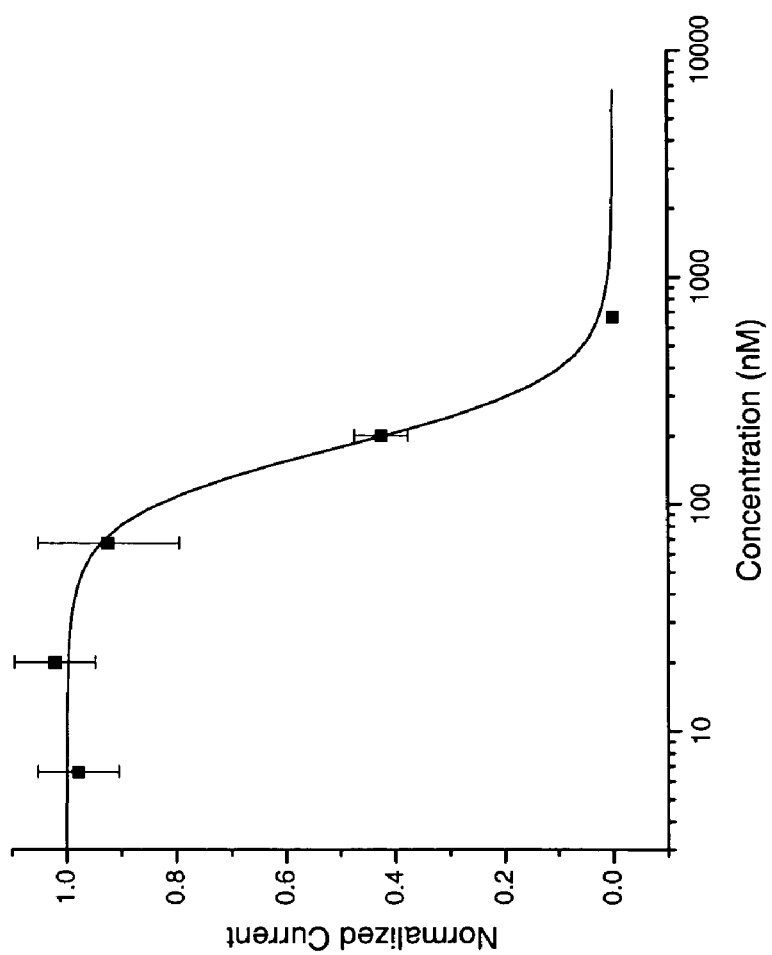
FIG. 1: Graph depicts $IC_{50}$ curve for Compound 7 in *Xenopus oocytes*. The $IC_{50}$ calculated is 177 nM+/−26 (standard error measurement) under the described experimental conditions. Data was obtained using OpusXpress®.

When describing the compounds, pharmaceutical compositions containing such compounds and methods of using such compounds and compositions, the following terms have the following meanings unless otherwise indicated. It should also be understood that any of the moieties defined forth below may be substituted with a variety of substituents, and that the respective definitions are intended to include such substituted moieties within their scope. By way of non-limiting example, such substituents may include e.g. halo (such as fluoro, chloro, bromo), —CN, —CF$_3$, —OH, —OCF$_3$, $C_2$-$C_6$ alkenyl, $C_3$-$C_6$ alkynyl, $C_1$-$C_6$ alkoxy, aryl and di-$C_1$-$C_6$ alkylamino.

"Acyl" refers to a radical —C(O)R, where R is hydrogen, alkyl, cycloalkyl, cycloheteroalkyl, aryl, arylalkyl, heteroalkyl, heteroaryl, heteroarylalkyl as defined herein. Representative examples include, but are not limited to, formyl, acetyl, cylcohexylcarbonyl, cyclohexylmethylcarbonyl, benzoyl, benzylcarbonyl and the like.

"Acylamino" refers to a radical —NR'C(O)R, where R' is hydrogen, alkyl, cycloalkyl, cycloheteroalkyl, aryl, arylalkyl, heteroalkyl, heteroaryl, heteroarylalkyl and R is hydrogen, alkyl, alkoxy, cycloalkyl, cycloheteroalkyl, aryl, arylalkyl, heteroalkyl, heteroaryl or heteroarylalkyl, as defined herein. Representative examples include, but are not limited to, formylamino, acetylamino, cyclohexylcarbonylamino, cyclohexylmethyl-carbonylamino, benzoylamino, benzylcarbonylamino and the like.

"Acyloxy" refers to the group —OC(O)R where R is hydrogen, alkyl, aryl or cycloalkyl.

"Substituted alkenyl" includes those groups recited in the definition of "substituted" herein, and particularly refers to an alkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkoxy" refers to the group —OR where R is alkyl. Particular alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Substituted alkoxy" includes those groups recited in the definition of "substituted" herein, and particularly refers to an alkoxy group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, heteroaryl, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkoxycarbonylamino" refers to the group —NRC(O)OR' where R is hydrogen, alkyl, aryl or cycloalkyl, and R' is alkyl or cycloalkyl.

"Aliphatic" refers to hydrocarbyl organic compounds or groups characterized by a straight, branched or cyclic arrangement of the constituent carbon atoms and an absence of aromatic unsaturation. Aliphatics include, without limitation, alkyl, alkylene, alkenyl, alkenylene, alkynyl and alkynylene. Aliphatic groups typically have from 1 or 2 to about 12 carbon atoms.

"Alkyl" refers to monovalent saturated aliphatic hydrocarbyl groups particularly having up to about 11 carbon atoms, more particularly as a lower alkyl, from 1 to 8 carbon atoms and still more particularly, from 1 to 6 carbon atoms. The hydrocarbon chain may be either straight-chained or branched. This term is exemplified by groups such as methyl, ethyl, n-propyl, isopropyl, n-butyl, iso-butyl, tert-butyl, n-hexyl, n-octyl, tert-octyl and the like. The term "lower alkyl" refers to alkyl groups having 1 to 6 carbon atoms. The term "alkyl" also includes "cycloalkyls" as defined below.

"Substituted alkyl" includes those groups recited in the definition of "substituted" herein, and particularly refers to an alkyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, heteroaryl, keto, nitro, thioalkoxy, substituted thioalkoxy, thioaryloxy, thioketo, thiol, alkyl-S(O)—, aryl-S(O)—, alkyl-S(O)$_2$—, and aryl-S(O)$_2$—.

"Alkylene" refers to divalent saturated aliphatic hydrocarbyl groups particularly having up to about 11 carbon atoms and more particularly 1 to 6 carbon atoms which can be straight-chained or branched. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

"Substituted alkylene" includes those groups recited in the definition of "substituted" herein, and particularly refers to an alkylene group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkenyl" refers to monovalent olefinically unsaturated hydrocarbyl groups preferably having up to about 11 carbon atoms, particularly, from 2 to 8 carbon atoms, and more particularly, from 2 to 6 carbon atoms, which can be straight-chained or branched and having at least 1 and particularly from 1 to 2 sites of olefinic unsaturation. Particular alkenyl groups include ethenyl (—CH═CH$_2$), n-propenyl (—CH$_2$CH═CH$_2$), isopropenyl (—C(CH$_3$)═CH$_2$), vinyl and substituted vinyl, and the like.

"Alkenylene" refers to divalent olefinically unsaturated hydrocarbyl groups particularly having up to about 11 carbon atoms and more particularly 2 to 6 carbon atoms which can be straight-chained or branched and having at least 1 and particularly from 1 to 2 sites of olefinic unsaturation. This term is exemplified by groups such as ethenylene (—CH═CH—), the propenylene isomers (e.g., —CH═CHCH$_2$— and —C(CH$_3$)═CH— and —CH═C(CH$_3$)—) and the like.

"Alkynyl" refers to acetylenically unsaturated hydrocarbyl groups particularly having up to about 11 carbon atoms and more particularly 2 to 6 carbon atoms which can be straight-chained or branched and having at least 1 and particularly from 1 to 2 sites of alkynyl unsaturation. Particular non-limiting examples of alkynyl groups include acetylenic, ethynyl (—C≡CH), propargyl (—CH$_2$C≡CH), and the like.

"Substituted alkynyl" includes those groups recited in the definition of "substituted" herein, and particularly refers to an alkynyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkanoyl" or "acyl" as used herein refers to the group R—C(O)—, where R is hydrogen or alkyl as defined above.

"Aryl" refers to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. Particularly, an aryl group comprises from 6 to 14 carbon atoms.

"Substituted Aryl" includes those groups recited in the definition of "substituted" herein, and particularly refers to an aryl group that may optionally be substituted with 1 or more substituents, for instance from 1 to 5 substituents, particularly 1 to 3 substituents, selected from the group consisting of acyl, acylamino, acyloxy, alkenyl, substituted alkenyl, alkoxy, substituted alkoxy, alkoxycarbonyl, alkyl, substituted alkyl, alkynyl, substituted alkynyl, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, nitro, thioalkoxy, substituted thioalkoxy, thioaryloxy, thiol, alkyl-S(O)—, aryl-S(O)—, alkyl-S(O)$_2$— and aryl-S(O)$_2$—.

"Fused Aryl" refers to an aryl having two of its ring carbon in common with a second aryl ring or with an aliphatic ring.

"Alkaryl" refers to an aryl group, as defined above, substituted with one or more alkyl groups, as defined above.

"Aralkyl" or "arylalkyl" refers to an alkyl group, as defined above, substituted with one or more aryl groups, as defined above.

"Aryloxy" refers to —O-aryl groups wherein "aryl" is as defined above.

"Alkylamino" refers to the group alkyl-NR'R", wherein each of R' and R" are independently selected from hydrogen and alkyl.

"Arylamino" refers to the group aryl-NR'R", wherein each of R' and R" are independently selected from hydrogen, aryl and heteroaryl.

"Alkoxyamino" refers to a radical —N(H)OR where R represents an alkyl or cycloalkyl group as defined herein.

"Alkoxycarbonyl" refers to a radical —C(O)-alkoxy where alkoxy is as defined herein.

"Alkylarylamino" refers to a radical —NRR' where R represents an alkyl or cycloalkyl group and R' is an aryl as defined herein.

"Alkylsulfonyl" refers to a radical —S(O)$_2$R where R is an alkyl or cycloalkyl group as defined herein. Representative examples include, but are not limited to, methylsulfonyl, ethylsulfonyl, propylsulfonyl, butylsulfonyl and the like.

"Alkylsulfinyl" refers to a radical —S(O)R where R is an alkyl or cycloalkyl group as defined herein. Representative examples include, but are not limited to, methylsulfinyl, ethylsulfinyl, propylsulfinyl, butylsulfinyl and the like.

"Alkylthio" refers to a radical —SR where R is an alkyl or cycloalkyl group as defined herein that may be optionally substituted as defined herein. Representative examples include, but are not limited to, methylthio, ethylthio, propylthio, butylthio, and the like.

"Amino" refers to the radical —NH$_2$.

"Substituted amino" includes those groups recited in the definition of "substituted" herein, and particularly refers to the group —N(R)$_2$ where each R is independently selected from the group consisting of hydrogen, alkyl, substituted alkyl, alkenyl, substituted alkenyl, alkynyl, substituted alkynyl, aryl, cycloalkyl, substituted cycloalkyl, and where both R groups are joined to form an alkylene group. When both R groups are hydrogen, —N(R)$_2$ is an amino group.

"Aminocarbonyl" refers to the group —C(O)NRR where each R is independently hydrogen, alkyl, aryl and cycloalkyl, or where the R groups are joined to form an alkylene group.

"Aminocarbonylamino" refers to the group —NRC(O)NRR where each R is independently hydrogen, alkyl, aryl or cycloalkyl, or where two R groups are joined to form an alkylene group.

"Aminocarbonyloxy" refers to the group —OC(O)NRR where each R is independently hydrogen, alkyl, aryl or cycloalky, or where the R groups are joined to form an alkylene group.

"Arylalkyloxy" refers to an —O-arylalkyl radical where arylalkyl is as defined herein.

"Arylamino" means a radical —NHR where R represents an aryl group as defined herein.

"Aryloxycarbonyl" refers to a radical —C(O)—O-aryl where aryl is as defined herein.

"Arylsulfonyl" refers to a radical —S(O)$_2$R where R is an aryl or heteroaryl group as defined herein.

"Azido" refers to the radical —N$_3$.

"Bicycloaryl" refers to a monovalent aromatic hydrocarbon group derived by the removal of one hydrogen atom from a single carbon atom of a parent bicycloaromatic ring system. Typical bicycloaryl groups include, but are not limited to, groups derived from indane, indene, naphthalene, tetrahydronaphthalene, and the like. Particularly, an aryl group comprises from 8 to 11 carbon atoms.

"Bicycloheteroaryl" refers to a monovalent bicycloheteroaromatic group derived by the removal of one hydrogen atom from a single atom of a parent bicycloheteroaromatic ring system. Typical bicycloheteroaryl groups include, but are not limited to, groups derived from benzofuran, benzimidazole, benzindazole, benzdioxane, chromene, chromane, cinnoline, phthalazine, indole, indoline, indolizine, isobenzofuran, isochromene, isoindole, isoindoline, isoquinoline, benzothiazole, benzoxazole, naphthyridine, benzoxadiazole, pteridine, purine, benzopyran, benzpyrazine, pyridopyrimidine, quinazoline, quinoline, quinolizine, quinoxaline, benzomorphan, tetrahydroisoquinoline, tetrahydroquinoline, and the like. Preferably, the bicycloheteroaryl group is between 9-11 membered bicycloheteroaryl, with 5-10 membered heteroaryl being particularly preferred. Particlar bicycloheteroaryl groups are those derived from benzothiophene, benzofuran, benzothiazole, indole, quinoline, isoquinoline, benzimidazole, benzoxazole and benzdioxane.

"Carbamoyl" refers to the radical —C(O)N(R)$_2$ where each R group is independently hydrogen, alkyl, cycloalkyl or aryl, as defined herein, which may be optionally substituted as defined herein.

"Carboxy" refers to the radical —C(O)OH.

"Carboxyamino" refers to the radical —N(H)C(O)OH.

"Cycloalkyl" refers to cyclic hydrocarbyl groups having from 3 to about 10 carbon atoms and having a single cyclic ring or multiple condensed rings, including fused and bridged ring systems, which optionally can be substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, and multiple ring structures such as adamantanyl, and the like.

"Substituted cycloalkyl" includes those groups recited in the definition of "substituted" herein, and particularly refers to a cycloalkyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Cycloalkoxy" refers to the group —OR where R is cycloalkyl. Such cycloalkoxy groups include, by way of example, cyclopentoxy, cyclohexoxy and the like.

"Cycloalkenyl" refers to cyclic hydrocarbyl groups having from 3 to 10 carbon atoms and having a single cyclic ring or multiple condensed rings, including fused and bridged ring systems and having at least one and particularly from 1 to 2 sites of olefinic unsaturation. Such cycloalkenyl groups include, by way of example, single ring structures such as cyclohexenyl, cyclopentenyl, cyclopropenyl, and the like.

"Substituted cycloalkenyl" includes those groups recited in the definition of "substituted" herein, and particularly refers to a cycloalkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Fused Cycloalkenyl" refers to a cycloalkenyl having two of its ring carbon atoms in common with a second aliphatic or aromatic ring and having its olefinic unsaturation located to impart aromaticity to the cycloalkenyl ring.

"Cyanato" refers to the radical —OCN.

"Cyano" refers to the radical —CN.

"Dialkylamino" means a radical —NRR' where R and R' independently represent an alkyl, substituted alkyl, aryl, substituted aryl, cycloalkyl, substituted cycloalkyl, cycloheteroalkyl, substituted cycloheteroalkyl, heteroaryl, or substituted heteroaryl group as defined herein.

"Ethenyl" refers to substituted or unsubstituted —(C=C)—.

"Ethylene" refers to substituted or unsubstituted —(C—C)—.

"Ethynyl" refers to —(C≡C)—.

"Halo" or "halogen" refers to fluoro, chloro, bromo and iodo. Preferred halo groups are either fluoro or chloro.

"Hydroxy" refers to the radical —OH.

"Nitro" refers to the radical —NO$_2$.

"Substituted" refers to a group in which one or more hydrogen atoms are each independently replaced with the same or different substituent(s). Typical substituents include, but are not limited to, —X, —R$^{14}$, —O$^-$, =O, —OR$^{14}$, —SR$^{14}$, —S$^-$, =S, —NR$^{14}$R$^{15}$, =NR$^{14}$, —CX$_3$, —CF$_3$, —CN, —OCN, —SCN, —NO, —NO$_2$, =N$_2$, —N$_3$, —S(O)$_2$O$^-$, —S(O)$_2$OH, —S(O)$_2$R$^{14}$, —OS(O$_2$)O$^-$, —OS(O)$_2$R$^{14}$, —P(O)(O$^-$)$_2$, —P(O)(OR$^{14}$)(O$^-$), —OP(O)(OR$^{14}$)(OR$^{15}$), —C(O)R$^{14}$, —C(S)R$^{14}$, —C(O)OR$^{14}$, —C(O)NR$^{14}$R$^{15}$, —C(O)O$^-$, —C(S)OR$^{14}$, —NR$^{16}$C(O)NR$^{14}$R$^{15}$, —NR$^{16}$C(S)NR$^{14}$R$^{15}$, —NR$^{17}$C(NR$^{16}$)NR$^{14}$R$^{15}$ and —C(NR$^{16}$)NR$^{14}$R$^{15}$, where each X is independently a halogen; each R$^{14}$, R$^{15}$, R$^{16}$ and R$^{17}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl, substituted heteroarylalkyl, —NR$^{18}$R$^{19}$, —C(O)R$^{18}$ or —S(O)$_2$R$^{18}$ or optionally R$^{18}$ and R$^{19}$ together with the atom to which they are both attached form a cycloheteroalkyl or substituted cycloheteroalkyl ring; and R$^{18}$ and R$^{19}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl or substituted heteroarylalkyl.

Examples of representative substituted aryls include the following

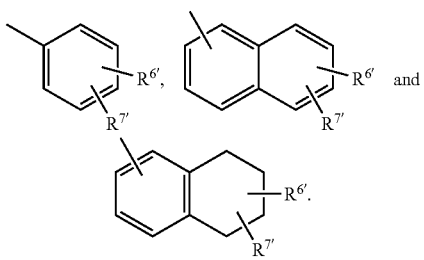

In these formulae one of R$^{6'}$ and R$^{7'}$ may be hydrogen and at least one of R$^{6'}$ and R$^{7'}$ is each independently selected from alkyl, alkenyl, alkynyl, cycloheteroalkyl, alkanoyl, alkoxy, aryloxy, heteroaryloxy, alkylamino, arylamino, heteroarylamino, NR$^{10}$COR$^{11}$, NR$^{10}$SOR$^{11}$, NR$^{10}$SO$_2$R$^{14}$, COOalkyl, COOaryl, CONR$^{10}$R$^{11}$, CONR$^{10}$OR$^{11}$, NR$^{10}$R$^{11}$, SO$_2$NR$^{10}$R$^{11}$, S-alkyl, S-alkyl, SOalkyl, SO$_2$alkyl, Saryl, SOaryl, SO$_2$aryl; or R$^{6'}$ and R$^{7'}$ may be joined to form a cyclic ring (saturated or unsaturated) from 5 to 8 atoms, optionally containing one or more heteroatoms selected from the group N, O or S. R$^{10}$, R$^{11}$, and R$^{12}$ are independently hydrogen, alkyl, alkenyl, alkynyl, perfluoroalkyl, cycloalkyl, cycloheteroalkyl, aryl, substituted aryl, heteroaryl, substituted or hetero alkyl or the like.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. cycloheteroalkyl, aryl, e.g. heteroaryl, cycloalkenyl, cycloheteroalkenyl, and the like having from 1 to 5, and especially from 1 to 3 heteroatoms.

"Heteroaryl" refers to a monovalent heteroaromatic group derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group is between 5-20 membered heteroaryl, with 5-10 membered heteroaryl being particularly preferred. Particlar heteroaryl groups are those derived from thiophene, pyrrole, benzothiophene, benzofuran, indole, pyridine, quinoline, imidazole, oxazole and pyrazine.

Examples of representative heteroaryls include the following:

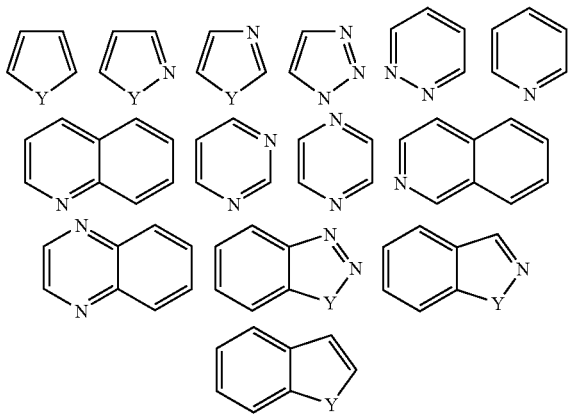

wherein each Y is selected from carbonyl, N, NR$^4$, O, and S.

Examples of representative cycloheteroalkyls include the following

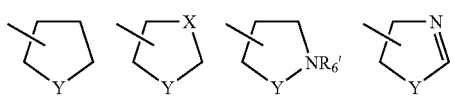

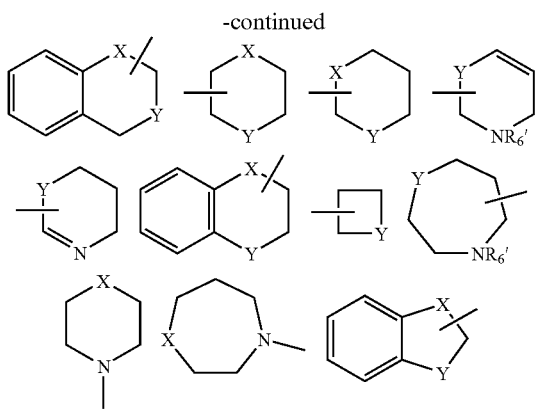

wherein each X is selected from $CR^4_2$, $NR^4$, O and S; and each Y is selected from $NR^4$, O and S, and where $R^{6'}$ is $R^2$.

Examples of representative cycloheteroalkenyls include the following:

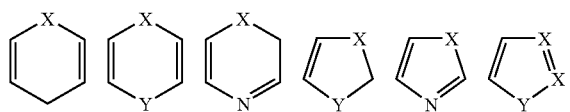

wherein each X is selected from $CR^4$, $NR^4$, O and S; and each Y is selected from carbonyl, N, $NR^4$, O and S.

Examples of representative aryl having hetero atoms containing substitution include the following:

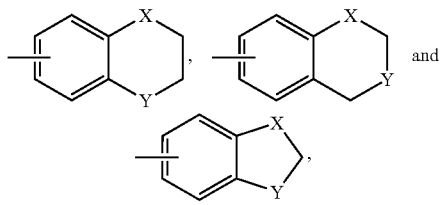

wherein each X is selected from C—$R^4$, $CR^4_2$, $NR^4$, O and S; and each Y is selected from carbonyl, $NR^4$, O and S.

"Hetero substituent" refers to a halo, O, S or N atom-containing functionality that may be present as an $R^4$ in a $R^4C$ group present as substituents directly on A, B, W, X, Y or Z of the compounds of this invention or may be present as a substituent in the "substituted" aryl and aliphatic groups present in the compounds.

Examples of hetero substituents include:
-halo,
—$NO_2$, —$NH_2$, —NHR, —$N(R)_2$,
—NRCOR, —NRSOR, —$NRSO_2R$, OH, CN,
—$CO_2H$,
—R—OH, —O—R, —COOR,
—$CON(R)_2$, —CONROR,
—$SO_3H$, —R—S, —$SO_2N(R)_2$,
—S(O)R, —$S(O)_2R$, wherein each R is independently an aryl or aliphatic, optionally with substitution. Among hetero substituents containing R groups, preference is given to those materials having aryl and alkyl R groups as defined herein. Preferred hetero substituents are those listed above.

As used herein, the term "cycloheteroalkyl" refers to a stable heterocyclic non-aromatic ring and fused rings containing one or more heteroatoms independently selected from N, O and S. A fused heterocyclic ring system may include carbocyclic rings and need only include one heterocyclic ring. Examples of heterocyclic rings include, but are not limited to, piperazinyl, homopiperazinyl, piperidinyl and morpholinyl, and are shown in the following illustrative examples:

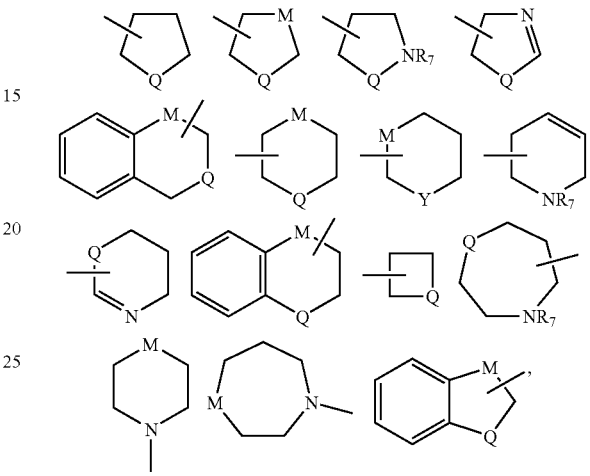

optionally substituted with one or more groups selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-$S(O)_2$— and aryl-$S(O)_2$—. Substituting groups include carbonyl or thiocarbonyl which provide, for example, lactam and urea derivatives. In the examples, M is $CR^7$, $NR^2$, O, or S; Q is O, $NR^2$ or S. $R^7$ and $R^8$ are independently selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-$S(O)_2$— and aryl-$S(O)_2$—.

"Dihydroxyphosphoryl" refers to the radical —$PO(OH)_2$.

"Substituted dihydroxyphosphoryl" includes those groups recited in the definition of "substituted" herein, and particularly refers to a dihydroxyphosphoryl radical wherein one or both of the hydroxyl groups are substituted. Suitable substituents are described in detail below.

"Aminohydroxyphosphoryl" refers to the radical —$PO(OH)NH_2$.

"Substituted aminohydroxyphosphoryl" includes those groups recited in the definition of "substituted" herein, and particularly refers to an aminohydroxyphosphoryl wherein the amino group is substituted with one or two substituents. Suitable substituents are described in detail below. In certain embodiments, the hydroxyl group can also be substituted.

"Thioalkoxy" refers to the group —SR where R is alkyl.

"Substituted thioalkoxy" includes those groups recited in the definition of "substituted" herein, and particularly refers to a thioalkoxy group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Sulfanyl" refers to the radical HS—. "Substituted sulfanyl" refers to a radical such as RS— wherein R is any substituent described herein.

"Sulfonyl" refers to the divalent radical —S(O$_2$)—. "Substituted sulfonyl" refers to a radical such as R—(O$_2$)S— wherein R is any substituent described herein. "Aminosulfonyl" or "Sulfonamide" refers to the radical H$_2$N(O$_2$)S—, and "substituted aminosulfonyl" "substituted sulfonamide" refers to a radical such as R$_2$N(O$_2$)S— wherein each R is independently any substituent described herein.

"Sulfone" refers to the group —SO$_2$R. In particular embodiments, R is selected from H, lower alkyl, alkyl, aryl and heteroaryl.

"Thioaryloxy" refers to the group —SR where R is aryl.

"Thioketo" refers to the group =S.

"Thiol" refers to the group —SH.

One having ordinary skill in the art of organic synthesis will recognize that the maximum number of heteroatoms in a stable, chemically feasible heterocyclic ring, whether it is aromatic or non aromatic, is determined by the size of the ring, the degree of unsaturation and the valence of the heteroatoms. In general, a heterocyclic ring may have one to four heteroatoms so long as the heteroaromatic ring is chemically feasible and stable.

"Pharmaceutically acceptable" means approved by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound of the invention that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like. The term "pharmaceutically acceptable cation" refers to a non toxic, acceptable cationic counter-ion of an acidic functional group. Such cations are exemplified by sodium, potassium, calcium, magnesium, ammonium, tetraalkylammonium cations, and the like.

"Pharmaceutically acceptable vehicle" refers to a diluent, adjuvant, excipient or carrier with which a compound of the invention is administered.

"Preventing" or "prevention" refers to a reduction in risk of acquiring a disease or disorder (i.e., causing at least one of the clinical symptoms of the disease not to develop in a subject that may be exposed to or predisposed to the disease but does not yet experience or display symptoms of the disease).

"Prodrugs" refers to compounds, including derivatives of the compounds of the invention,which have cleavable groups and become by solvolysis or under physiological conditions the compounds of the invention which are pharmaceutically active in vivo. Such examples include, but are not limited to, choline ester derivatives and the like, N-alkylmorpholine esters and the like.

"Solvate" refers to forms of the compound that are associated with a solvent, usually by a solvolysis reaction. Conventional solvents include water, ethanol, acetic acid and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates.

"Subject" includes humans. The terms "human," "patient" and "subject" are used interchangeably herein.

"Therapeutically effective amount" means the amount of a compound that, when administered to a subject for treating a disease, is sufficient to effect such treatment for the disease. The "therapeutically effective amount" can vary depending on the compound, the disease and its severity, and the age, weight, etc., of the subject to be treated.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

Other derivatives of the compounds of this invention have activity in both their acid and acid derivative forms, but in the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy)alkyl esters or ((alkoxycarbonyl)oxy)alkylesters. Preferred are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R— and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base. Representative enol-keto structures and equilibrium are illustrated below:

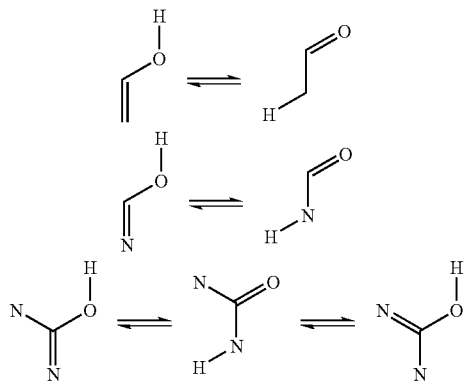

Tautomeric forms may be relevant to the attainment of the optimal chemical reactivity and biological activity of a compound of interest.

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

Compounds

As set forth earlier herein, the compounds of the present invention are useful for preventing and/or treating a broad range of conditions, among them, arthritis, Parkinson's disease, Alzheimer's disease, stroke, uveitis, asthma, myocardial infarction, the treatment and prophylaxis of pain syndromes (acute and chronic or neuropathic), traumatic brain injury, acute spinal cord injury, neurodegenerative disorders, alopecia (hair loss), inflammatory bowel disease and autoimmune disorders or conditions in mammals.

In order that the invention described herein may be more fully understood, the following structures representing compounds typical of the invention are set forth. It should be understood that these examples are for illustrative purposes only and are not to be construed as limiting this invention in any manner.

Accordingly, additional groups of particular compounds are provided. Thus, and as discussed earlier herein, suitable compounds capable of modifying ion channels in vivo, may be selected from those listed in Table 1, below, and may be prepared either as shown or in the form of a pharmaceutically acceptable salt, solvate or prodrug thereof; and stereoisomers and tautomers thereof. All such variants are contemplated herein and are within the scope of the present invention.

In certain aspects, the present invention provides prodrugs and derivatives of the compounds according to the formulae above. Prodrugs are derivatives of the compounds of the invention, which have cleavable groups and become by solvolysis or under physiological conditions the compounds of the invention, which are pharmaceutically active, in vivo. Such examples include, but are not limited to, choline ester derivatives and the like, N-alkylmorpholine esters and the like.

Other derivatives of the compounds of this invention have activity in both their acid and acid derivative forms, but the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy)alkyl esters or ((alkoxycarbonyl)oxy)alkylesters. Preferred are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

Assay Methods

Chronic Constriction Injury Model (CCI Model):

Male Sprague-Dawley rats (270-300 g; B. W., Charles River, Tsukuba, Japan) are used. The chronic constriction injury (CCI) operation is performed according to the method described by Bennett and Xie (Bennett, G. J. and Xie, Y. K. Pain, 33:87-107, 1988). Briefly, animals are anesthetized with sodium pentobarbital (64.8 mg/kg, i.p.) and the left common sciatic nerve is exposed at the level of the middle of the thigh by blunt dissection through the biceps femoris. A portion of the sciatic nerve proximal to its trifurcation is freed of adhering tissue and 4 ligatures (4-0 silk) are tied loosely around it with about 1 mm space. A sham operation is performed as same as CCI surgery except for sciatic nerve ligation. Two weeks after surgery, mechanical allodynia is evaluated by application of von Frey hairs (VFHs) to the plantar surface of the hind paw. The lowest amount of force of VFH required to elicit a response is recorded as the paw withdrawal threshold (PWT). VFH testing is performed at 0.5, 1 and 2 hr post-dosing. Experimental data are analyzed using Kruskal-Wallis test followed by Dunn's test for multiple comparisons or Mann-Whitney U-test for paired comparison.

Caco-2 Permeability

Caco-2 permeability is measured according to the method described in Shiyin Yee, Pharmaceutical Research, 763 (1997).

Caco-2 cells are grown on filter supports (Falcon HTS multiwell insert system) for 14 days. Culture medium is removed from both the apical and basolateral compartments and the monolayers are preincubated with pre-warmed 0.3 ml apical buffer and 1.0 ml basolateral buffer for 0.75 hour at 37° C. in a shaker water bath at 50 cycles/min. The apical buffer consists of Hanks Balanced Salt Solution, 25 mM D-glucose monohydrate, 20 mM MES Biological Buffer, 1.25 mM $CaCl_2$ and 0.5 mM $MgCl_2$ (pH 6.5). The basolateral buffer consists of Hanks Balanced Salt Solution, 25 mM D-glucose monohydrate, 20 mM HEPES Biological Buffer, 1.25 mM $CaCl_2$ and 0.5 mM MgCl2 (pH 7.4). At the end of the preincubation, the media is removed and test compound solution (10 µM) in buffer is added to the apical compartment. The inserts are moved to wells containing fresh basolateral buffer and incubated for 1 hr. Drug concentration in the buffer is measured by LC/MS analysis.

Flux rate (F, mass/time) is calculated from the slope of the cumulative appearance of substrate on the receiver side and apparent permeability coefficient (Papp) is calculated from the following equation:

$$Papp(cm/sec)=(F*VD)/(SA*MD)$$

where SA is surface area for transport (0.3 $cm^2$), VD is the donor volume (0.3 ml), MD is the total amount of drug on the donor side at t=0. All data represent the mean of 2 inserts. Monolayer integrity is determined by Lucifer Yellow transport.

Human Dofetilide Binding

Cell paste of HEK-293 cells expressing the HERG product can be suspended in 10-fold volume of 50 mM Tris buffer adjusted at pH 7.5 at 25° C. with 2 M HCl containing 1 mM $MgCl_2$, 10 mM KCl. The cells are homogenized using a Polytron homogenizer (at the maximum power for 20 seconds) and centrifuged at 48,000 g for 20 minutes at 4° C. The pellet is resuspended, homogenized and centrifuged once more in the same manner. The resultant supernatant is discarded and the final pellet is resuspended (10-fold volume of 50 mM Tris buffer) and homogenized at the maximum power for 20 seconds. The membrane homogenate is aliquoted and stored at −80° C. until use. An aliquot is used for protein concentration determination using a Protein Assay Rapid Kit and ARVO SX plate reader (Wallac). All the manipulation, stock solution and equipment are kept on ice at all times. For saturation assays, experiments are conducted in a total volume of 200 µl. Saturation is determined by incubating 20 µl of [3H]-dofetilide and 160 µl of membrane homogenates (20-30 µg protein per well) for 60 min at room temperature in the absence or presence of 10 µM dofetilide at final concentrations (20 µl) for total or nonspecific binding, respectively. All incubations are terminated by rapid vacuum filtration over polyetherimide (PEI) soaked glass fiber filter papers using Skatron cell harvester followed by two washes with 50 mM Tris buffer (pH 7.5 at 25° C.). Receptor-bound radioactivity is quantified by liquid scintillation counting using a Packard LS counter.

For the competition assay, compounds are diluted in 96 well polypropylene plates as 4-point dilutions in semi-log format. All dilutions are performed in DMSO first and then transferred into 50 mM Tris buffer (pH 7.5 at 25° C.) containing 1 mM $MgCl_2$, 10 mM KCl so that the final DMSO concentration becomes equal to 1%. Compounds are dispensed in triplicate in assay plates (4 µl). Total binding and nonspecific binding wells are set up in 6 wells as vehicle and 10 µM dofetilide at final concentration, respectively. The radioligand is prepared at 5.6× final concentration and this solution is added to each well (36 µl). The assay is initiated by addition of YSi poly-L-lysine Scintillation Proximity Assay (SPA) beads (50 µl, 1 mg/well) and membranes (110 µl, 20 µg/well). Incubation is continued for 60 min at room temperature. Plates are incubated for a further 3 hours at room temperature for beads to settle. Receptor-bound radioactivity is quantified by counting Wallac MicroBeta plate counter.

HERG Assay

HEK 293 cells which stably express the HERG potassium channel are used for electrophysiological study. The methodology for stable transfection of this channel in HEK cells can be found elsewhere (Z. Zhou et al., 1998, Biophysical Journal, 74, pp230-241). Before the day of experimentation, the cells are harvested from culture flasks and plated onto glass coverslips in a standard Minimum Essential Medium (MEM) medium with 10% Fetal Calf Serum (FCS). The plated cells are stored in an incubator at 37° C. maintained in an atmosphere of 95% $O_2$/5% $CO_2$. Cells are studied between 15-28 hrs after harvest.

HERG currents are studied using standard patch clamp techniques in the whole-cell mode. During the experiment the cells are superfused with a standard external solution of the following composition (mM); NaCl, 130; KCl, 4; $CaCl_2$, 2; $MgCl_2$, 1; Glucose, 10; HEPES, 5; pH 7.4 with NaOH. Whole-cell recordings are made using a patch clamp amplifier and patch pipettes which have a resistance of 1-3 MOhm when filled with the standard internal solution of the following composition (mM); KCl, 130; MgATP, 5; $MgCl_2$, 1.0; HEPES, 10; EGTA 5, pH 7.2 with KOH. Only those cells with access resistances below 15 MΩ and seal resistances >1 GΩ are accepted for further experimentation. Series resistance compensation is applied up to a maximum of 80%. No leak subtraction is done. However, acceptable access resistance depends on the size of the recorded currents and the level of series resistance compensation that can safely be used. Following the achievement of whole cell configuration and sufficient time for cell dialysis with pipette solution (>5 min), a standard voltage protocol is applied to the cell to evoke membrane currents. The voltage protocol is as follows. The membrane is depolarized from a holding potential of −80 mV to +40 mV for 1000 ms. This is followed by a descending voltage ramp (rate 0.5 mV msec−1) back to the holding potential. The voltage protocol is applied to a cell continuously throughout the experiment every 4 seconds (0.25 Hz). The amplitude of the peak current elicited around −40 mV during the ramp is measured. Once stable evoked current responses are obtained in the external solution, vehicle (0.5% DMSO in the standard external solution) is applied for 10-20 min by a peristalic pump. Provided there are minimal changes in the amplitude of the evoked current response in the vehicle control condition, the test compound of either 0.3, 1, 3, 10 mM is applied for a 10 min period. The 10 min period includes the time during which supplying solution is passing through the tube from solution reservoir to the recording chamber via the pump. Exposure time of cells to the compound solution is more than 5 min after the drug concentration in the chamber well reaches the intended concentration. There is a subsequent wash period of 10-20 min to assess reversibility. Finally, the cells are exposed to high dose of dofetilide (5 mM), a specific IKr blocker, to evaluate the insensitive endogenous current.

All experiments are performed at room temperature (23±1° C.). Evoked membrane currents are recorded on-line on a computer, filtered at 500-1 KHz (Bessel −3 dB) and sampled at 1-2 KHz using a patch clamp amplifier and specific data analyzing software. Peak current amplitude, which generally occurs at around −40 mV, is measured off line on the computer.

The arithmetic mean of the ten values of amplitude is calculated under vehicle control conditions and in the presence of drug. Percent decrease of IN in each experiment is obtained by the normalized current value using the following formula: IN=(1−ID/IC)×100, where ID is the mean current value in the presence of drug and IC is the mean current value under control conditions. Separate experiments are performed for each drug concentration or time-matched control, and the arithmetic mean in each experiment is defined as the result of the study.

Half-Life in Human Liver Microsomes (HLM)

Test compounds (1 μM) are incubated with 3.3 mM $MgCl_2$ and 0.78 mg/mL HLM (HL101) in 100 mM potassium phosphate buffer (pH 7.4) at 37° C. on the 96-deep well plate. The reaction mixture is split into two groups, a non-P450 and a P450 group. NADPH is only added to the reaction mixture of the P450 group. An aliquot of samples of the P450 group is collected at 0, 10, 30, and 60 min time points, where the 0 min time point indicates the time when NADPH is added into the reaction mixture of P450 group. An aliquot of samples of a non-P450 group is collected at −10 and 65 min time points. Collected aliquots are extracted with acetonitrile solution containing an internal standard. The precipitated protein is spun down in a centrifuge (2000 rpm, 15 min). The compound concentration in the supernatant is measured by LC/MS/MS system.

The half-life value is obtained by plotting the natural logarithm of the peak area ratio of compounds/internal standard versus time. The slope of the line of best fit through the points yields the rate of metabolism (k). This is converted to a half-life value using following equations:

Half-life=ln 2/k

Mono-Iodoacetate (MIA)-Induced OA Model

Male 6-weeks-old Sprague-Dawley (SD, Japan SLC or Charles River Japan) rats are anesthetized with pentobarbital. The injection site (knee) of MIA is shaved and cleaned with 70% ethanol. Twenty-five ml of MIA solution or saline is injected in the right knee joint using a 29 G needle. The effect of joint damage on the weight distribution through the right (damaged) and left (untreated) knee is assessed using an incapacitance tester (Linton Instrumentation, Norfolk, UK). The force exerted by each hind limb is measured in grams. The weight-bearing (WB) deficit is determined by a difference of weight loaded on each paw. Rats are trained to measure the WB once a week until 20 days post MIA-injection. Analgesic effects of compounds are measured at 21 days after the MIA injection. Before the compound administration, the "pre value" of WB deficit is measured. After the administration of compounds, attenuation of WB deficits is determined as analgesic effects.

Complete Freund's Adjuvant (CFA) Induced Thermal and Mechanical Hyperalgesia in Rats Thermal Hyperalgesia Male 6-week-old SD rats are used. Complete Freund's adjuvant (CFA, 300 mg of Mycobacterium Tuberculosis H37RA (Difco, Mich.) in 100 μL of liquid paraffin (Wako, Osaka, Japan)) is injected into the plantar surface of a hind paw of the rats. Two days after CFA-injection, thermal hyperalgesia is determined by method described previously (Hargreaves et al., 1988) using the plantar test apparatus (Ugo-Basil, Varese, Italy). Rats are adapted to the testing environment for at least 15 minutes prior to any stimulation. Radiant heat is applied to the plantar surface of a hind paw and paw withdrawal latencies (PWL, seconds) are determined. The intensity of radiant heat is adjusted to produce the stable PWL of 10 to 15 seconds. The test compound is administered in a volume of 0.5 mL per 100 g body weight. PWL are measured after 1, 3 or 5 hours after drug administration.

Mechanical Hyperalgesia

Male 4-week-old SD rats are used. CFA (300 mg of Mycobacterium Tuberculosis H37RA (Difco, MI) in 100 μL of liquid paraffin (Wako, Osaka, Japan)) is injected into the plantar surface of a hind paw of the rats. Two days after CFA-injection, mechanical hyperalgesia is tested by measuring paw withdrawal threshold (PWT, grams) to pressure using the analgesy-Meter (Ugo-Basile, Varese, Italy). The animals are gently restrained, and steadily increasing pressure is applied to the dorsal surface of a hind paw via a plastic tip. The pressure required to elicit paw withdrawal is determined. The test compound is administered in a volume of 0.5 mL per 100 g body weight. PWT are measured after 1, 3 or 5 hours after drug administration.

Acid Stimulation Assay:

The Acid-induced changes in the intracellular calcium concentration may be monitored using FDSS 6000 (Hamamatsu Photonics, Japan), a fluorometric imaging system. The cell suspension in resting buffer (HBSS supplemented with 10 mM HEPES, pH 7.4) is pre-incubated with varying concentrations of the test compounds or resting buffer (buffer control) for 15 minutes at room temperature under dark conditions. The cells are automatically added the stimulating solution (HBSS supplemented with MES, final assay buffer pH5.8) by the FDSS 6000. The $IC_{50}$ values of VR1 antagonists are determined from the half of the increase demonstrated by buffer control samples after acidic stimulation.

Pharmacokinetic Evaluation of Compounds Following Intravenous and Oral Administration in Rats.

Male Sprague-Dawley rats are acclimatized for at least 24 hours prior to experiment initiation. During acclimation period, all animals receive food and water ad libitum. However, food but not water is removed from the animal's cages at least 12 hours before initiation of the experiment. During the first 3 hours of experimentation, the animals receive only water ad libitum. At least three animal each are tested for intravenous and oral dosage. For intravenous formulation, compounds are dissolved (0.25 to 1 mg/mL) in a mixture of 3% dimethyl sulfoxide, 40% PEG 400 and the rest percentage of 40% Captisol in water (w/v). For oral formulation, compounds of this invention are dissolved (2 mg/mL) in a mixture of 5% of 10% Tween 80 in water (v/v) and 95% of 0.5% methyl cellulose in water (w/v). The animals are weighed before dosing. The determined body weight is used to calculate the dose volume for each animal.

Dose volume (mL/kg)=1 mg/kg/formulation concentration (mg/mL)

In instances where the formulation concentrations are less than 0.5 mg/mL, the dosing volume is about 2 mL/kg. PO rats are typically dosed through oral gavage at 2.5 mL/kg to achieve a dose level of 5 mg/kg. For IV dosing, blood samples are collected (using a pre-heparinized syringe) via the jugular vein catheter at 2, 5, 15, 30, 60, 120, 180, 300, 480, and 1440 minutes post dosing. For PO dosing, blood samples are collected (using a pre-heparinized syringe) via the jugular vein catheter before dosing and at 5, 15, 30, 60, 120, 180, 300, 480, and 1440 minutes post dosing. About 250 uL of blood is obtained at each time point from the animal. Equal volumes of 0.9% normal saline are replaced to prevent dehydration. The whole blood samples are maintained on ice until centrifugation. Blood samples are then centrifuged at 14,000 rpm for 10 minutes at 4° C. and the upper plasma layer transferred into a clean vial and stored at −80° C. The resulting plasma samples are then analyzed by liquid chromatography-tandem mass spectrometry. Following the measurement of plasma samples and dosing solutions, plasma concentration-time curve is plotted. Plasma exposure is calculated as the area under the concentration-time curve extrapolated to time infinite ($AUC_{inf}$). The $AUC_{inf}$ is averaged and the oral bioavailability (% F) for individual animal is calculated as:

AUCinf(IV, average)/AUCinf (PO), normalized to their respective dose levels.

The % F is reported as the mean % F of all oral dosed animals.

Calcium Imaging Assay

VR1 protein is a heat-gated cation channel that exchanges approximately ten calcium ions for every sodium ion resulting in neuronal membrane depolarization and elevated intracellular calcium levels. Therefore the functional activity of compounds at the VR1 receptor may be determined by measuring changes in intracellular calcium levels in neurons such as the dorsal root ganglion.

DRG neurons are grown on PDL coated 96-well black-walled plates, in the presence of DMEM medium containing 5% Penstrep, 5% Glutamax, 200 µg/ml hygromycin, 5 µg/ml blasticide and 10% heat inactivated FBS. Prior to assay, cells are loaded with 5 µg/ml Fura2 in normal saline solution at 37° C. for 40 minutes. Cells are then washed with normal saline to remove dye before commencement of the experiment.

The plated neurons are transferred into a chamber on the stage of a Nikon eclipse TE300 microscope after which neurons are allowed to attain a stable fluorescence for about 10 minutes before beginning the experiment. The assay consists of two stages, a pretreatment phase followed by a treatment phase. First, a solution of the test compound is added from a multivalve perfusion system to the cells for 1 minute (pretreatment). Immediately following, capsaicin (250 nM) is added in the presence of the test compound (treatment) for a specific period between 20 and 60 seconds.

Fura2 is excited at 340 and 380 nM to indicate relative calcium ion concentration. Changes in wavelength measurements are made throughout the course of the experiment. The fluorescence ratio is calculated by dividing fluorescence measured at 340 nM by that at 380 nM. Data are collected using Intelligent Imaging's Slidebook software. All compounds that inhibit capsaicin induced calcium influx greater than 75% are considered positives.

Whole-Cell Patch Clamp Electrophysiology

Dorsal root ganglion (DRG) neurons may be recovered from either neonatal or adult rats and plated onto poly-D-lysine coated glass coverslips. The plated neurons are transferred into a chamber to allow drug solutions to be added to the cells using a computer-controlled solenoid-valve based perfusion system. The cells are imaged using standard DIC optics. Cells are patched using finely-pulled glass electrodes. Voltage-clamp electrophysiology experiments are carried out using an Axon Instruments Multiclamp amplified controlled by pCLAMP8 software.

The cells are placed into a whole-cell voltage clamp and held at a voltage of −80 mV while monitoring the membrane current in gap-free recording mode. 500 nM capsaicin is added for 30 seconds as a control. Test compounds at various concentrations are added to the cells for 1 minute prior to a 30 second capsaicin application. Differences between control experiments and drug positive capsaicin experiments are used to determine the efficacy of each test compound. All compounds that inhibit capsaicin induced current greater than 50% are considered positives.

Pharmaceutical Compositions

When employed as pharmaceuticals, the amide compounds of this invention are typically administered in the form of a pharmaceutical composition. Such compositions can be prepared in a manner well known in the pharmaceutical art and comprise at least one active compound.

Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of this invention can be administered by a variety of routes including by way of non limiting example, oral, rectal, transdermal, subcutaneous, intravenous, intramuscular and intranasal. Depending upon the intended route of delivery, the compounds of this invention are preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the furansulfonic acid compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

The compounds of this invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pa., which is incorporated herein by reference.

The compounds of this invention can also be administered in sustained release forms or from sustained release drug delivery systems. A description of representative sustained release materials can be found in *Remington's Pharmaceutical Sciences.*

The following formulation examples illustrate representative pharmaceutical compositions of this invention. The present invention, however, is not limited to the following pharmaceutical compositions.

Formulation 1—Tablets

A compound of formula I is admixed as a dry powder with a dry gelatin binder in an approximate 1:2 weight ratio. A minor amount of magnesium stearate is added as a lubricant. The mixture is formed into 240-270 mg tablets (80-90 mg of active compound per tablet) in a tablet press.

Formulation 2—Capsules

A compound of formula I is admixed as a dry powder with a starch diluent in an approximate 1:1 weight ratio. The mixture is filled into 250 mg capsules (125 mg of active compound per capsule).

Formulation 3—Liquid

A compound of formula I (125 mg), sucrose (1.75 g) and xanthan gum (4 mg) are blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets

The compound of formula I is admixed as a dry powder with a dry gelatin binder in an approximate 1:2 weight ratio. A minor amount of magnesium stearate is added as a lubricant. The mixture is formed into 450-900 mg tablets (150-300 mg of active compound) in a tablet press.

Formulation 5—Injection

The compound of formula I is dissolved or suspended in a buffered sterile saline injectable aqueous medium to a concentration of approximately 5 mg/ml.

Formulation 6—Topical

Stearyl alcohol (250 g) and a white petrolatum (250 g) are melted at about 75° C. and then a mixture of a compound of formula I (50 g) methylparaben (0.25 g), propylparaben (0.15 g), sodium lauryl sulfate (10 g), and propylene glycol (120 g) dissolved in water (about 370 g) is added and the resulting mixture is stirred until it congeals.

Methods of Treatment

The present compounds are used as therapeutic agents for the treatment of conditions in mammals. Accordingly, the compounds and pharmaceutical compositions of this invention find use as therapeutics for preventing and/or treating neurodegenerative, autoimmune and inflammatory conditions in mammals including humans.

In a method of treatment aspect, this invention provides a method of treating a mammal susceptible to or afflicted with a condition associated with arthritis, uveitis, asthma, myocardial infarction, traumatic brain injury, acute spinal cord injury, alopecia (hair loss), inflammatory bowel disease and autoimmune disorders, which method comprises administering an effective amount of one or more of the pharmaceutical compositions just described.

In yet another method of treatment aspect, this invention provides a method of treating a mammal susceptible to or afflicted with a condition that gives rise to pain responses or that relates to imbalances in the maintenance of basal activity of sensory nerves. Compounds have use as analgesics for the treatment of pain of various geneses or etiology, for example acute, inflammatory pain (such as pain associated with osteoarthritis and rheumatoid arthritis); various neuropathic pain syndromes (such as post-herpetic neuralgia, trigeminal neuralgia, reflex sympathetic dystrophy, diabetic neuropathy, Guillian Barre syndrome, fibromyalgia, phantom limb pain, post-masectomy pain, peripheral neuropathy, HIV neuropathy, and chemotherapy-induced and other iatrogenic neuropathies); visceral pain, (such as that associated with gastroesophageal reflex disease, irritable bowel syndrome, inflammatory bowel disease, pancreatitis, and various gynecological and urological disorders), dental pain and headache (such as migraine, cluster headache and tension headache).

In additional method of treatment aspects, this invention provides methods of treating a mammal susceptible to or afflicted with neurodegenerative diseases and disorders such as, for example Parkinson's disease, Alzheimer's disease and multiple sclerosis; diseases and disorders which are mediated by or result in neuroinflammation such as, for example traumatic brain injury, stroke, and encephalitis; centrally-mediated neuropsychiatric diseases and disorders such as, for example depression mania, bipolar disease, anxiety, schizophrenia, eating disorders, sleep disorders and cognition disorders; epilepsy and seizure disorders; prostate, bladder and bowel dysfunction such as, for example urinary incontinence, urinary hesitancy, rectal hypersensitivity, fecal incontinence, benign prostatic hypertrophy and inflammatory bowel disease; respiratory and airway disease and disorders such as, for example, allergic rhinitis, asthma and reactive airway disease and chronic obstructive pulmonary disease; diseases and disorders which are mediated by or result in inflammation such as, for example rheumatoid arthritis and osteoarthritis, myocardial infarction, various autoimmune diseases and disorders, uveitis and atherosclerosis; itch/pruritus such as, for example psoriasis; alopecia (hair loss); obesity; lipid disorders; cancer; blood pressure; spinal cord injury; and renal disorders method comprises administering an effective condition-treating or condition-preventing amount of one or more of the pharmaceutical compositions just described.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prevention and/or treatment of long-term conditions, such as neurodegenerative and autoimmune conditions, the regimen for treatment usually stretches over many months or years so oral dosing is preferred for patient convenience and tolerance. With oral dosing, one to five and especially two to four and typically three oral doses per day are representative regimens. Using these dosing patterns, each dose provides from about 0.01 to about 20 mg/kg of the compound or its derivative, with preferred doses each providing from about 0.1 to about 10 mg/kg and especially about 1 to about 5 mg/kg.

Transdermal doses are generally selected to provide similar or lower blood levels than are achieved using injection doses.

When used to prevent the onset of a neurodegenerative, autoimmune or inflammatory condition, the compounds or their derivatives of this invention will be administered to a patient at risk for developing the condition, typically on the advice and under the supervision of a physician, at the dosage levels described above. Patients at risk for developing a particular condition generally include those that have a family history of the condition, or those who have been identified by genetic testing or screening to be particularly susceptible to developing the condition.

The compounds of this invention can be administered as the sole active agent or they can be administered in combination with other agents, including other active derivatives. A VR1 antagonist may be usefully combined with another pharmacologically active compound, or with two or more other pharmacologically active compounds, particularly in the treatment of pain. For example, a VR1 antagonist, particularly a compound of formula (I), or a pharmaceutically acceptable salt or solvate thereof, as defined above, may be administered simultaneously, sequentially or separately in combination with one or more agents selected from:

an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;

a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;

a barbiturate sedative, e.g. amobarbital, aprobarbital, butabarbital, butabital, mephobarbital, metharbital, methohexital, pentobarbital, phenobartital, secobarbital, talbutal, theamylal or thiopental;

a benzodiazepine having a sedative action, e.g. chlordiazepoxide, clorazepate, diazepam, flurazepam, lorazepam, oxazepam, temazepam or triazolam;

an H1 antagonist having a sedative action, e.g. diphenhydramine, pyrilamine, promethazine, chlorpheniramine or chlorcyclizine;

a sedative such as glutethimide, meprobamate, methaqualone or dichloralphenazone;

a skeletal muscle relaxant, e.g. baclofen, carisoprodol, chlorzoxazone, cyclobenzaprine, methocarbamol or orphrenadine;

an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex®, a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-dihydro-2(1H)-quinolinone;

an alpha-adrenergic, e.g. doxazosin, tamsulosin, clonidine, guanfacine, dexmetatomidine, modafinil, or 4-amino-6,7-dimethoxy-2-(5-methane-sulfonamido-1,2,3,4-tetrahydroisoquinol-2-yl)-5-(2-pyridyl)quinazoline;

a tricyclic antidepressant, e.g. desipramine, imipramine, amitriptyline or nortriptyline;

an anticonvulsant, e.g. carbamazepine, lamotrigine, topiramate or valproate;

a tachykinin (NK) antagonist, particularly an NK-3, NK-2 or NK-1 antagonist, e.g. (aR,9R)-7-[3,5-bis(trifluoromethyl) benzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3R)-2-[(1R)-1-[3,5-bis (trifluoromethyl)phenyl]ethoxy-3-(4-fluorophenyl)-4-morpholinyl]-methyl]-1,2-dihydro-3H-1,2,4-triazol-3- one (MK-869), aprepitant, lanepitant, dapitant or 3-[[2-methoxy-5-(trifluoromethoxy)phenyl]-methylamino]-2-phenylpiperidine (2S,3S);

a muscarinic antagonist, e.g oxybutynin, tolterodine, propiverine, tropsium chloride, darifenacin, solifenacin, temiverine and ipratropium;

a COX-2 selective inhibitor, e.g. celecoxib, rofecoxib, parecoxib, valdecoxib, deracoxib, etoricoxib, or lumiracoxib;

a coal-tar analgesic, in particular paracetamol;

a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion® or sarizotan;

a beta-adrenergic such as propranolol;

a local anaesthetic such as mexiletine;

a corticosteroid such as dexamethasone;

a 5-HT receptor agonist or antagonist, particularly a 5-HT1B/1D agonist such as eletriptan, sumatriptan, naratriptan, zolmitriptan or rizatriptan;

a 5-HT2A receptor antagonist such as R(+)-alpha-(2,3-dimethoxy-phenyl)-1-[2-(4-fluorophenylethyl)]-4-piperidinemethanol (MDL-100907);

a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;

Tramadol®;

a PDEV inhibitor, such as 5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)-pyrazino[2',1':6,1]-pyrido[3,4-b]indole-1,4-dione (IC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl)pyrrolidin-1-yl]-N-(pyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;

an alpha-2-delta ligand such as gabapentin, pregabalin, 3-methylgabapentin, (1a,3a,5a)(3-amino-methyl-bicyclo[3.2.0]hept-3-yl)-acetic acid, (3S,5R)-3_aminomethyl-5_methyl-heptanoic acid, (3S,5R)-3_amino-5_methyl-heptanoic acid, (3S,5R)-3_amino-5_methyl-octanoic acid, (2S,4S)-4-(3-chlorophenoxy)proline, (2S,4S)-4-(3-fluorobenzyl)-proline, [(1R,5R,6S)-6-(aminomethyl)bicyclo[3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (3S,5R)-3_aminomethyl-5_methyl-octanoic acid, (3S,5R)-3_amino-5_methyl-nonanoic acid, (3S,5R)-3_amino-5_methyl-octanoic acid, (3R,4R,5R)-3-amino-4,5-dimethyl-heptanoic acid and (3R,4R,5R)-3-amino-4,5-dimethyl-octanoic acid;

a cannabinoid;

a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;

a noradrenaline (norepinephrine) reuptake inhibitor, such as maprotiline, lofepramine, mirtazepine, oxaprotiline, fezolamine, tomoxetine, mianserin, buprorion, buproprion metabolite hydroxybuproprion, nomifensine and viloxazine (Vivalan®), especially a selective noradrenaline reuptake inhibitor such as reboxetine, in particular (S,S)-reboxetine;

a dual serotonin-noradrenaline reuptake inhibitor, such as venlafaxine, venlafaxine metabolite O-desmethylvenlafaxine, clomipramine, clomipramine metabolite desmethylclomipramine, duloxetine, milnacipran and imipramine;

an inducible nitric oxide synthase (iNOS) inhibitor such as S-[2-[(1-iminoethyl)amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl)amino]-5-heptenoic acid, 2-[[(1R,3S)-3-amino-4-hydroxy-1-(5-thiazolyl)-butyl]thio]-5-chloro-3-pyridinecarbonitrile; 2-[[(1R,3S)-3-amino-4-hydroxy-1-(5-thiazolyl)butyl]thio]-4-chlorobenzonitrile, (2S,4R)-2-amino-4-[[2-chloro-5-(trifluoromethyl)phenyl]thio]-5-thiazolebutanol, 2-[[(1R,3S)-3-amino-4-hydroxy-1-(5-thiazolyl)butyl]thio]-6-(trifluoromethyl)-3 pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino)ethyl]phenyl]thiophene-2-carboxamidine, or guanidinoethyldisulfide;

an acetylcholinesterase inhibitor such as donepezil;

a prostaglandin E2 subtype 4 (EP4) antagonist such as N-[({2-[4-(2-ethyl-4,6-dimethyl-1H-imidazo[4,5-c]pyridin-1-yl)phenyl]ethyl}amino)-carbonyl]-4-methylbenzenesulfonamide or 4-[(1S)-1-({[5-chloro-2-(3-fluorophenoxy)pyridin-3-yl]carbonyl}amino)ethyl]benzoic acid;

a leukotriene B4 antagonist; such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870;

a 5-lipoxygenase inhibitor, such as zileuton, 6-[(3-fluoro-5-[4-methoxy-3,4,5,6-tetrahydro-2H-pyran-4-yl])phenoxymethyl]-1-methyl-2-quinolone (ZD-2138), or 2,3,5-trimethyl-6-(3-pyridylmethyl),1,4-benzoquinone (CV-6504);

a sodium channel blocker, such as lidocaine;

a 5-HT3 antagonist, such as ondansetron;

and the pharmaceutically acceptable salts and solvates thereof.

In as much as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions.

Preparation of the Compounds

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The target compounds are synthesized by known reactions outlined in the following schemes. The products are isolated and purified by known standard procedures. Such procedures include (but are not limited to) recrystallization, column chromatography or HPLC.

In this specification, especially in "General Synthesis" and "Examples", the following abbreviations can be used:

DCM dichloromethane
DME 1,2-dimethoxyethane, dimethoxyethane
DMF N,N-dimethylformamide
DMSO dimethyl sulfoxide
EDC 1-ethyl-3-(3'-dimethylaminopropyl)carbodiimide hydrogen chloride)
EtOAc ethyl acetate
EtOH ethanol
HOBt 1-hydroxybenzotriazole
MeOH methanol
THF tetrahydrofuran
TFA trifluoroacetic acid Preparation of Acid Building Blocks Preparation of Substituted Benzoic Acids Intermediate 1

Preparation of 4-cyclopropyl-2-methylbenzoic acid

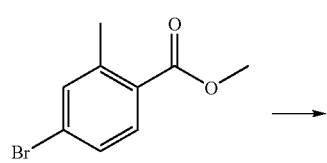

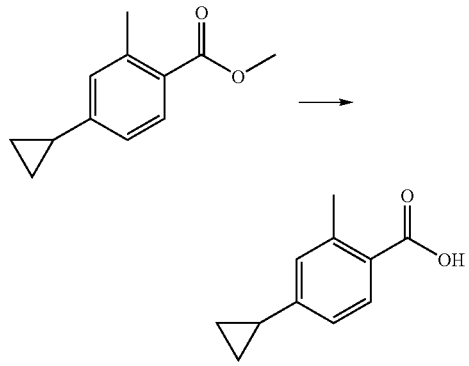

Methyl 4-cyclopropyl-2-methylbenzoate. (general procedure from *Tetrahedron Letters* 2002, 43, 6987-6990 was used)

Methyl 4-bromo-2-methylbenzoate (230 mg, 1.0 mmol), cyclopropyl boronic acid (112 mg, 1.3 mmol), potassium phosphate (750 mg, 3.5 mmol), tricyclohexylphosphine (28 mg, 0.1 mmol) and palladium(II) acetate (11 mg, 0.05 mmol) were combined in a sealed tube under nitrogen, then toluene (5 mL) and $H_2O$ (220 µL) were added in one portion. The mixture was sealed, heated to 100° C. and stirred overnight. After allowing to cool, the mixture was poured in to EtOAc (30 mL) and $H_2O$ (50 mL). The aqueous and organic layers were partitioned and the aqueous was extracted with EtOAc (2×20 mL). The combined organic extracts were washed with brine (1×30 mL), dried ($Na_2SO_4$), filtered and the filtrate concentrated under vacuum to leave a crude oil. The oil was purified by preparative thin-layer chromatography to give the product (130 mg, 68%) as an oil. (it should be noted that in our hands the starting bromide and product in this reaction have identical $R_f$ values when analysed by thin-layer chromatography).

$^1$H NMR (CDCl$_3$; 400 MHz) δ 7.84 (1H, d), 6.92-6.88 (2H, m), 3.85 (3H, s), 2.57 (3H, s), 1.91-1.84 (1H, m), 1.03-0.99 (2H, m), 0.77-0.72 (2H, m).

4-Cyclopropyl-2-methylbenzoic acid

A solution of lithium hydroxide (90 mg, 1.97 mmol) in $H_2O$ (1 mL) was added in one portion to a stirred solution of methyl 4-cyclopropyl-2-methylbenzoate (125 mg, 0.66 mmol) in THF (2 mL) and MeOH (2 mL). The mixture was stirred at room temperature for 30 min then at 50° C. for 2 hours. A further aliquot of lithium hydroxide (90 mg) in $H_2O$ (1 mL) and MeOH (1 mL) was added, and the mixture was stirred at 50° C. overnight. The organics were removed under vacuum and $H_2O$ (20 mL) was added. The mixture was adjusted to pH 4-5 by the use of 1N HCl (a precipitate emerges) and then extracted with EtOAc (2×20 mL). The combined organic extracts were dried ($Na_2SO_4$), filtered and the filtrate concentrated under vacuum to give the product (110 mg, 95%) as a solid. $^1$H NMR (CDCl$_3$; 400 MHz) δ 7.98 (1H, d), 6.96-6.92 (2H, m), 2.63 (3H, s), 1.94-1.87 (1H, m), 1.07-1.01 (2H, m), 0.80-0.76 (2H, m).

Intermediate 2

Preparation of (2,2-dichlorocyclopropyl)benzoic acid

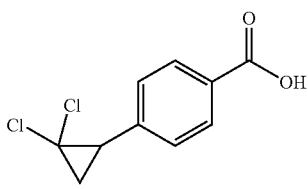

This compound was purchased from a commercial source.

Intermediate 3

Preparation of cis- and trans-2-methyl-4-(2-(trifluoromethyl)cyclopropyl)benzoic acid Part I. Preparation of cis- and trans-methyl 2-methyl-4-(2-(trifluoromethyl)-cyclopropyl)benzoate (each cis- and trans-isomer is a racemic mixture and consists of two enantiomers)

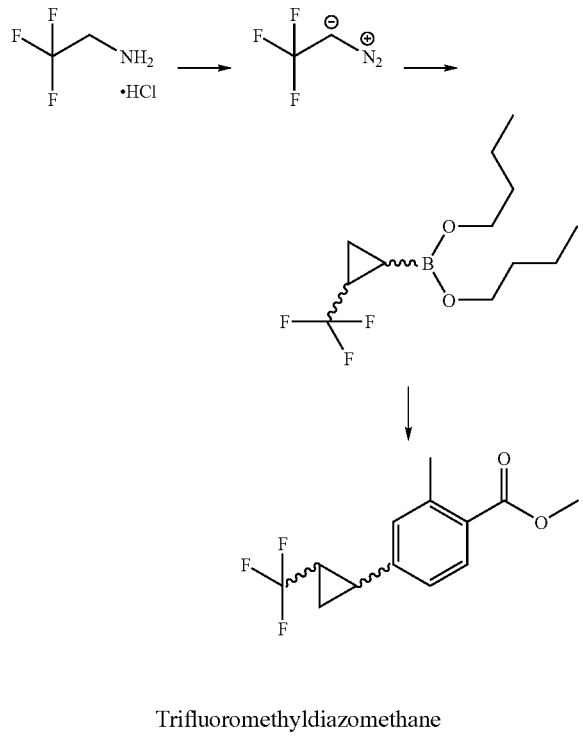

Trifluoromethyldiazomethane

CARE: PRODUCT IS POTENTIALLY EXPLOSIVE. A BLAST SHIELD AND METAL CONTAINER WERE EMPLOYED IN THIS REACTION TO ENSURE ADEQUATE PROTECTION—although the reaction was performed in a round bottom flask and separated in a separating funnel the apparatus was inspected prior to the reaction to select glassware with the fewest scratches or cracks (method similar to J. Am. Chem. Soc. 1943, 65, 1458-1460). Sodium nitrite (4.6 g, 66 mmol) in water (10 mL) was added in one portion to a stirred solution of 2,2,2-trifluoroethylamine hydrochloride (8.1 g, 60 mmol) in water (25 mL) and ether (45 mL) at 0° C. The reaction vessel was sealed with a teflon topper and the mixture stirred from 0° C. to rt and stirred at rt for approximately 3 hours. The mixture was then partitioned in a separating funnel and the ether layer containing the product used directly in the next step without further purification. The yield of the product was assumed to be approximately 50% based on literature (=3.32 g).

cis- and trans-dibutyl 2-(trifluoromethyl)cyclopropylboronate 2,2,2-Trifluorodiazomethane (3.2 g, 29 mmol) in $Et_2O$ (45 mL) was added dropwise over 30-40 min to a stirred suspension of palladium(II) acetate (40 mg, 0.2 mmol) and vinyl boronic acid diutyl ester (3.2 g, 17 mmol) in $Et_2O$ (30 mL) at room temperature. After approximately 15 min of addition a further aliquot of palladium(II) acetate (40 mg) was added to the mixture. After complete addition of the 2,2,2-trifluoromethyldiazomethane, more palladium(II) acetate (ca. 20 mg) was added to ensure complete decomposition of the diazo compound. The mixture was stirred at rt for a further 15 min (Pd-black seems to precipitate by this time), then filtered through celite and the filter cake washed with $Et_2O$ (2×15 mL). The filtrate was concentrated under vacuum to leave a crude oil (traces of Pd-black are also apparent) which was used directly in the next step. Yield assumed quantitative=4.6 g.

cis- and trans-methyl 2-methyl-4-(2-(trifluoromethyl)cyclopropyl)benzoate

A mixture of methyl 4-bromo-2-methylbenzoate (2.10 g, 9.2 mmol) and dibutyl 2-(trifluoromethyl)cyclopropylboronate (2.4 g, 9.0 mmol) in toluene (48 mL) in a sealed tube was sparged with nitrogen for 10 min. Potassium phosphate (6.7 g, 32 mmol) then palladium(II) acetate (80 mg, 0.4 mmol) and tricyclohexylphosphine (200 mg, 0.9 mmol) were added to the mixture in one portion under nitrogen, followed by water (1.92 mL). The mixture was sealed under nitrogen and heated to 120° C. and stirred overnight. After allowing to cool to room temperature the mixture was poured in to EtOAc (100 mL) and water (100 mL). The aqueous and organic layers were partitioned and the aqueous extracted with EtOAc (1×50 mL). The combined organic extracts were washed with brine (1×50 mL), dried ($Na_2SO_4$), filtered and the filtrate concentrated under vacuum to leave a crude oil containing the isomeric products.

Part II. Separation of cis- and trans-methyl 2-methyl-4-(2-(trifluoromethyl)-cyclopropyl)benzoate Crude oil from the synthesis of cis- and trans-methyl 2-methyl-4-(2-(trifluoromethyl)cyclopropyl)benzoate above was purified by high-performance liquid chromatomatography (column details: Phenomenex Gemini C18 10 μM. 250×21.2 mm+guard) using an acetonitrile/water gradient as eleuent (20 to 100%; see below for gradient timecourse) with a flow rate of 20 mL/min to give;

Geometrical Isomer A (More Polar Isomer)

It is not known whether geometrical isomer A is the pure cis- or pure trans-geometrical isomer. It should also be noted that geometrical isomer A is a racemic mixture containing two enantiomers. $^1$H NMR (CDCl$_3$; 400 MHz) δ 7.87 (1H, d), 7.20-7.15 (2H, m), 3.88 (3H, s), 2.59 (3H, s), 2.49-2.42 (1H, m), 1.97-1.87 (1H, m), 1.48-1.43 (1H, m), 1.34-1.28 (1H, m). $^{19}$F NMR (CDCl$_3$; 400 MHz) −61.25.

Geometrical Isomer B (Least Polar Isomer)

It is not known whether geometrical isomer B is the pure trans- or pure cis-geometrical isomer. It should also be noted that geometrical isomer B is a racemic mixture containing two enantiomers. $^1$H NMR (CDCl$_3$; 400 MHz) δ 7.87 (1H, d), 6.99-6.94 (2H, m), 3.88 (3H, s), 2.59 (3H, s), 2.37-2.31 (1H, m), 1.90-1.81 (1H, m), 1.45-1.39 (1H, m), 1.24-1.18 (1H, m). $^{19}$F NMR (CDCl$_3$; 400 MHz) −66.88.

| Gradient timecourse | |
|---|---|
| Time (min) | % Acetonitrile |
| 0 | 20 |
| 1 | 20 |
| 1.5 | 65 |
| 15 | 85 |
| 15.1 | 100 |
| 19 | 100 |
| 19.5 | 20 |
| 21 | stop |

Part III. Hydrolysis of cis-methyl 2-methyl-4-(2-(trifluoromethyl)cyclopropyl)benzoate and trans-methyl 2-methyl-4-(2-(trifluoromethyl)cyclopropyl)benzoate (each cis- and trans-isomer is a racemic mixture containing two anantiomers)

Geometrical Isomer B from HPLC Separation.

A solution of lithium hydroxide (89 mg, 1.8 mmol) in H$_2$O (1 mL) was added to a mixture of methyl 2-methyl-4-(2-(trifluoromethyl)cyclopropyl)benzoate (geometrical isomer B from HPLC separation; 160 mg, 0.62 mmol), THF (2 mL) and MeOH (2 mL). The mixture was stirred at rt for 3 hours then heated to 45° C. and stirred overnight. The organics were then removed under vacuum and H$_2$O (20 mL) was added. The aqueous layer was acidified to pH 3-4 using 1N HCl (a precipitate emerges), then extracted with EtOAc (2×30 mL). The combined organic extracts were washed with brine (1×20 mL), dried (Na$_2$SO$_4$), filtered and the filtrate concentrated under vacuum to leave the product as a solid. The yield was assumed quantitative=150 mg. $^1$H NMR (CDCl$_3$; 400 MHz) δ 11.68 (1H, br. s), 8.03 (1H, d), 7.04-6.98 (2H, m), 2.64 (3H, s), 2.39-2.34 (1H, m), 1.93-1.83 (1H, m), 1.47-1.41 (1H, m), 1.26-1.20 (1H, m). $^{19}$F NMR (CDCl$_3$; 400 MHz) −66.90.

It should be noted 2-methyl-4-(2-(trifluoromethyl)cyclopropyl)benzoic acid geometrical isomer B is a racemic mixture and contains two enantiomers.

Geometrical Isomer A from HPLC Separation.

The above method for hydrolysis of geometrical isomer B was followed, except the mixture was heated to 45° C. directly after addition of the lithium hydroxide solution. The product (110 mg, 71%) was obtained as a solid. $^1$H NMR (CDCl$_3$; 400 MHz) δ 11.55 (1H, br. s), 8.01 (1H, d), 7.24-7.19 (2H, m), 2.64 (3H, s), 2.51-2.44 (1H, m), 1.99-1.87 (1H, m), 1.50-1.45 (1H, m), 1.36-1.30 (1H, m). $^{19}$F NMR (CDCl$_3$; 400 MHz) −61.25.

It should be noted 2-methyl-4-(2-(trifluoromethyl)cyclopropyl)benzoic acid geometrical isomer A is a racemic mixture and contains two enantiomers.

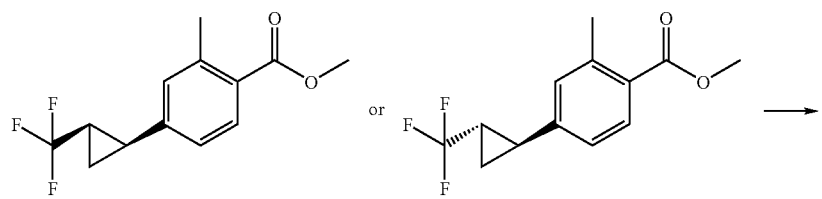

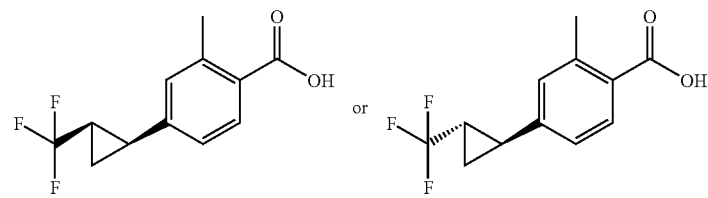

Preparation of Amine Building Blocks

Intermediate 4

Preparation of 2-((cyclopropylmethoxy)methyl)-2,3-dihydrobenzo[b][1,4]dioxin-6-amine

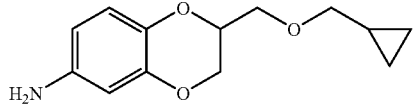

2-((cyclopropylmethoxy)methyl)-2,3-dihydro-6-nitrobenzo[b][1,4]dioxine (2,3-dihydro-6-nitrobenzo[b][1,4]dioxin-2-yl)methanol (500 mg, 0.002 mol) and sodium hydride (0.28 g, 0.0070 mol) were placed in a flask under nitrogen. The flask was placed in an ice bath and 25 mL DMF was added. The reaction was stirred at 0° C. for 10 minutes and then (chloromethyl)cyclopropane (440 µL, 0.0048 mol) was added. The mixture was warmed to room temp over 20 min then tetra-N-butylammonium bromide (1.53 g, 0.00475 mol) was added to the mixture and the reaction was stirred at room temperature overnight. The reaction was partitioned between EtOAc and water. The organic layer was separated, washed with brine, dried ($Na_2SO_4$), filtered and the filtrate was concentrated under vacuum to an oil. The oil was purified by column chromatography on silica gel using EtOAc/hexanes (10%) as eluent to give a yellow solid (0.33 g, 50%) as a solid. m/z=266 (M+1).

2-((cyclopropylmethoxy)methyl)-2,3-dihydrobenzo[b][1,4]dioxin-6-amine 2-((cyclopropylmethoxy)methyl)-2,3-dihydro-6-nitrobenzo[b][1,4]dioxine (0.33 g, 0.0012 mol) was dissolved in 20 mL dioxane. Sodium dithionite (2.2 g, 0.013 mol was suspended in water (4 mL) and $NH_4OH$ (2 mL) and then added to the dioxane solution. The reaction was stirred at room temp for 6 hrs. The mixture was filtered through a filter paper and the filtrate concentrated under vacuum to a white solid. The solid was suspended in 10% EtOAc/hexanes and filtered. The filtrate was concentrated to a white solid and used for the next reaction without further purification. Yield of the title compound is 0.29 g (98%). m/z=235.8 (M+1).

Intermediate 5

Preparation of 1-methyl-1,2,3,4-tetrahydroquinolin-7-ylamine

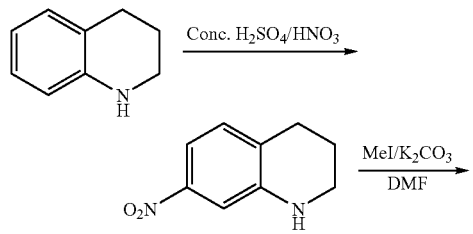

-continued

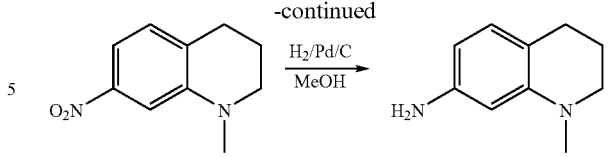

7-Nitro-1,2,3,4-tetrahydroquinoline

To a solution of 1,2,3,4-tetrahydoquinoline (6.5 g, 0.049 mol) in conc. sulfuric acid (118 mL) at 0° C. was added a solution of con. nitric acid (4.9 mL) in conc. Sulfuric acid (12 mL) drop-wise over 3 hours so as to maintain the temperature <5° C. The reaction mixture was then poured onto crushed ice and neutralized with solid potassium carbonate. The mixture was extracted with EtOAc (2×500 mL), the combined organic extracts were washed with water, dried and concentrated to give the crude product which was purified by column chromatography on silica-gel using EtOAc/hexane as eluent to obtain the title compound as an orange solid.

1-Methyl-7-nitro-1,2,3,4-tetrahydroquinoline

To a solution of the 7-nitro-1,2,3,4-tetrahydroquinoline (4.5 g, 25.25 mmol) in DMF (50 mL) was added potassium carbonate (15 g) followed by iodomethane (5.54 g, 39.0 mMol) and the mixture was agitated overnight at ambient temperature. The mixture was poured onto water and extracted with ether (3×200 mL). The combined ethereal extracts were washed with brine, dried and concentrated to give the crude product which was purified by column chromatography on silica-gel to obtain the title compound as an orange liquid.

1-Methyl-1,2,3,4-tetrahydroquinolin-7-ylamine

A mixture of the 1-methyl-7-nitro-1,2,3,4-tetrahydroquinoline (4.0 g, 20.81 mMol), Pd/C (2 g) in methanol (100 mL) was hydrogenated at 10 PSI for 2 hours. The catalyst was filtered off, and the filtrate was concentrated under vacuum to give the crude product which was used as such without further purification.

Intermediate 6

Preparation of 3,4-dihydro-2H-benzo[b][1,4]oxazin-6-amine

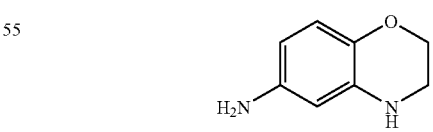

6-Nitro-2H-benzo[b][1,4]oxazin-3(4H)-one

Bromoacetyl bromide (4.84 g, 24 mmol, in 10 mL $CHCl_3$) was added dropwise to the suspension of 2-amino-4-nitrophenyl (3,08 g, 20 mmol), benzyltriethylammonium chloride (TEBA, 4.56 g, 20 mmol) and $NaHCO_3$ (6.72 g, 80 mmol) in 30 mL CHCl₃ with ice bath cooling. The mixture was stirred with ice bath cooling for 1.5 h then at 60° C. overnight. The solvent was removed under vacuum and water was added to the residue. A solid precipitated which was filtered and dried under vacuum to give the product (3.45 g, 89%) as a beige solid.

6-Amino-2H-benzo[b][1,4]oxazin-3(4H)-one

Pd/C (10%) was added to a suspension of 6-nitro-2H-benzo[b][1,4]oxazin-3(4H)-one (1.5 g) in MeOH (20 mL) and the reaction mixture was stirred under an atmosphere of hydrogen overnight. The mixture was filtered through celite and the filtrate was concentrated under vacuum to give the product (0.705 g, 56%) as a beige solid.

3,4-Dihydro-2H-benzo[b][1,4]oxazin-6-amine

6-Amino-2H-benzo[b][1,4]oxazin-3(4H)-one (590 mg, 3.6 mmol) was added to THF solution of borane tetrahydrofuran complex (9 mL, 1M solution) and the reaction mixture was refluxed for 2.5 h. EtOH (2 mL) was added and stirred at 70° C. for 1 h before 1 mL HCl (conc.) was added. The mixture was stirred at 80° C. overnight then the volatiles were removed under vacuum to leave a crude reside. The residue was dissolved in water, NaOH was added until pH~10, and the mixture was extracted with CH₂Cl₂. The organic phase was washed with water and the solvent was removed under vacuum. The residue was purified by column chromatography on silica gel to give the product (274 mg, 51%) as a colorless oil.

Intermediate 7

Preparation of 3,4-dihydo-2H-benzo[b][1,4]oxazin-7-amine

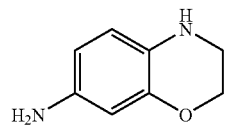

The above was prepared using the same procedure as for 3,4-dihydro-2H-benzo[b][1,4]oxazin-6-amine, except 2-amino-5-nitrophenol was used as starting material.

Intermediate 8

Preparation of 4-methyl-3,4-dihydro-2H-benzo[b][1,4]oxazin-7-amine

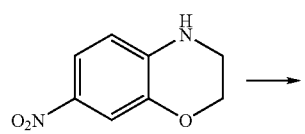

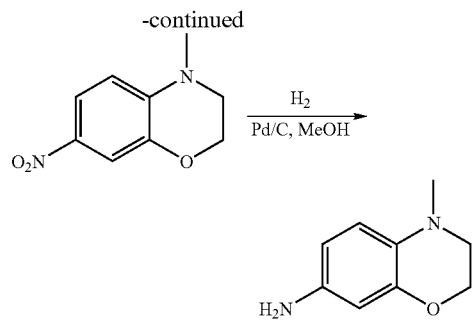

Potassium carbonate (800 mg, 6 mmol) and methyl iodide (1.3 g, 9 mmol) were added to a solution of 3,4-dihydro-7-nitro-2H-benzo[b][1,4]oxazine (540 mg, 3 mmol) in DMF (10 mL). The reaction mixture was stirred at room temperature overnight. Sodium hydride (100 mg, 95%) and methyl iodide (1.0 g) were added and the reaction mixture was stirred at room temperature overnight. The solvent was removed under vacuum and the residue was suspended in water. A solid precipitated which was filtered and washed with water. The bright yellow solid was then suspended in MeOH (20 mL) and Pd/C (10%) was added. The suspension was stirred under an atmosphere of hydrogen overnight, then filtered through celite and the filtrate concentrated under vacuum to give the product (470 mg) as a purple oil.

Intermediate 9

Preparation of 6-amino-2,2-dimethyl-2H-benzo[b][1,4]oxazin-3(4H)-one and 2,2-dimethyl-3,4-dihydro-2H-benzo[b][1,4]oxazin-6-amine

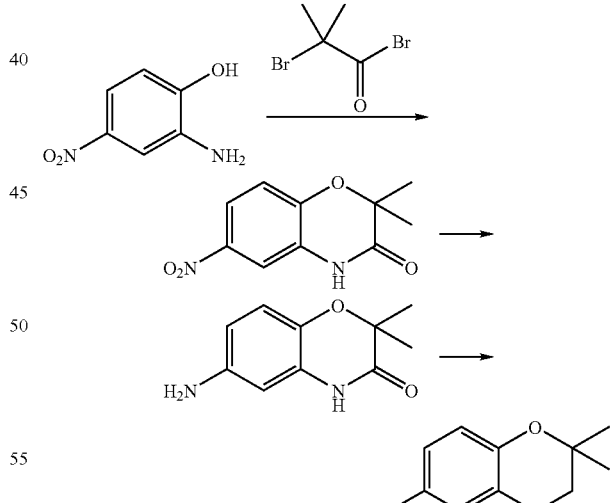

2,2-Dimethyl-6-nitro-2H-benzo[b][1,4]oxazin-3(4H)-one

2-Bromoisobutyryl bromide (10.3 g, 45 mmol, in 20 mL chloroform) was added dropwise to a suspension of 2-amino-4-nitrophenol (4.62 g, 30 mmol) and sodium bicarbonate (10.1 g, 120 mmol) in chloroform (250 mL) under nitrogen with ice bath cooling. The reaction mixture was stirred from 0° C. to room temperature overnight then the solvent was removed under vacuum. The residue was suspended in DMF (150 mL) and potassium carbonate (5.98 g, 45 mmol) was added, then the reaction mixture was stirred at 80° C. overnight. The solvent was removed under vacuum and water was added to the residue. The precipitate that emerged was filtered and dried under vacuum to give the product (4.5 g, 68%) as a light brown solid.

The remainder of the synthesis (hydrogenation of the nitro group and then borane reduction of the lactam) was performed using the general procedure described for 3,4-dihydro-2H-benzo[b][1,4]oxazin-6-amine.

Intermediate 10

Preparation of 7-amino-2,2-dimethyl-2H-benzo[b][1,4]oxazin-3(4H)-one and 2,2-dimethyl-3,4-dihydro-2H-benzo[b][1,4]oxazin-7-amine

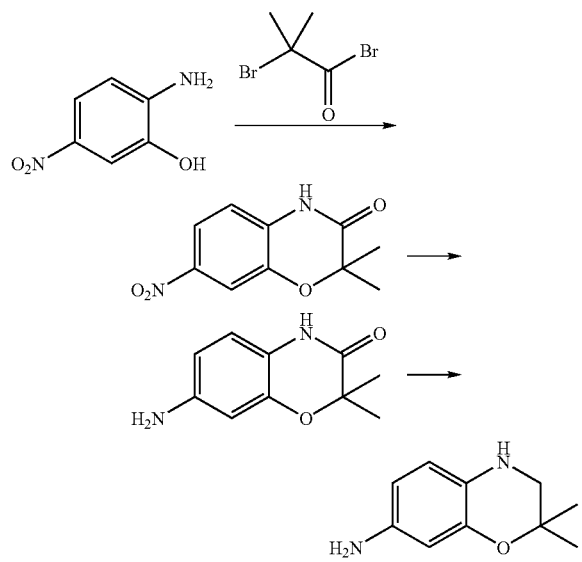

The above was prepared using the same procedures for 6-amino-2,2-dimethyl-2H-benzo[b][1,4]oxazin-3(4H)-one and 2,2-dimethyl-3,4-dihydro-2H-benzo[b][1,4]oxazin-6-amine except 2-amino-5-nitrophenol was used as the starting material.

Intermediate 11

Preparation of 6-chloro-3,4-dihydro-2H-benzo[b][1,4]oxazin-7-amine

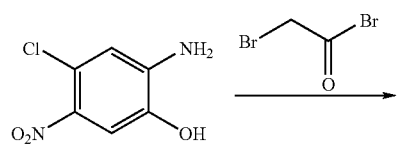

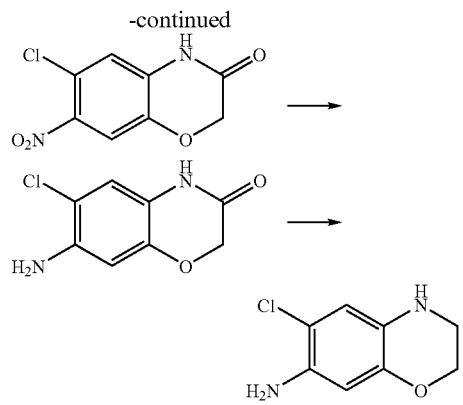

6-chloro-7-nitro-2H-benz[b][1,4]oxazin-3(4H)-one

This compound was prepared using the general procedure described for 2,2-Dimethyl-6-nitro-2H-benzo[b][1,4]oxazin-3(4H)-one above except 2-amino-4-chloro-5-nitrophenol was used as starting material.

7-Amino-6-chloro-2H-benzo[b][1,4]oxazin-3(4H)-one

Stannous chloride dihydrate (30 g, 0.13 mol) was added in portion to a solution of 6-chloro-7-nitro-2H-benzo[b][1,4]oxazin-3(4H)-one (6.7 g, 0.026 mol) in DMF (100 mL) with ice bath cooling. The mixture was allowed to warm to room temperature and was then stirred overnight. EtOAc (300 mL) and MeOH (300 mL) were added to the reaction mixture, Et$_3$N was added until pH>8 and the resulting suspension was filtered through celite. The solvent was removed under vacuum and the residue was suspended in water, extracted with EtOAc, dried (Na$_2$SO$_4$), filtered and concentrated under vacuum. The residue was triturated with ether to give the product (2.5 g, 45%) as a yellow solid.

6-chloro-3,4-dihydro-2H-benzo[b][1,4]oxazin-7-amine

Borane reduction performed using general procedure described above for 3,4-dihydro-2H-benzo[b][1,4]oxazin-6-amine except 7-Amino-6-chloro-2H-benzo[b][1,4]oxazin-3(4H)-one was used as starting material.

Intermediate 12

Preparation of (6-Amino-3H-imidazo[4,5-b]pyridin-2-yl)-methanol

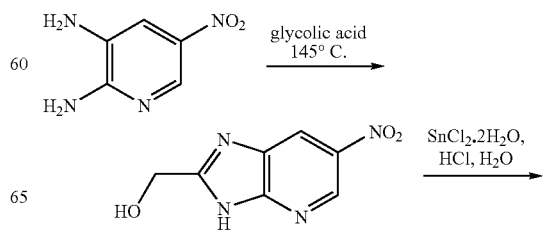

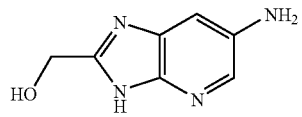

(6-Nitro-3H-imidazo[4,5-b]pyridin-2-yl)-methanol

Solid 2,3-Diamino-5-nitropyridine (prepared according to *J. Med. Chem.* 1997, 40, 3679-3686; 610 mg, 0.0040 mol) and solid glycolic acid (750 mg, 0.0099 mol) were combined in a sealed tube (left open) and heated to 145° C. and stirred for approx. 30-45 min (solid fuses together, liquifies then re-solidifies). After allowing to cool to rt the solid was extracted with 1N HCl. The aqueous mixture was concentrated under vacuum to leave a crude solid that was basified using conc. $NH_3$ solution. The ammonia solution was concentrated under vacuum to leave a crude solid that was dry-loaded on to silica and purified by column chromatography (using the ISCO system) to give a solid (450 mg) that was used directly in the next step.

(6-Amino-3H-imidazo[4,5-b]pyridin-2-yl)-methanol

Stannous chloride dihydrate (1.6 g, 0.0070 mol) was added in one portion to a stirred solution of (6-Nitro-3H-imidazo[4,5-b]pyridin-2-yl)-methanol (450 mg, 0.0023 mol) in 10% aqueous hydrochloric acid (20 mL) at 50° C. The mixture was stirred at 50° C. for approx. 2 hours then allowed to cool to room temperature. The mixture was cooled further to 0° C. and then basified to ca. pH 8 using conc. $NH_3$ solution. The aqueous layer was then filtered through Celite® to remove tin salts and the filtrate was concentrated under vacuum to leave a crude solid (380 mg; yield assumed quantitative) which was used directly in the next step (amide formation).

Intermediate 13

Preparation of (3-aminoquinolin-7-yl)methanol (prepared using the general procedure from *J. Am. Chem. Soc.* 1997, 119, 5591)

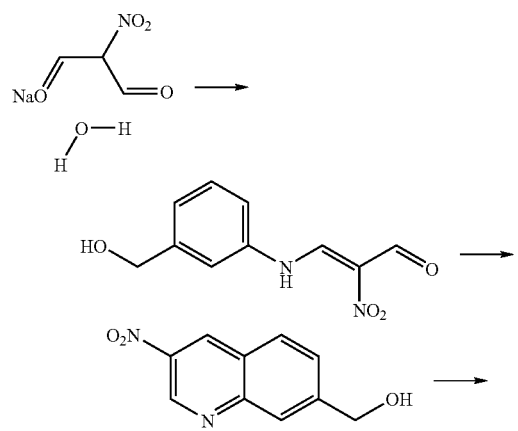

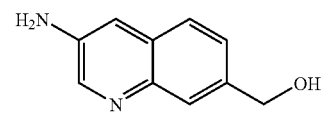

3-(3-(hydroxymethyl)phenylamino)-2-nitroacrylaldehyde

3-Aminobenzyl alcohol (4.97 g, 0.0404 mol) was dissolved in 4 mL conc HCl. Sodium nitromalonaldehyde monohydrate (prepared from mucobromic acid according to the procedure in *Organic Syntheses Vol IV*, pp 844, 1963) (4.25 g, 0.0269 mol) was dissolved in 35 mL water and added to the amine solution (a yellow precipitate formed immediately)—a further 80 mL of water being added to aid stirring. After 10 min, the precipitate was filtered, washed with water and air dried overnight to give the product (4.3 g) as a yellow solid.

(3-nitroquinolin-7-yl)methanol 3-(3-(hydroxymethyl)phenylamino)-2-nitroacrylaldehyde (4.3 g, 19.4 mmol) was placed in 20 mL HOAc. 4.8 g of 3-aminobenzyl alcohol (4.8 g, 38.7 mmol) was dissolved in 5 mL conc HCl, then 20 mL HOAC was added to the HCl solution. This mixture was added to the reaction flask containing the 3-(3-(hydroxymethyl)phenylamino)-2-nitroacrylaldehyde in HOAc. The mixture was heated to reflux under nitrogen and after 20 min, benzene thiol (0.19 mL, 0.19 mmol) was added. The mixture was refluxed for 28 h (m/z=208.1). After allowing to cool, acid was removed under vacuum. The residue was dissolved in EtOAc/MeOH and loaded on a silica gel cartridge. Purification by column chromatography on silica gel using hexane/EtOAc (0-50%) then 10% MeOH/EtOAc as eluent gave the product (500 mg, 9%) as a brown solid.

(3-aminoquinolin-7-yl)methanol (3-nitroquinolin-7-yl)methanol (1.2 g, 0.0059 mol) and 400 mg of Pd/C (10% wt) were placed in 60 mL dry THF. The mixture was stirred under a hydrogen atmosphere (balloon) overnight. The reaction was filtered through celite and the filtrate concentrated to an oil. Purification by column chromatography on silica gel using MeOH/$CH_2Cl_2$ (0-10%) as eluent provided 0.9 g of an oily product. m/z=216.9 (+acetic acid). The product was suspended in MeOH and $K_2CO_3$ (200 mg) was added. This mixture was stirred at room temperature for 4 h. m/z=175.1. The mixture was filtered and the filtrate was concentrated under vacuum to give the product (172 mg, 19%) as a moist solid. $^1$H NMR ($d_4$-MeOD) δ 8.32 (1H, d), 7.69 (1H, s), 7.55 (1H, d), 7.34 (1H, dd), 7.23 (1H, d), 5.40 (2H, s).

Intermediate 14

Preparation of (6-amino-1H-indazol-3-yl)methanol

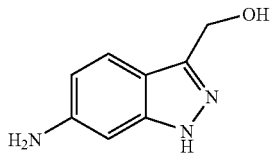

6-nitro-1H-indazole-3-carbaldehyde (500 mg, 0.003 mol) was dissolved in 50 mL THF. Lithium tetrahydroaluminate (400 mg, 0.01 mol) was added in 3 portions and the reaction mixture was stirred at room temperature overnight. Water (400 μL), 15% NaOH solution (400 μL), then water (1.2 mL) was added, and then the crystalline brown-yellow precipitate was filtered off. The filtrate was concentrate to an oil which was used directly in the next step without further purification. m/z=164.0. $^1$H NMR (d$_4$-MeOH) δ 7.2 (1H, d), 7.05 (1H, d), 6.85 (1H, dd), 4.74 (2H, s).

Intermediate 15

Preparation of (7-aminoquinolin-3-yl)methanol

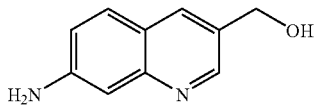

2-Dimethylaminomethylene-1,3-bis(dimethylimmonio)propane bis(tetrafluoroborate)

To a 3-neck flask equipped with a reflux condenser was added bromoacetic acid (25 g, 0.18 mol) and phosphoryl chloride (50 mL, 0.54 mol). The solution was cooled to 0° C. and N,N-dimethylformamide (84 mL, 1.1 mol) was added dropwise over 30 min. The resulting solution was heated at 110° C. for 3 h. As the mixture was heated, it began to exotherm and evolve CO$_2$. The mixture was then cooled to 0° C. and a solution of aqueous 50% tetrafluoroboric acid (63 g, 0.36 mol) in MeOH (100 mL) was added slowly over 1 h via an addition funnel. Isopropanol (100 mL) was added to the dark viscous solution. Solids precipitated and the slurry was stirred at 0° C. for 2 h. The solids were collected by filtration to provide the product (64 g, 72%) as a pale yellow solid.

Benzyl 3-aminophenylcarbamate

To a stirred solution of m-phenylenediamine (5.0 g, 0.046 mol) and N,N-diisopropylethylamine (8.0 mL, 0.046 mol) in CH$_2$Cl$_2$ (150 mL) at 0° C. was added slowly benzyl chloroformate (6.6 mL, 0.046 mol). The mixture was stirred at 0° C. for 2 h and then warmed to rt for 2 h. Aq. NaHCO$_3$ solution was added and the organic phase was separated, washed with brine, dried (Na$_2$SO$_4$) and concentrated. The residue was purified by column chromatography on silica gel to give the desired product (8.0 g, 71%) as a syrup. LC-MS: 2.11 min, 243.0 (M+1).

Benzyl 3-formylquinolin-7-ylcarbamate

A slurry of benzyl 3-aminophenylcarbamate (8.0 g, 0.033 mol) and 2-dimethylaminomethylene-1,3-bis(dimethylimmonio)propane bis(tetrafluoroborate) (31 g, 0.087 mol) in ethanol (400 mL) was heated at reflux for 24 h. The solution was concentrated under vacuum and the residue was dissolved in THF (200 mL) and 1N HCl (200 mL). The reation mixture was stirred at rt overnight, then poured into a saturated solution of sodium bicarbonate (200 mL), and extracted with EtOAc (2×). The combined organic layers were washed with brine, dried (Na$_2$SO$_4$), and concentrated under vacuum to afford the desired product (10.0 g, 99%) as a yellow solid. LC-MS: 2.84 min, 307.1 (M+1).

Benzyl 3-(hydroxymethyl)quinolin-7-ylcarbamate

To a stirred mixture of benzyl 3-formylquinolin-7-ylcarbamate (2.0 g, 0.0065 mol), THF (50 mL), MeOH (50 mL), and water (50 mL) was added sodium tetrahydroborate (0.25 g, 0.0065 mol). The mixture was stirred at rt until LC-MS indicated no SM. The mixture was acidified with 1N HCl and concentrated under vacuum, and then treated with aq. NaHCO$_3$ solution and EtOAc. The organic layer was separated and washed with brine, dried (Na$_2$SO$_4$), and evaporated. The residue was purified by column chromatography on silica gel using MeOH-EtOAc (0-10%) as eluent to give the product (1.3 g, 64%) as a light yellow solid. LC-MS: 1.83 min, 309.2 (M+1).

(7-Aminoquinolin-3-yl)methanol

A mixture of benzyl 3-(hydroxymethyl)quinolin-7-ylcarbamate (480 mg, 0.0016 mol), 10% Pd—C (50 mg), and MeOH (50 mL) was stirred under H$_2$ (1 atm) for 1 h. The catalyst was filtered-off and the filtrate was concentrated to give the product as a yellow solid. LC-MS: 0.34 min, 175.1 (M+1).

Intermediate 16

Preparation of quinolin-7-amine

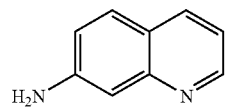

A mixture of 7-nitroquinoline (0.30 g, 0.0017 mol; Specs, Inc.), 10% Pd—C (50 mg), and MeOH (20 mL) was stirred under H$_2$ (1 atm) for 2 h. The mixture was filtered and the filtrate was concentrated to give a yellow solid (235 mg, 95%). LC-MS: 0.33 min, 145.1 (M+1).

$^1$H NMR (DMSO-d$_6$): 8.58 (1H, dd, J=4.4, 1.6 Hz), 8.00 (1H, dd, J=8.0, 1.2 Hz), 7.60 (1H, d, J=8.8 Hz), 7.07 (1H, dd, J=8.0, 4.4 Hz), 6.98 (1H, dd, J=8.8, 2.0 Hz), 6.93 (1H, d, J=2.0 Hz), 5.75 (s, 2H).

Intermediate 17

Preparation of 5-amino-3-methylisoquinoline

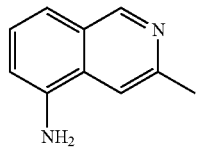

5-amino-3-methylisoquinoline

A mixture of 3-methyl-5-nitroisoquinoline (1.3 g, 0.0069 mol—prepared according to the procedure in WO 2004/024710), 10% Pd—C (100 mg) and MeOH (100 mL) was stirred under an atmosphere of hydrogen (1 atm) at rt for 2 h. The mixture was filtered and the filtrate was concentrated under vacuum to give a light yellow solid (1.1 g, 100%). LC-MS: 0.64 min, 159.1 (M+1).

Intermediate 18

Preparation of 1-chloroisoquinolin-5-amine

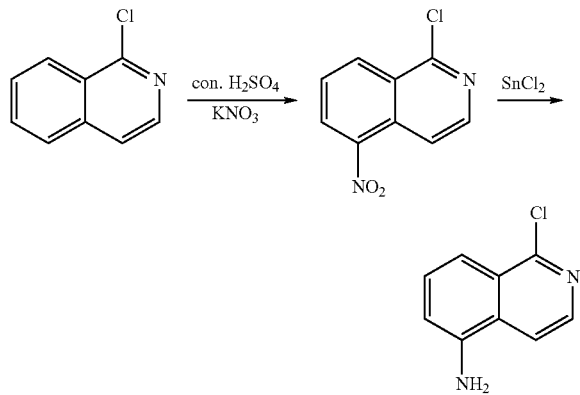

1-chloro-5-nitroisoquinoline

A mixture of 1-chloroisoquinoline (6.0 g, 0.037 mol) in conc. $H_2SO_4$ (35 mL) was treated with a solution of fuming $HNO_3$ (10 mL) and potassium nitrate (4.0 g, 0.040 mol) in conc. $H_2SO_4$ (35 mL) at 0-5° C. The mixture was stirred at 0° C. for a further 90 min, and poured into ice. The precipitate was collected, washed and dried to give the product as a yellow solid. LC-MS: 3.68 min, 209.2 & 211.1 (M+1).

1-chloroisoquinolin-5-amine

A mixture of 1-chloro-5-nitroisoquinoline (450 mg, 0.0022 mol), stannous chloride dihydrate (2.4 g, 0.011 mol), and EtOAc (50 mL) was stirred under reflux under an atmosphere of nitrogen for 3 h. After cooling, the mixture was poured into ice-water and basified to pH 10.0 with aq. $Na_2CO_3$. The organic phase was separated and the aqueous phase was extracted with EtOAc. The combined organic layers were washed with brine, dried ($Na_2SO_4$) and concentrated under vacuum. The residue was purified by column chromatography on silica gel to give the product as a light yellow solid. LC-MS: 3.17 min, 179.2 & 181.2 (M+1).

Intermediate 19

Preparation of 7-amino-3,4-dihydro-2H-benzo[b][1,4]oxazin-3-yl)methanol and 8-amino-2,3,4,5-tetrahydrobenzo[b][1,4]oxazepin-3-ol

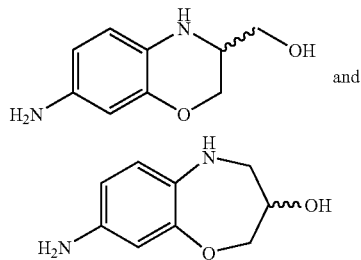

3,4-dihydro-7-nitro-2H-benzo[b][1,4]oxazin-3-yl)methanol and 8-amino-2,3,4,5-tetrahydrobenzo[b][1,4]oxazepin-3-ol A mixture of 2-amino-5-nitrophenol (10.0 g, 0.0649 mol), potassium carbonate (13.4 g, 0.0973 mol), cesium fluoride (2.0 g, 0.013 mol) and 1-bromo-2,3-epoxypropane (5.37 mL, 0.0649 mol) in DMF (120 mL) was stirred under $N_2$ at rt overnight and then heated at 100° C. for 10 h. After cooling, the solvent was removed under vacuum and the residue was partitioned between water and EtOAc. The organic layer was washed with brine, dried ($Na_2SO_4$) and concentrated. The residue was purified by column with $CH_2Cl_2$-EtOAc (containing 5% $Et_3N$) (0 to 40%) to give an orange solid. LC-MS: 2.30 min, 211.1 (M+1).

7-amino-3,4-dihydro-2H-benzo[b][1,4]oxazin-3-yl)methanol and 8-amino-2,3,4,5-tetrahydrobenzo[b][1,4]oxazepin-3-ol (3,4-dihydro-7-nitro-2H-benzo[b][1,4]oxazin-3-yl)methanol (3.8 g, 0.018 was hydrogenated at 40 PSi for 2 hours over 10% Pd/C. The mixture was filtered through celite and the filtrate was concentrated under vacuum to afford the crude product. Purification by column chromatography on silica-gel (EtOAc) gave the product as a dark brown oil. LC-MS: 0.36 min, 181.1 (M+1). $^1$H NMR (DMSO-$d_6$): 6.32 (1H, d, J=9.2 Hz), 6.01-5.97 (2H, m), 4.82-4.76 (2H, m), 4.29 (2H, s), 4.08 (1H, dd, J=10.4, 1.6 Hz), 3.79 (1H, dd, J=10.4, 6.8 Hz), 3.35 (2H, m), 3.17 (1H, m). 8-Amino-2,3,4,5-tetrahydrobenzo[b][1,4]oxazepin-3-ol was also isolated from above procedure as a minor byproduct.

Intermediate 20

Preparation of (S)-(3,4-dihydro-7-nitro-2H-benzo[b][1,4]oxazin-3-yl)methanol

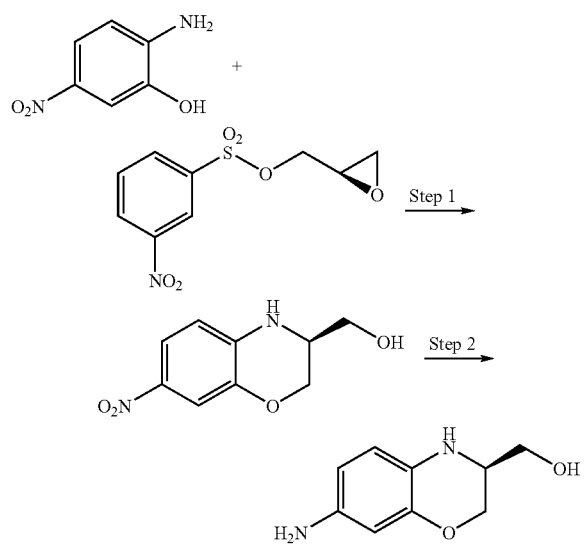

(S)-(3,4-dihydro-7-nitro-2H-benzo[b][1,4]oxazin-3-yl)methanol

Sodium hydride (0.810 g, 0.0202 mol) was added slowly to a mixture of 2-amino-5-nitrophenol (3.0 g, 0.019 mol) in dmf (50 ml) at 0° C. The mixture was stirred at rt for 1 h and then (r)-(oxiran-2-yl)methyl 3-nitrobenzenesulfonate (5.0 g, 0.019 mol) was added. The mixture was stirred at room temperature overnight and then DMF was removed under vacuum. The residue was partitioned between water and EtOAc. The organic layer was washed with aqueous $Na_2CO_3$ solution, brine, dried ($Na_2SO_4$) and concentrated under vacuum to give a brown solid (5.2 g). A mixture of the above brown solid, $K_2CO_3$ (2.0 g) and DMF (200 ml) was stirred at 120° C. under $N_2$ overnight. After cooling, the solvent was removed in vacuo and the residue was partitioned between water and EtOAc. The organic layer was washed with brine, dried ($Na_2SO_4$) and concentrated under vacuum. The residue was purified by column chromatography on silica gel with $CH_2Cl_2$-EtOAc (containing 5% $Et_3N$—0 to 60%) to give the product as a soft brown solid. LC-MS: 2.30 min, 211.1 (m+1).

(S)-(7-Amino-3,4-dihydro-2H-benzo[b][1,4]oxazin-3-yl)methanol

A mixture of (s)-(3,4-dihydro-7-nitro-2h-benzo[b][1,4]oxazin-3-yl)methanol (340 mg, 0.0016 mol), 10% Pd/C (50 mg) and MeOH (50 ml) were stirred under an atmosphere of hydrogen (1 atm) for 3 h. LC-MS indicated completion of reaction. The mixture was filtered and the filtrate was concentrated under vacuum to give the product as a brown syrup. LC-MS: 0.36 min, 181.1 (m+1).

(R)-(7-amino-3,4-dihydro-2h-benzo[b][1,4]oxazin-3-yl) methanol was prepared using the same procedure as for (s)-(3,4-dihydro-7-nitro-2h-benzo[b][1,4]oxazin-3-yl) methanol, except (s)-(oxiran-2-yl)methyl 3-nitrobenzene-sulfonate was used as starting material.

Intermediate 21

Preparation of (7-amino-2,3-dihydro-benzo[1,4]dioxin-2-yl)-methanol 9see 43P—Intermediate 19)

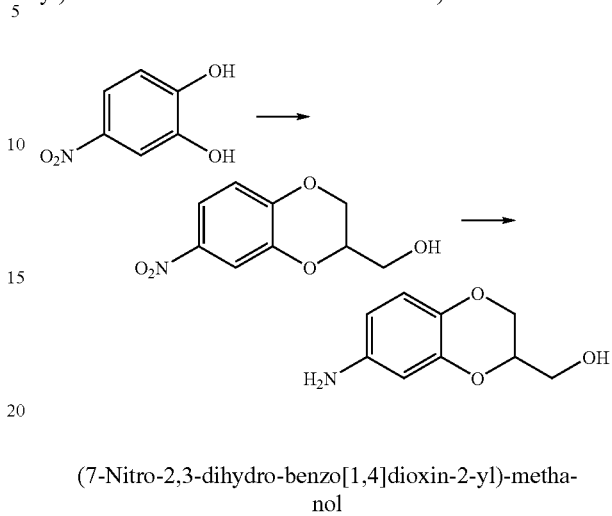

(7-Nitro-2,3-dihydro-benzo[1,4]dioxin-2-yl)-methanol 3.0 g of sodium hydrogen carbonate was suspended in 90 mL DMF. At 0° C. a solution of 5.15 g of 4-nitrocatechol was added dropwise over 15 min. Subsequently, 3.9 g of epichlorohydrin in 10 mL DMF were added over 15 min. Stirring was continued at room temperature, then at 80° C. overnight. The mixture was diluted with water and extracted three times with ethyl acetate, dried (anhyd. $Na_2SO_4$), filtered and concentrated under vacuum to give a yellow oil. The oil was purified by column chromatography on silica gel using EtOAc-hexanes (0-100% gradient) to give the product (2.8 g) as a yellow solid.

(7-amino-2,3-dihydro-benzo[1,4]dioxin-2-yl)-methanol (7-nitro-2,3-dihydro-benzo[1,4]dioxin-2-yl)-methanol (1.0 g, 4.7 mmol) was dissolved in methanol (30 ml) and palladium on activated carbon was added (0.10 g, 5% wt). The mixture was shaken on a parr shaker under $H_2(g)$ atmosphere (60 psi) for 24 hours. The mixture was filtered through celite and evaporated to give 722 mg of material as a white solid (86%), which was used as such for the next step. M/z=182 (m+1). Lc: 0.82 minutes.

Intermediate 22

Preparation of (6-Amino-2,3-dihydro-benzo[1,4] dioxin-2-yl)-methanol

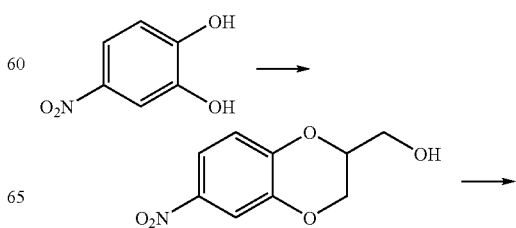

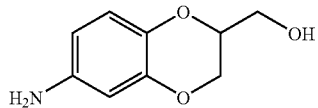

(6-Nitro-2,3-dihydro-benzo[1,4]dioxin-2-yl)-methanol 1.93 g of 60% sodium hydride was suspended in 90 mL DMF. At 0° C. a solution of 5.15 g of 4-nitrocatechol was added dropwise over 15 min. Subsequently, 3.9 g of epichlorohydrin in 10 mL DMF were added over 15 min. Stirring was continued at room temperature, then at 80° C. overnight. The mixture was diluted with water and extracted three times with ethyl acetate, dried ($Na_2SO_4$), filtered and concentrated under vacuum to give a yellow oil. The oil was purified by column chromatography on silica gel using a EtOAc-hexanes (0-100% gradient) to give the product (2.3 g) as a yellow solid.

(6-Amino-2,3-dihydro-benzo[1,4]dioxin-2-yl)-methanol (6-Nitro-2,3-dihydro-benzo[1,4]dioxin-2-yl)-methanol (1.0 g, 4.7 mmol) was dissolved in methanol (30 mL) and palladium on activated carbon was added (0.10 g, 5% wt). The mixture was shaken on a Parr Shaker under $H_2(g)$ atmosphere (60 PSI) for 24 hours. The mixture was filtered through Celite® and evaporated to give 646 mg of material as a white solid (77%), which was used as such for the next step. m/z=182 (M+1). LC: 0.82 minutes.

Intermediate 23

Preparation of (7-amino-3,4-dihydro-2H-pyrido[3,2-b][1,4]oxazin-3-yl)methanol

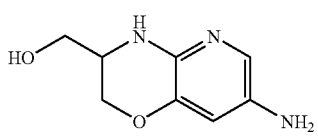

2-amino-3-methoxy-5-nitropyridine

Into a 250 mL sealed tube were combined 2-chloro-3-methoxy-5-nitropyridine (0.50 g, 0.00265 mol), concentrated ammonium hydroxide (5 mL, 0.1 mol) and ethanol (20 mL). The mixture was heated to 80° C. and stirred overnight. After allowing to cool to room temperature, the mixture was reduced in vacuo and the residue was taken up in ethyl acetate (50 mL), then washed with equal amounts of brine and water (1×50 mL each). The organic layer was dried ($Na_2SO_4$), filtered and concentrated under vacuum to leave a solid (0.312 g, 69%) which was used directly in the next step without further purification. LC-MS 1.94 min. M/Z=171.0 (M+1).

2-amino-3-hydroxy-5-nitropyridine

Into a 500 mL round bottom flask were combined 2-amino-3-methoxy-5-nitropyridine (0.300 g, 0.00177 mol) and solid pyridine hydrochloride (8.8 g, 0.076 mol). The solid mixture was heated at 150° C. upon which the solids fused (the evolution of a gas was also apparent). The mixture was held at 150° C. for three hours upon which reaction was deemed complete by LC-MS. After allowing to cool to 80° C., the mixture was poured on to ice and the aqueous layer was extracted with ethyl acetate (3×100 ml). The combined organic extracts were washed with water (2×100 mL), dried ($Na_2SO_4$), filtered and concentrated under vacuum to leave a crude residue. The residue was purified by column chromatography on silica gel using a methanol:methylene chloride (0-10%) gradient as eluent to give the product as a solid (0.138 g, 49%) which was used directly in the next step. LC-MS 1.28 min. m/z=155.9 (M+1).

(7-nitro-3,4-dihydro-2H-pyrido[3,2-b][1,4]oxazin-3-yl)methanol

Into a 75 mL sealed tube were combined 2-amino-3-hydroxy-5-nitropyridine (0.138 g, 0.000890 mol), N,N-dimethylformamide (4.1 mL) and potassium carbonate (0.39 g, 0.0028 mol). The mixture was allowed to stir at room temperature for 10 minutes then 1-bromo-2,3-epoxypropane (0.12 g, 0.00089 mol) was added in one portion. The flask was sealed, then heated to 110° C. and stirred overnight. After allowing to cool, the mixture was concentrated under vacuum to give a crude solid which was dissolved in EtOAc (75 mL), washed with water and brine, then dried ($Na_2SO_4$), filtered and concentrated under vacuum to leave a crude residue. The residue was purified by column chromatography on silica gel using MeOH/$CH_2Cl_2$ (0-10% gradient) as eluent to give a solid (0.092 g, 46%). LC-MS 1.92 min. M/Z=212.0 (M+1). $^1$H NMR ($d_6$-DMSO) δ 8.8 (d, 1 H), 7.8 (d, 1 H), 5.1 (t, 1H), 4.2 (m, 1 H), 4.0 (m, 1H), 3.62 (m, 1H), 3.45 (m, 1H), 3.21 (m, 1H).

(7-amino-3,4-dihydro-2H-pyrido[3,2-b][1,4]oxazin-3-yl)methanol

Into a 500 mL round bottom flask were combined (7-nitro-3,4-dihydro-2H-pyrido[3,2-b][1,4]oxazin-3-yl)methanol (0.320 g, 0.00152 mol), 10%-palladium on carbon (0.06 g, 0.0005 mol) and methanol (50 mL). The apparatus was evacuated, then hydrogen was introduced and the mixture was allowed to stir overnight (at 1 atm presuure). The mixture was then filtered through celite and the filtrate was concentrated under vacuum to yield an oil (0.252 g, 89%) which was used directly in the next step without further purification. (0.252 g, 89%) LC-MS 0.29 min. M/Z=181.9 (M+1).

Intermediate 24

Preparation of (5-amino-1H-indol-2-yl)methanol

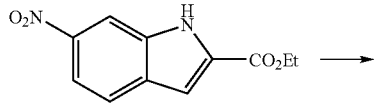

-continued

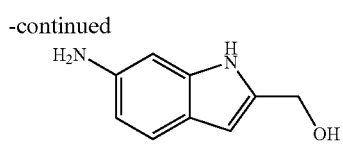

2-Ethoxycarbonyl-5-nitroindole (500 mg, 0.002 mol) was dissolved in 50 mL THF, added lithium tetrahydroaluminate (341 mg, 0.00898 mol) in 3 portions and stirred at room temperature overnight. Water (341 µL), 15% NaOH solution (341 µL), and water (1.1 mL) were added cautiously and the mixtured was filtered. The filtrate was concentrated under vacuum to give the product (300 mg, 98%) as an oil. m/z=162.9.

Intermediate 25

Preparation of (5-amino-1H-indazol-3-yl)methanol

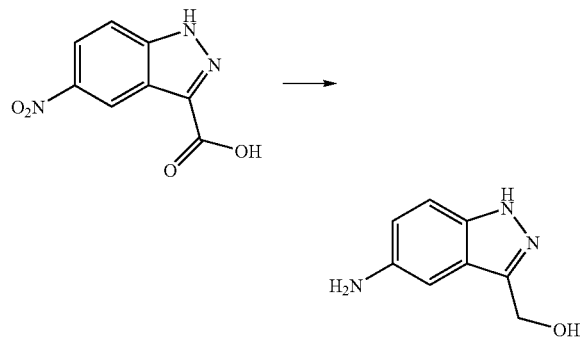

5-nitro-1H-indazole-3-carboxylic acid (500 mg, 0.002 mol) was dissolved in 50 mL THF, added lithium tetrahydroaluminate (366 mg, 0.00964 mol) in 3 portions and stirred at room temperature overnight. 65 mg (15%). Water (366 µL), 15% NaOH solution (366 µL), and water (1.1 mL) were added cautiously and the mixtured was filtered. The filtrate was concentrated under vacuum to give the product (65 mg, 15%) as an oil. m/z=160.0.

Preparation of Amido Compounds

Amide Formation

Method A: A Representative Synthesis of Benzamides

A mixture of the appropriate acid (1.0 eq), N-(3-dimethylaminopropyl)-N'-ethylcarbodiimide hydrochloride (1.0 eq), 4-N,N-dimethylaminopyridine (1.0 eq), triethylamine (2.0 eq) and the appropriate amine (1.5 eq) in $CH_2Cl_2$ (ca. 3 mL per 0.12 mmol) were combined and the mixture was stirred at room temperature overnight. The mixture was concentrated under vacuum (to ca. 1 mL) and then purified by preparative thin-layer chromatography. The above reaction was typically run on a 0.12 mmol scale.

Formation of Amide Products from Geometrical Isomer A

Method B.

2-methyl-4-(2-(trifluoromethyl)cyclopropyl)benzoic acid geometrical isomer A (note: this compound is a racemic mixture and contains two enantiomers; 16 mg, 0.07 mmol), 1-hydroxybenzotriazole (15 mg, 0.08 mmol) and N-(3-dimethylaminopropyl)-N'-ethylcarbodiimide hydrochloride (15 mg, 0.08 mmol) were dissolved in $CH_2Cl_2$ then N,N-di-iso-propylethylamine (30 µL, 0.2 mmol) was added. The mixture was stirred at rt for 15 min then the appropraite amine (2.0 eq based on acid starting material) was added and the mixture stirred overnight. The mixture was concentrated under vacuum (to ca. 1 mL) and then purified by preparative thin-layer chromatography.

Formation of Amide Products from Geometrical Isomer B

Method C.

2-methyl-4-(2-(trifluoromethyl)cyclopropyl)benzoic acid geometrical isomer B (note: this compound is a racemic mixture and contains two enantiomers; 16 mg, 0.07 mmol), 1-hydroxybenzotriazole (15 mg, 0.08 mmol) and N-(3-dimethylaminopropyl)-N'-ethylcarbodiimide hydrochloride (15 mg, 0.08 mmol) were dissolved in $CH_2Cl_2$ then N,N-di-iso-propylethylamine (30 µL, 0.2 mmol) was added. The mixture was stirred at room temperature for 15 min then the appropraite amine (2.0 eq based on acid starting material) was added and the mixture stirred overnight. The mixture was concentrated under vacuum (to ca. 1 mL) and then purified by preparative thin-layer chromatography.

Compound 1

Preparation of 4-cyclopropyl-N-(3-methoxyphenyl)-2-methylbenzamide

Prepared using method A with EtOAc/hexane (1:9) as eluent for the preparative thin-layer chromatography to give the product (19 mg, 55%) as a solid.

Compound 2

Preparation of N-(4-tert-butylphenyl)-4-cyclopropyl-2-methylbenzamide

Prepared using method A with EtOAc/hexane (7.5:92.5) as eluent for the preparative thin-layer chromatography to give the product (25 mg, 66%) as a solid.

Compound 3

Preparation of 4-(2,2-dichlorocyclopropyl)-N-(quinolin-3-yl)benzamide

Prepared using method A with EtOAc/hexane (2:1) as eluent for the preparative thin-layer chromatography to give the product (27 mg, 58%) as a solid.

Compound 4

Preparation of 4-(2,2-dichlorocyclopropyl)-N-(3-methoxyphenyl)benzamide

Prepared using method A. After purification by prepative thin-layer chromatography the compound was purified further passing through an ion exchange cartridge (sequesters the amine starting material which is the impurity) to give the product (17 mg, 38%) as a solid.

Compound 5

Preparation of 4-cyclopropyl-2-methyl-N-(quinolin-3-yl)benzamide

Prepared using method A. After preparative thin-layer chromatography the compound was purified further by ion-exchange chromatography and then column chromatography on silica gel (ISCO system) to give the product (20 mg, 50%) as a solid.

Compound 6

Preparation of 4-(2,2-dichlorocyclopropyl)-N-(2-methylbenzo[d]thiazol-5-yl)benzamide Prepared using method A. After preparative thin-layer chromatography the compound was purified further by column chromatography on silia gel (ISCO system) to give the product (2.7 mg, 5%) as a solid.

Compound 7

Preparation of 4-cyclopropyl-2-methyl-N-(2-methylbenzo[d]thiazol-5-yl)benzamide

Prepared using method A. After preparative thin-layer chromatography the compound was purified further by column chromatography on silica gel (ISCO system) to give the product (14 mg, 35%) as a solid.

Compound 8

Preparation of N-(2,3-dihydrobenzo[b][1,4]dioxin-6-yl)-2-methyl-4-(2-(trifluoromethyl)cyclopropyl)benzamide Prepared using method C to give the product (16 mg, 65%) as a solid.

Compound 9

Preparation of 2-methyl-N-(5,6,7,8-tetrahydronaphthalen-1-yl)-4-(2-(trifluoromethyl)cyclopropyl)benzamide Prepared using method C to give the product (13 mg, 51%) as a solid after further purification by high-performance liquid chromatography.

Compound 10

Preparation of N-(6-methoxypyridin-3-yl)-2-methyl-4-(2-(trifluoromethyl)cyclopropyl)benzamide Prepared using method C to give the product (15 mg, 66%) as a solid.

Compound 11

Preparation of 2-methyl-N-(2-methylbenzo[d]thiazol-5-yl)-4-(2-(trifluoromethyl)cyclopropyl)benzamide Prepared using method C except after 24 hours further N,N-di-iso-propylethylamine (3 eq) was added and the mixture was heated at 30° C. overnight. Further purification by preparative thin-layer chromatography gave the product (24 mg, 47%) as a solid.

Compound 12

Preparation of 2-methyl-N-(2-methylbenzo[d]thiazol-5-yl)-4-(2-(trifluoromethyl)cyclopropyl)benzamide Prepared using method B to give the product (7 mg, 36%) as a solid.

Compound 13

Preparation of N-(2,3-dihydrobenzo[b][1,4]dioxin-6-yl)-2-methyl-4-(2-(trifluoromethyl)cyclopropyl)benzamide Prepared using method B to give the product (7 mg, 30%) as a solid.

Compound 14

Preparation of N-(4-tert-butylphenyl)-2-methyl-4-(2-(trifluoromethyl)cyclopropyl)benzamide Prepared using method B except after 24 hours further N,N-di-iso-propylethylamine (3 eq) was added and the mixture was heated at 30° C. overnight. Further purification by preparative thin-layer chromatography gave the product (7 mg, 30%) as a solid.

Compound 15

Preparation of N-(2-hydroxymethyl)benzo[d]thiazol-5-yl)-2-methyl-4-(2-(trifluoromethyl)cyclopropyl)benzamide Selenium(IV) oxide (17 mg, 0.15 mmol) and 2-methyl-N-(2-methylbenzo[d]thiazol-5-yl)-4-(2-(trifluoromethyl)cyclopropyl)benzamide (material from isomer B; 20 mg, 0.05 mmol) were combined in 1,4-dioxane (2 mL) under nitrogen, heated to 80° C. and stirred overnight. After allowing to cool to room temperature, the mixture was filtered through celite and the filter cake was washed with 1,4-dioxane. The filtrate was partitioned between EtOAc and saturated $NaHCO_3$(aq) and the organic layer was washed with $H_2O$ and brine, then dried ($Na_2SO_4$), filtered and the filtrate concentrated under vacuum to leave a crude residue. The residue was dissolved in THF (2 mL) and $H_2O$ (1 mL) and sodium tetrahydroborate (19 mg, 0.5 mmol) was added. The mixture was stirred at room temperature overnight then acidifed by the use of 1N HCl. The mixture was then made basic with saturated $NaHCO_3$(aq) and extracted with EtOAc. The organic layer was washed with $H_2O$ and brine, then dried ($Na_2SO_4$), filtered and the filtrate concentrated under vacuum to leave a crude residue. The residue was purified by preparative thin-layer chromatography using EtOAc/hexane (1:4) as eluent to give the product (4 mg, 20%) as a solid.

Compound 16

Preparation of N-(3-methoxyphenyl)-2-methyl-4-(2-(trifluoromethyl)cyclopropyl)benzamide Prepared using method B except after 24 hours further N,N-di-iso-propylethylamine (3 eq) was added and the mixture was heated at 30° C. overnight. Further purification by preparative thin-layer chromatography gave the product (6 mg, 36%) as a solid.

Compounds 17-20

Preparation of (1R,2R), (1R,2S), (1S,2R) and (1S,2S)2-methyl-N-(quinolin-3-yl)-4-(2-(trifluoromethyl)cyclopropyl)benzamide Trimethylaluminum (1.0 M in hexane; 2.3 mL) was added over 2-3 min to a stirred solution of 3-quinolinamine (330 mg, 2.3 mmol) in toluene (20 mL) at room temperature under nitrogen. The mixture was stirred at room temperature overnight (reactions turns red in color), then a solution of methyl cis- and trans-methyl 2-methyl-4-(2-(trifluoromethyl)cyclopropyl)benzoate (300 mg, 1.2 mmol) in toluene (10 mL) was added in one portion and the mixture heated to reflux and stirred for 3 hours. After allowing to cool, a saturated solution of NaHCO$_3$(aq) (20 mL) was added dropwise, followed by CH$_2$Cl$_2$ (50 mL). The mixture was stirred vigerously for 30 min then the aqueous and organic layers were partitioned. The aqueous was extracted with CH$_2$Cl$_2$ (2×50 mL) and the combined organic extracts were dried (Na$_2$SO$_4$), filtered and the filtrate concentrated under vacuum to leave a crude solid which contained all the stereoisomers of 2-methyl-N-(quinolin-3-yl)-4-(2-(trifluoromethyl)cyclopropyl)benzamide in addition to excess 3-quinolinamine and other by-products.

The crude product from the above reaction was separated by chromatography (OD-H chiral column), using supercritical carbon dioxide and ethanol as eluent, on a BergerSFC MultiGram II and collecting on UV detection at 220 nM to give;

Isomer 1 (Compound 17) as a solid (14.3 mg). Re-purified using ion exchange chromatography and preparative thin-layer chromatography using EtOAc/hexane (3:7) as eluent to give a solid (7 mg).

Isomer 2 (Compound 18) as a solid (20.1 mg). Re-purified by ion exchange chromatography and preparative thin-layer chromatography using EtOAc/hexane (3:7) as eluent to give a solid (8 mg).

Isomer 3 (Compound 19) as a solid (28 mg).

Isomer 4 (Compound 20) as a solid (28 mg). Re-purified by ion exchange chromatography and preparative thin-layer chromatography using EtOAc/hexane (3:7) as eluent to give a solid (14 mg).

Additional Methods for Amide Preparation

Method D: A Representative Synthesis of Benzamides Using an Automated Parallel Synthesis Method The appropriate benzoic acid (2 mmol) is dissolved or suspended in 15 ml of chloroform and treated with 20 mmol of thionyl chloride. The reaction mixture is refluxed for fifteen minutes and the solvents are removed under vacuum. The residue is dissolved in 4 ml of anhydrous chloroform and 60 µl (30 µmole) of this solution is added to each well of the 96 well glass plates. Appropriate amine is then added to the corresponding well (60 µmole), followed by N,N-diisopropylethylamine (120 µmole). The plate is then heated at 65° C. for 15 minutes. The solvents are removed using an HT-12 Genevac centrifugal evacuator and 100 µl of DMSO is added to each well and the compounds are transferred to a 96-well polypropylene reaction plate. The plates are then sealed using an Abgene plate sealer and submitted to LC-MS purification.

Method E: A Representative Synthesis of Benzamides Using an Automated Parallel Synthesis Method In one well of a 96-well polypropylene reaction plate is added the appropriate benzoic acid (6.03 mg, 30 µmol) in 15 µl of anhydrous pyridine. To the reaction is added TFFH (TFFH is fluoro-N,N',N'-tetramethylformamidinium hexafluorophosphate; 12 mg, 45 µmol), followed by diisopropylethylamine (6.0 mg, 45 µmol), followed by the appropriate amine (60 µmol). The reaction plate is heated at 50° C. for 15 minutes and the solvent is evaporated. The residue is dissolved in DMSO and purified using LC-MS based purification (50 mm×10 mm Phenomenex Gemini Column using a 10-100% acetonitrile-water gradient).

Method F:

To a mixture of the acid (0.4 mmol), N-(3-dimethylaminopropyl)-N-ethylcarbodiimide hydrochloride (0.8 mmol), 1-Hydroxybenzotriazole hydrate (0.24 mmol) and CH$_2$Cl$_2$ (5 mL) is added the appropriate amine (0.5 mmol) and DIPEA (0.2 mL). The mixture is stirred at room temperature overnight, diluted with EtOAc, washed with brine, dried (Na$_2$SO$_4$), and concentrated. The residue is purified by column chromatography on silica gel to give the product.

Method G:

To a mixture of acid (1.0 mmol), N-(3-Dimethylaminopropyl)-N'-ethylcarbodiimide hydrochloride (385 mg, 2.0 mmol), 1-hydroxybenzotriazole hydrate (0.5-1.0 mmol), DMF (2 mL) and CH$_2$Cl$_2$ (5 mL) is added amine (1.2 mmol) and diisopropylethylamine (0.5 mL). The mixture is stirred at room temperature overnight, diluted with EtOAc, washed with brine, dried (Na$_2$SO$_4$), and concentrated. The residue is purified by column to give the amide.

Method H:

To a stirred solution of acid (1.0 mmol) in dry CH$_2$Cl$_2$ (10 mL) and DMF (2 drops) at 0° C. is added oxalyl chloride (1.5 mmol). The mixture is stirred at 0° C. for 1 h and then warmed to room temperature for 3 h. The solvent is removed in vacuo. A solution of the obtained acid chloride in CH$_2$Cl$_2$ (2 mL) is added to a solution of amine (1.0 mmol) in CH$_2$Cl$_2$ (3 mL) and pyridine (2 mL) at 0° C. The reaction mixture is stirred at rt overnight, and then diluted with EtOAc. The organic phase is washed with aq. NaHCO$_3$ solution and brine, dried (Na$_2$SO$_4$), and concentrated. The residue is purified by chromatography to give the amide.

Method I:

To a stirred solution of acid (0.25 mmol) in dry THF or CH$_2$Cl$_2$ (5 mL) and DMF (1 drop) at 0° C. is added oxalyl chloride (0.40 mmol). The mixture is stirred at 0° C. for 1 h and then warmed to rt. The solvent is removed in vacuo. A solution of the obtained acid chloride in CH$_2$Cl$_2$ (2 mL) is added to a solution of amine (0.25 mmol) in CH$_2$Cl$_2$ (10 mL), Et$_3$N (0.2 mL), DMAP (5 mg) at 0° C. The reaction mixture is stirred at rt overnight, and then diluted with EtOAc (100 mL). The organic phase is washed with aq. NaHCO$_3$ solution and brine, dried, and concentrated. The residue is purified by chromatography to give the amide.

Method J:

To a cooled (0° C.) and well stirred suspension of the appropriate acid (1 eq) in CH$_2$Cl$_2$ (ca. 3 mL per mmol) and DMF (catalytic quantity) is added oxalyl chloride (1.5 eq) slowly drop-wise and the mixture is agitated for one hour. The mixture is concentrated under vacuum and the residue re-suspended in $CH_2Cl_2$. The appropriate amine (0.5-1.0 eq) is then added and the mixture is stirred for 1-48 hours before being worked-up and purified.

Method K:

N,N-Diisopropylethylamine (1 eq) is added in one portion to a stirred mixture of 2-methyl-4-(3,3-dimethylbut-1-ynyl) benzoic acid (1 eq) and N,N,N',N'-tetramethyl-O-(7-azabenzotriazol-1-yl)uronium hexafluorophosphate (1.05 eq) in N,N-dimethylformamide (ca. 3 mL per 0.5 mmol of starting acid) at room temperature. The mixture is stirred at room temperature for approx. 2 hours then a solution of the appropriate amine (1 eq) in DMF (1 mL) is added in one portion. The mixture is stirred overnight then worked-up by pouring in to $H_2O$ (30 mL) and EtOAc (30 mL). The aqueous and organic layers are partitioned and the aqueous is extracted with EtOAc (2×30 mL). The combined organic extracts are washed with brine (1×30 mL), dried ($Na_2SO_4$), filtered and the solvent removed under vacuum to leave a crude residue. Appropriate purification is employed to furnish the desired final compound.

Method L:

A mixture of the acid (1 mmol), N-(3-dimethylaminopropyl)-N'ethylcarbodiimide hydrochloride (3 mmol), 1-hydroxybenzotriazole hydrate (1.5 mmol) and the amine (2 mmol) is stirred in DMF at room temperature overnight. The mixture is partitioned between EtOAc and water. The organic layer is separated and washed with saturated aqueous $NaHCO_3$, water, brine, dried ($Na_2SO_4$), filtered and the filtrate is concentrated in vacuo to a residue which is purified by flash column chromatography.

Method M:

DIPEA (0.92 mmol) is added to the solution of appropriate acid (0.46 mmol), appropriate amine (0.69 mmol) and TFFH (0.69 mmol) in anhydrous pyridine (3 mL) and the reaction mixture is stirred at 60° C. overnight. Volatiles are removed and the residue is suspended in water, extracted by EtOAc and the organic phase is washed by water, brine and is dried over $Na_2SO_4$, solvent is removed and the residue is chromatographed to give the product.

Method N:

DIPEA (0.92 mmol) is added to the solution of appropriate acid (4.0 mmol), appropriate amine (3.2 mmol) and TFFH (6.0 mmol) in anhydrous pyridine (10 mL) and the reaction mixture is stirred at 70° C. overnight. Volatiles are removed and the residue is dissolved in EtOAc and the organic phase is washed by water, $Na_2CO_3$ aqueous solution, brine and is dried over $Na_2SO_4$, solvent is removed and the residue is chromatographed to yield the product.

Method O:

To a solution of acid (0.5 mmol), N-(3-Dimethylaminopropyl)-N'-ethylcarbodiimide hydrochloride (1.0 mmol), 1-hydroxybenzotriazole hydrate (1.0 mmol) in DMF (5 mL) and $CH_2Cl_2$ (5 mL) are added amine (0.75 mmol) and diisopropylethylamine (1.0 mmol). The mixture is stirred at 40° C. overnight before diluted with EtOAc, ished with brine, dried over $Na_2SO_4$ and concentrated. The residue is purified by column to give the amide.

Method P:

The amine (1 eq) is added in one portion to a stirred solution of the acid (1 eq), N-(3-Dimethylaminopropyl)-N'-ethylcarbodiimide hydrochloride (1 eq), 4-N,N-dimethylaminopyridine (1 eq) and $Et_3N$ (2 eq) in $CH_2Cl_2$ (ca. 3 mL per 0.125 mmol) and the mixture stirred until completion of the reaction (typically left overnight). The mixture is diluted with more $CH_2Cl_2$ (30 mL) and washed with $H_2O$ (1×20 mL), then dried ($Na_2SO_4$), filtered and concentrated under vacuum. The residue is purfied by column chromatography on silica gel or preparative thin-layer chromatography.

General Method for Automated Parallel LC-MS Purification of Libraries

The libraries were purified using a Perkin Elmer AP1100 mass spectrometer coupled to Shimadzu LC pumps. The chromatographic method employed was 10-100% gradient of acetonitrile to water over 8 minutes at a flow rate of 6 ml per minute. The column used was a 10×50 mm YMC C18 and the compounds were collected using a Gilson 204 fraction collector.

Following the methods described above and the appropriate reagents, starting materials and purification methods known to those skilled in the art, the amide compounds of this invention were or can be prepared.

The synthetic and biological examples presented herein are offered to illustrate this invention and are not to be construed in any way as limiting the scope of this invention. In the examples below, all temperatures are in degrees Celsius (unless otherwise indicated).

The compounds that have been prepared in accordance with the invention are presented in Table 1, below. The syntheses of these representative compounds were carried out in accordance with the methods set forth above, and activity of the compounds was measured by percent inhibition in a calcium uptake assay, the details of which are described below.

Calcium Uptake Assay.

Functional activity of compounds against the VR1 receptor was determined by measuring changes in intracellular calcium in HEK 293 cells expressing hVR1. Compounds were examined for their ability to inhibit agonist-induced calcium influx. Dual wavelength ratiometric dye, Fura2, was used as an indicator of relative levels of $[Ca^{2+}]$ in a 96-well format using a Flex Station®, Molecular Devices.

Cell Line and Culture Conditions:

hVR1 was cloned into a pcDNA5/TO vector from Invitrogen and stably transformed into T-REx HEK 293 cell line from Invitrogen. HEK 293 cells expressing hVR1 were grown to confluency (24 hour culture) on PDL-coated, plastic 96-well black-walled plates, in the presence of DMEM medium containing 5% PenStrep, 5% Glutamax, 200 μg/mL Hygromycin, 5 μg/mL Blasticidin and 10% heat inactivated FBS. Twenty-four hours prior to assay, cells were transferred to DMEM media containing 1 μg/mL doxycycline. Prior to the assay, cells were loaded with 5 μg/mL Fura-2 (Molecular Probes) in saline solution (130 mM NaCl, 3 mM KCl, 1 mM $CaCl_2$, 0.6 mM $MgCl_2$, 10 mM HEPES, 10 mM glucose and 50 mM sucrose pH 7.4) at 37° C. for 40 minutes. The dye was then aspirated and replaced with 100 μL saline before commencement of the assay in Flex Station®.

Agonist Concentration and Compound Dilutions:

The agonist $EC_{50}$ was determined at the start of the assay and compound $IC_{50}$ experiments were run using an agonist concentration equal to its $EC_{50}$ as stimulus. The agonists used were capsaicin ($EC_{50}$=2.5 nM) and protons (saline solution plus 10 mM citric acid buffered to pH 5.7 with HCl). Compounds were tested at concentrations ranging from 10 nM to 3.3 µM.

The assay consists of two stages: a pre-treatment phase followed by a treatment phase. 50 µl of a compound solution was added to the cells (Pre-treatment). In some instances, following pre-treatment, 50 µl of the test compound in a saline solution at pH 5.1 was added (Treatment). Compounds were tested as follows: For the pre-treatment phase, 50 µL of 3× concentration of test compound in saline is added to cells containing 100 µL of saline to achieve a final concentration of x. For the treatment phase, at a determined time after pre-treatment, 50 µL of test compound plus agonist solution is added to cells at the relevant concentrations.

Recordings were made at 4 second intervals at wavelengths of 340 nm and 380 nm and the fluorescence ratio analyzed. Responses were measured as peak fluorescence ratio after compound-agonist addition minus baseline fluorescence ratio prior to treatment and were calculated using the SoftMaxPro software from Molecular Devices. Percent inhibition was calculated as follows and is depicted in Table 1:

$$\text{Percentage inhibition} = 1 - \frac{(\text{Compound Response} - \text{Control Response})}{(\text{Agonist Response} - \text{Control Response})} \times 100$$

Exemplary Compounds of the Invention

The following compounds have been or can be prepared according to the methods of the invention. For purposes of Tables 1 activity of each compound is expressed as follows:

"+" compound exhibited 0-25% inhibition of calcium ion influx

"++" compound exhibited 25-50% inhibition of calcium ion

"+++" compound exhibited 50-75% inhibition of calcium ion influx

"++++" compound exhibited 75% or greater inhibition of calcium ion influx Compounds with a percent inhibition represented by "++++" are of particular interest.

TABLE 1

AMIDE COMPOUNDS

| ID | STRUCTURE | MS calcd (observed) | $^1$H NMR | % Inhib. @ 0.3 µM |
|---|---|---|---|---|
| 1 | 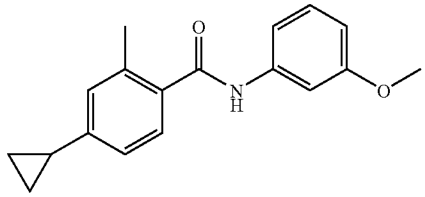 | 281.36 (282.30) | (CDCl$_3$) δ 7.47(1H, br. s), 7.78(2H, s), 7.69(1H, s), 7.43(1H, d), 6.97–6.91(2H, m), 2.83(3H, s), 2.49(3H, s), 1.93–1.86 (1H, m), 1.04–0.98(2H, m), 0.75–0.71 (2H, m) | +++ |
| 2 | 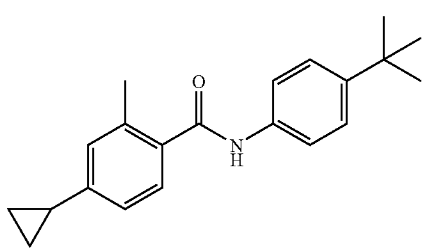 | 307.44 (308.30) | (CDCl$_3$) δ 7.53(1H, s), 7.51(1H, s), 7.41 (1H, s), 7.39–7.36(3H, m), 6.95(1H, s), 6.93–6.91(1H, m), 2.47(3H, s), 1.93–1.86 (1H, m), 1.32(9H, s), 1.03–0.98(2H, m), 0.74–0.70(2H, m) | + |
| 3 | 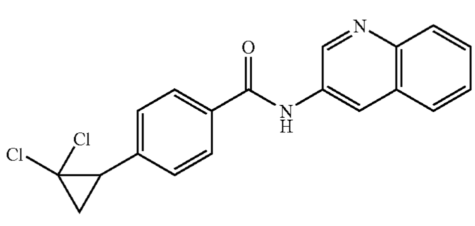 | 357.24 (357.1/ 359.2) | (CDCl$_3$) δ 8.92–8.91(1H, m), 8.89–8.88 (1H, m), 8.22(1H, s), 8.08(1H, d), 7.96 (1H, m), 7.94(1H, m), 7.86(1H, d), 7.69–7.64(1H, m), 7.59–7.55(1H, m), 7.43 (1H, s), 7.40(1H, s), 2.99(1H, dd), 2.08 (1H, dd), 1.95(1H, t) | +++ |
| 4 | 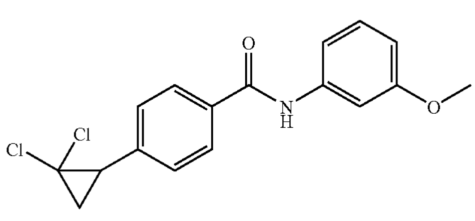 | 336.22 (336.40) | (CDCl$_3$) δ 7.87(1H, s), 7.85(1H, s), 7.80 (1H, br. s), 7.43(1H, t), 7.39(1H, s), 7.36 (1H, s), 7.27(1H, t), 7.10–7.01(1H, m), 6.73(1H, dd), 3.84(3H, s), 2.97(1H, t), 2.06(1H, dd), 1.93(1H, t) | ++++ |

TABLE 1-continued

AMIDE COMPOUNDS

| ID | STRUCTURE | MS calcd (observed) | $^1$H NMR | % Inhib. @ 0.3 μM |
|---|---|---|---|---|
| 5 | 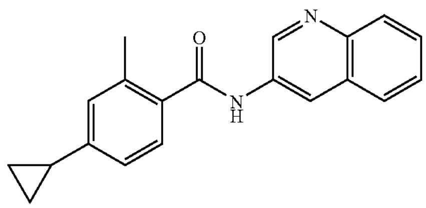 | 302.38 (303.30) | (CDCl$_3$) δ 8.92(1H, br. s), 8.76(1H, dd), 8.05(1H, dd), 7.96(1H, s), 7.84(1H, d), 7.66–7.62(1H, m), 7.57–7.53(1H, m), 7.45(1H, d), 6.97–6.92(2H, m), 2.51(3H, s), 1.93–1.85(1H, m), 1.05–0.99(2H, m), 0.76–0.71(2H, m) | ++++ |
| 6 | 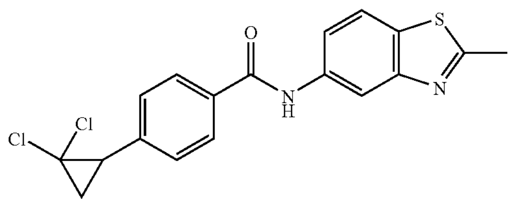 | 377.30 (377.0/ 379.1) | (CDCl$_3$) δ 7.43(1H, m), 7.22(1H, br. s), 7.20(1H, s), 7.18(1H, s), 7.08(1H, s), 7.07(1H, d), 6.69(1H, s), 6.67(1H, s), 2.27(1H, dd), 2.13(3H, s), 1.35(1H, dd), 1.23(1H, t) | ++++ |
| 7 | 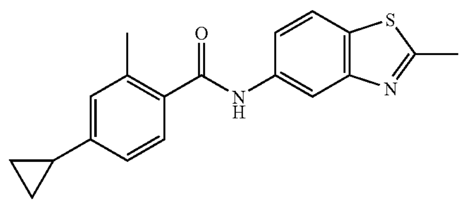 | 322.43 (323.20) | (CDCl$_3$) δ 8.05(1H, br. s), 7.78(2H, s), 7.69(1H, s), 7.43(1H, d), 6.97–6.91(2H, m), 2.83(3H, s), 2.49(3H, s), 1.93–1.86(1H, m), 1.04–0.98(2H, m), 0.75–0.71(2H, m) | ++++ |
| 8 | 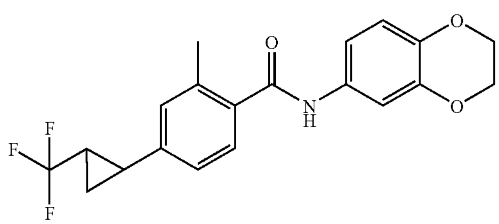 | 377.37 (378.10) | (d$_6$-DMSO) δ 10.05(s, 1H), 7.34(m, 2H), 7.15–7.08(m, 3H), 6.79(d, 1H), 4.21(m, 4H), 2.42(m, 1H), 2.33,(s, 3H), 2.29(m, 1H), 1.38(m, 1H), 1.30(m, 1H) | + |
| 9 | 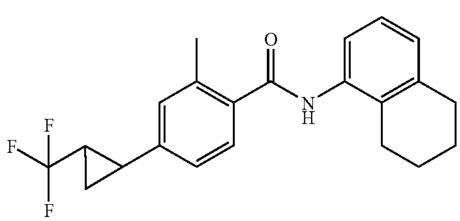 | 373.42 (374.10) | (d$_6$-DMSO) δ 9.53(s, 1H), 7.43(d, 1H), 7.18(d, 1H), 7.15–7.04(m, 3H), 6.96(d, 1H), 2.75(t, 2H), 2.67(t, 2H), 2.42(m, 1H), 2.39(s, 3H), 2.31(m, 1H), 1.71(m, 4H), 1.39(m, 1H), 1.30(m, 1H) | + |
| 10 | 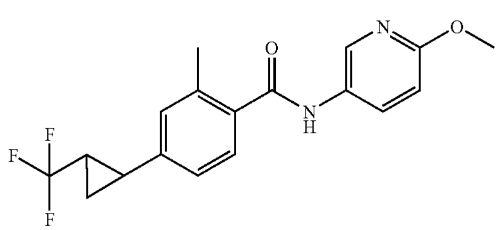 | 350.34 (351.10) | (d$_6$-DMSO) δ 10.25(s, 1H) 8.48(d, 1H), 8.01(dd, 1H), 7.44(d, 1H), 7.19–7.10(m, 2H), 6.83(d, 1H), 3.83(s, 3H), 2.42(m, 1H), 2.36(s, 3H), 2.31(m, 1H), 1.39(m, 1H), 1.30(m, 1H) | ++ |
| 11 | 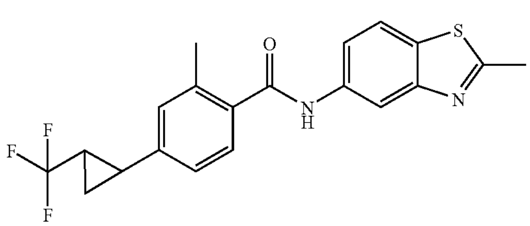 | 390.43 (391.40) | (d$_6$-DMSO) δ 10.39(s, 1H), 8.40(d, 1H), 7.94(d, 1H), 7.69(dd, 1H) 7.43(d, 1H), 7.19–7.12(m, 2H), 2.27(s, 3H), 2.45(m, 1H), 2.38(s, 3H), 2.32(m, 1H), 1.38(m, 1H), 1.32(m, 1H) | ++++ |

TABLE 1-continued

AMIDE COMPOUNDS

| ID | STRUCTURE | MS calcd (observed) | ¹H NMR | % Inhib. @ 0.3 μM |
|---|---|---|---|---|
| 12 | 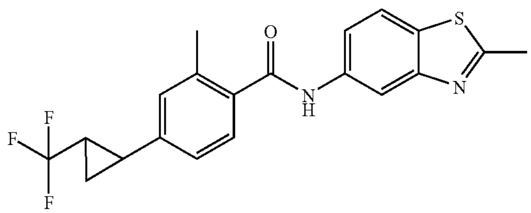 | 390.43 (391.30) | (CDCl$_3$) δ 8.11(s, 1H), 7.80(br. s 2H), 7.61, (s, 1H), 7.47(d, 1H), 7.28–7.18(m, 2H), 2.87(s, 3H), 2.52(s, 3H), 2.47(m, 1H), 1.92(m, 1H), 1.45(s, 1H), 1.32(m, 1H) | ++++ |
| 13 | 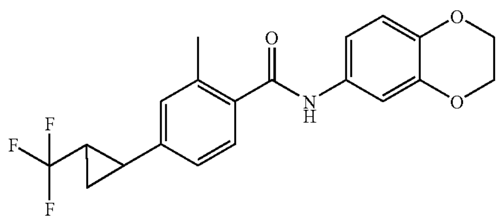 | 377.37 (378.10) | (CDCl$_3$) δ 7.40(d, 2H) 7.30(s, 1H) 7.22–7.15(m, 2H), 6.98(dd, 1H), 6.84(d, 1H), 4.25(m, 4H), 2.49(s, 3H), 2.22(m, 1H), 1.90(m, 1H), 1.44(m, 1H), 1.30(m, 1H) | +++ |
| 14 | 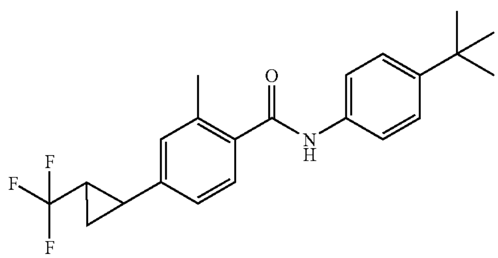 | 375.44 (376.10) | (CDCl$_3$) δ 7.54(d, 2H), 7.45–7.36(m, 4H), 7.23–7.15(m, 2H), 2.49(s, 3H), 2.46(m, 1H), 1.91(m, 1H), 1.45(m, 1H), 1.37(s, 9H), 1.32(m, 1H) | ++ |
| 15 | 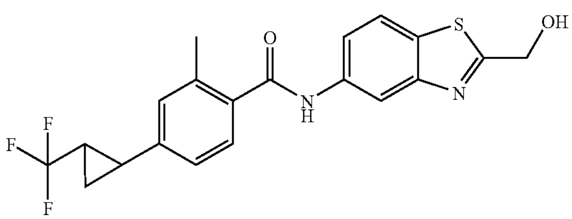 | 406.43 (407.20) | (CDCl$_3$) δ 8.20(s, 1H), 7.88(d, 1H), 7.80 (m, 1H), 7.60(s, 1H), 7.48(d, 1H), 7.06–7.00(m, 2H), 5.11(s, 2H), 2.52(s, 3H), 2.37(m, 1H), 1.84(m, 1H), 1.43(m, 1H), 1.30(m, 1H) | ++++ |
| 16 | 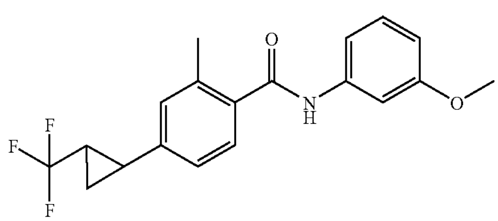 | 349.36 (349.90) | (CDCl$_3$) δ 7.45–7.39(m, 3H), 7.29–7.16 (m, 3H), 7.06(d, 1H), 6.71(dd, 1H), 3.84 (s, 3H), 2.49(s, 3H), 2.46(m, 1H), 1.92 (m, 1H), 1.45(m, 1H), 1.32(m, 1H) | ++ |
| 17 | 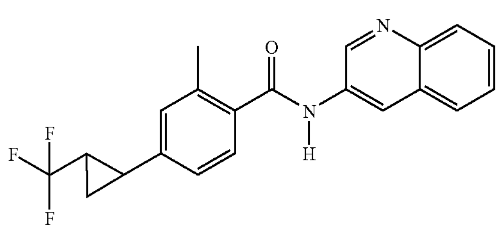 | 370.38 (371.20) | (CDCl$_3$) δ 8.95(1H, br. s), 8.78(1H, br. s), 8.08(1H, d), 7.87(1H, d), 7.79(1H, s), 7.67(1H, t), 7.57(1H, t), 7.53(1H, d), 7.07–7.03(2H, m), 2.54(3H, s), 2.41–2.35 (1H, m), 1.91–1.81(1H, m), 1.47–1.41 (1H, m), 1.26–1.20(1H, m) | +++ |

TABLE 1-continued

AMIDE COMPOUNDS

| ID | STRUCTURE | MS calcd (observed) | ¹H NMR | % Inhib. @ 0.3 μM |
|---|---|---|---|---|
| 18 | 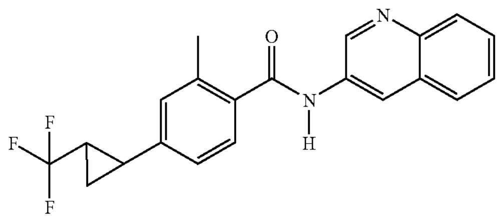 | 370.38 (371.10) | (CDCl$_3$) δ 8.95(1H, br. s), 8.78(1H, br. s), 8.08(1H, d), 7.87(1H, d), 7.79(1H, s), 7.67(1H, t), 7.57(1H, t), 7.53(1H, d), 7.07–7.03(2H, m), 2.54(3H, s), 2.41–2.35 (1H, m), 1.91–1.81(1H, m), 1.47–1.41 (1H, m), 1.26-1.20(1H, m) | +++ |
| 19 | 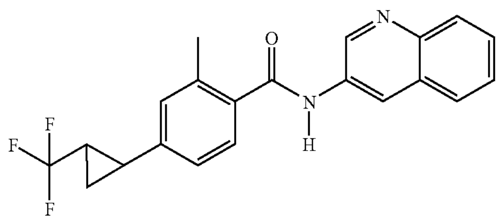 | 370.38 (371.20) | (CDCl$_3$) δ 8.94(1H, br s), 8.78(1H, m), 8.07(1H, d), 7.89–7.84(2H, m), 7.66(1H, t), 7.57(1H, t), 7.51(1H, d), 7.25–7.21 (2H, m), 2.54(3H, s), 2.49(1H, dd), 1.97– 1.88(1H, m), 1.49(1H, dd), 1.37–1.31 (1H, m) | + |
| 20 | 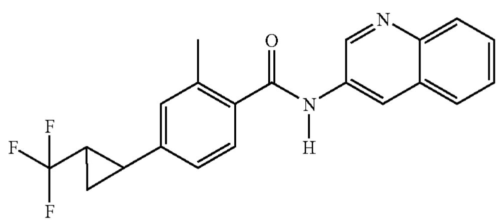 | 370.38 (370.70) | (CDCl$_3$) δ 8.94(1H, br s), 8.78(1H, m), 8.07(1H, d), 7.89–7.84(2H, m), 7.66(1H, t), 7.57(1H, t), 7.51(1H, d), 7.25–7.21 (2H, m), 2.54(3H, s), 2.49(1H, dd), 1.97– 1.88(1H, m), 1.49(1H, dd), 1.37–1.31 (1H, m) | ++ |

EXAMPLE 1

Two-Electrode Voltage Clamp Recording Using Opus Express®

Oocytes are prepared by surgically removing *Xenopus* ovaries obtained from NASCO. The oocytes are isolated by enzymatic dissociation using collagenase (Worthington, 2 mg/ml). Oocytes are then individually injected with HsVR1 RNA. Each oocyte receives 64 nl of RNA solution in water at a concentration of 0.5 μg/μl. Injected oocytes are stored in standard oocyte incubation solution, ND96, containing (in mM) 96 NaCl, 2 KCl, 1 MgCl$_2$, 1.8 CaCl$_2$ and 50 μg/ml Gentamicin at 16° C. Capsaicin induced VR1 current is observed in oocytes 4-5 days after injection.

Eight oocytes are placed in the recording chambers. Each oocyte is impaled by 2 glass electrodes having resistances of 0.5 to 1 MOhm when filled with a 3 M KCl solution. Electrode advancement and oocyte impalement are under software control (OpusXpress® 1.1 Molecular Devices Corporation).

The solutions are prepared in 96 well plates and robotically pipetted into the oocyte recording chambers by an 8 channel pipettor. Test solution delivery to the oocytes during the experiment is also under software control.

A set of plates with wells containing 250 nM capsaicin are used initially to verify VR1 expression. Capsaicin induced VR1 current is modulated in a calcium dependent manner. The oocytes are exposed to several 250 μl applications of 250 nM capsaicin until a stable current amplitude is obtained with each application.

A set of 96 well plates containing the test solutions is prepared so that the sequence of solution application to the oocyte is as follows: 250 μls of 250 nM capsaicin is followed by a several minute wash with standard oocyte saline. 1 ml of the test compound is then added at a particular test concentration, followed immediately by 250 μl of the compound at the same concentration plus 250 nM capsaicin. The capsaicin induced VR1 current is recorded in the absence and presence of the test compound for each concentration. The standard test concentrations for the compounds tested here usually range from 0.3 to 2000 nM.

Quantitative measurement of VR1 current block is done by calculating the area under the curve described by the inward current. The resulting numbers for capsaicin induced currents in the presence of increasing compound concentration are normalized to the maximum current obtained. These points are then plotted on a logarithmic scale and fitted by a Hill function. The IC$_{50}$ is calculated from the resulting Hill fit.

FIG. 1 depicts the IC$_{50}$ measurement using the protocol described above for Compound having I.d. No 7. An IC$_{50}$ of 178±26 was obtained under experimental conditions described herein. Data were obtained from 5 oocytes (n=5).

All publications, patents and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of

What is claimed is:

1. A compound having a formula:

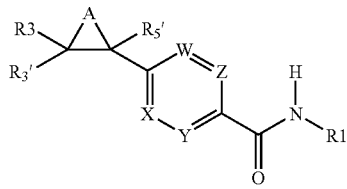

IA or a pharmaceutically acceptable salt thereof, and stereoisomers and tautomers thereof, wherein:
A is $CR^5R^6$; each of $R^{3'}$, $R^5$, $R^{5'}$ and $R^6$ is independently selected from H, halo, haloalkyl and hydroxyalkyl; provided that only one of $R^{3'}$, $R^5$, $R^{5'}$ and $R^6$ is other than H at any one time;
each of W and X is independently CH, CMe, CCl or CF; each Y and Z is independently $CR^4$;
$R^1$ is 3-quinolinyl, unsubstituted or substituted with alkyl, hydroxyalkyl, haloalkyl, amino, alkylamino, dialkylamino, arylamino, alkylarylamino, alkoxy, cycloalkylalkoxy, alkoxycarbonyl, arylalkyloxy, aralkyl, sulfo, sulfonyl, sulfanyl, aminosulfonyl, carboxy, carbamoyl, cyano, halo, hydroxy, nitro or thiol;
$R^3$ is selected from halo, $C_1$-$C_6$ alkyl, halo $C_1$-$C_6$ alkyl, or hydroxy $C_1$-$C_6$ alkyl; and each $R^4$ is independently hydrogen, alkyl, hydroxyalkyl, haloalkyl, amino, alkylamino, dialkylamino, arylamino, alkylarylamino, alkoxy, cycloalkylalkoxy, alkoxycarbonyl, arylalkyloxy, aralkyl, sulfo, sulfonyl, sulfanyl, aminosulfonyl, carboxy, carbamoyl, cyano, halo, hydroxy, nitro or thiol.

2. A compound according to claim 1 wherein the compound is depicted by a formula

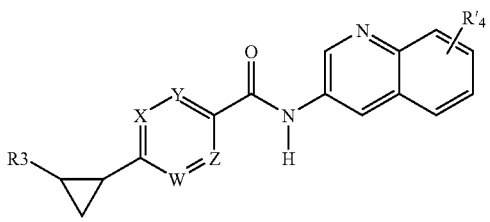

and wherein W, X, Y, and Z are as described in claim 1; $R^3$ is t-Bu or $CF_3$; and $R^{4'}$ is H, $C_1$-$C_6$ alkyl, or hydroxy $C_1$-$C_6$ alkyl.

3. A compound according to claim 1 wherein each of $R^5$, $R^{5'}$ and $R^6$ is independently H; $R^{3'}$ selected from H, halo, $C_1$-$C_6$ alkyl, halo $C_1$-$C_6$ alkyl, or hydroxy $C_1$-$C_6$ alkyl; and $R^3$ is independently selected from halo, $C_1$-$C_6$ alkyl, halo $C_1$-$C_6$ alkyl, or hydroxy $C_1$-$C_6$ alkyl.

4. A compound according to claim 1 wherein each of $R^5$, $R^{5'}$ and $R^6$ is independently H; $R^{3'}$ selected from H, and halo, and $R^3$ is independently selected from halo, $C_1$-$C_6$ alkyl, halo $C_1$-$C_6$ alkyl, or hydroxy $C_1$-$C_6$ alkyl.

5. A compound according to claim 1 wherein each of $R^5$, $R^{5'}$ and $R^6$ is independently H; and each of $R^3$ and $R^{3'}$ is Cl.

6. A compound according to claim 1 wherein each of $R^{3'}$, $R^5$, $R^{5'}$ and $R^6$ is independently H; and $R^3$ is independently selected from halo, $C_1$-$C_6$ alkyl, halo $C_1$-$C_6$ alkyl, or hydroxy $C_1$-$C_6$ alkyl.

7. A compound according to claim 1 wherein each of $R^{3'}$, $R^5$, $R^{5'}$ and $R^6$ is independently H; and $R^3$ is independently selected t-Bu and $CF_3$.

8. A compound according to claim 1 wherein $R^1$ is substituted 3-quinolinyl and the substitution is selected from H, halo, $C_1$-$C_6$ alkyl, halo $C_1$-$C_6$ alkyl, hydroxy $C_1$-$C_6$ alkyl, cyano, $C_1$-$C_6$ alkoxy, halo $C_1$-$C_6$ alkoxy, amino, $C_1$-$C_6$ alkylamino, $C_1$-$C_6$ dialkylamino, $SO_2$—$C_1$-$C_6$ alkyl, $SO_2N(C_1$-$C_6$ alkyl$)_2$, and carboxy.

9. A compound according to claim 1 wherein $R^1$ is:

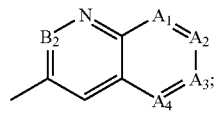

$A^1$, $A^2$, $A^3$, $A^4$; and $B^2$ are independently $CR^{4'}$; and each of $R^{4'}$ is independently H, $C_1$-$C_6$ alkyl, halo, or hydroxy $C_1$-$C_6$ alkyl.

10. A compound according to claim 1 wherein $R^1$ is

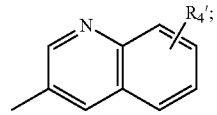

and $R^{4'}$ is independently H, $C_1$-$C_6$ alkyl or hydroxy $C_1$-$C_6$ alkyl.

11. A compound according to claim 10 wherein $R^{4'}$ is hydroxy $C_1$-$C_6$ alkyl.

12. A compound according to claim 10 wherein $R^{4'}$ is —$(CH_2)_n$—OH; and wherein n is selected from 1-3.

13. A compound according to claim 10 wherein $R^{4'}$ is $CH_2OH$.

14. A compound according to either of claims 1 or 2, each of W, X, Y and Z is CH.

15. A compound according to either of claims 1 or 2, wherein each of Y and Z is $CR^4$ and $R^4$ is independently selected from hydrogen, $C_1$-$C_6$ alkyl, trihalo $C_1$-$C_6$ alkyl and halo.

16. A compound according to claim 15 wherein each of $R^4$ is independently H, $CH_3$, $CF_3$, Cl or F.

17. A compound according to either of claims 1 or 2, wherein each of W, X, and Z is CH; and Y is C—$CH_3$, C—Cl or C—F.

18. A compound according to claim 1 wherein $R^4$ is H.

19. A compound according to claim 1 selected from the group consisting of:
4-(2,2-dichlorocyclopropyl)-N-(quinolin-3-yl)benzamide;
(1R,2R)2-methyl-N-(quinolin-3-yl)-4-(2-(trifluoromethyl)cyclopropyl)benzamide;

(1R,2S)2-methyl-N-(quinolin-3-yl)-4-(2-(trifluoromethyl)cyclopropyl)benzamide;

(1S,2R)2-methyl-N-(quinolin-3-yl)-4-(2-(trifluoromethyl)cyclopropyl)benzamide; and (1S,2S)2-methyl-N-(quinolin-3-yl)-4-(2-(trifluoromethyl)cyclopropyl)benzamide.

20. A composition comprising a pharmaceutically acceptable carrier and a pharmaceutically effective amount of a compound of claim 1.

21. The composition of claim 20 wherein the carrier is a parenteral carrier, oral or topical carrier.

22. A method for preparing a compound of claim 1 which comprises contacting a compound of the formula:

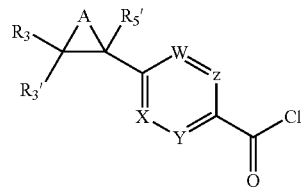

with a compound of the formula $R^1NH_2$ under conditions sufficient to form a compound according to claim 1; and wherein A, W, X, Y, Z, $R^1$, $R^3$, $R^{3'}$, and $R^{5'}$ are as described in claim 1.

23. The compound 4-cyclopropyl-2-methyl-N-(quinolin-3-yl)benzamide.

* * * * *